US007060811B2

(12) United States Patent
Aldaz et al.

(10) Patent No.: US 7,060,811 B2
(45) Date of Patent: Jun. 13, 2006

(54) WWOX: A TUMOR SUPPRESSOR GENE MUTATED IN MULTIPLE CANCERS

(75) Inventors: C. Marcelo Aldaz, Austin, TX (US); Andrzej Bednarek, Lodz (PL)

(73) Assignee: Board of Regents, The University of Texas System, Austin, TX (US)

( * ) Notice: Subject to any disclaimer, the term of this patent is extended or adjusted under 35 U.S.C. 154(b) by 192 days.

(21) Appl. No.: 09/978,318

(22) Filed: Oct. 15, 2001

(65) Prior Publication Data

US 2006/0024780 A1 Feb. 2, 2006

Related U.S. Application Data

(60) Provisional application No. 60/240,277, filed on Oct. 13, 2000.

(51) Int. Cl.
*C07N 21/02* (2006.01)
(52) U.S. Cl. .................... 536/23.5; 536/23.1; 435/69.1; 435/320.1; 530/350
(58) Field of Classification Search ............... 536/23.1, 536/23.5; 435/69.1, 320.1; 530/350
See application file for complete search history.

(56) References Cited

FOREIGN PATENT DOCUMENTS

| AU | PQ 4711 | 12/1999 |
|---|---|---|
| WO | WO 01/44466 | 6/2001 |
| WO | 02/12544 | * 2/2002 |

OTHER PUBLICATIONS

Skolnick et al. (Trends in Biotech., 18(1):34-39, 2000).*
Genbank Accession No AF211943.*
Aldaz et al., "Comparative allelotype of in situ and invasive human breast cancer: high frequency of microsatellite instability in lobular breast carcinomas," *Cancer Res.*, 55:3976-3981, 1995.
Andre and Springael, "WWP, a new amino acid motif present in single or multiple copies in various proteins including dystrophin and the SH3-binding Yes— associated protein YAP65," *Biochem. Biophys. Res. Commun.*, 205(2):1201-1205, 1994.
Bedford et al., "WW domain-mediated interactions reveal a spliceosome-associated protein that binds a third class of proline-rich motif: the proline glycine and methionine-rich motif, " *Proc. Natl. Acad. Sci. USA*, 95:10602-10607, 1998.
Bednarek and Aldaz, "Charaterization of transcripts from a commonly deleted area of chromosome 16(q23.3-q24.1) in human breast cancer," *Proc. Amer. Assoc. Cancer Res.*, 39:128, #872, 1998.
Bednarek et al., "WWOX, a novel WW domain-containing protein mapping to human chromosome 16q23.3-24.1, a region frequently affected in breast cancer," *Cancer Res.*, 60:2140-2145, 2000.

Bednarek et al., "WWOX, the FRA16D gene, behaves as a suppressor of tumor growth," *Cancer Res.*, 61:8068-8073, 2001.
Bork and Subol, "The WW domain: a signalling site in dystrophin?" *Trends Biochem. Sci.*, 19:531-533, 1994.
Carter et al., "Allelic loss of chromosomes 16q and 10q in human prostate cancer," *Proc. Natl. Acad. Sci. USA*, 87: 8751-8755, 1990.
Chan et al., "Formin binding proteins bear WWP/WW domains that bind proline-rich peptides and functionally resembel SH3 domains," *EMBO J.*, 15(5):1045-1054, 1996.
Chang et al., "Hyaluronidase induction of a WW domain-containing oxidoreductase that enhanced tumor necrosis factor cytotoxicity," *J. Biol. Chem.*, 276:3361-3370, 2001.
Chen and Sudol, "The WW domain of Yes-associated protein binds a proline-rich ligand that differs from the consensus established for Src homology 3-binding modules," *Proc. Natl. Acad. Sci. USA*, 92:7819-7823, 1995.
Chen et al., "Deletion map of chromosome 16q in ductal carcinoma in situ of the breast: refining a putative tumor suppressor gene region," *Cancer Res.* 56:5605-5609, 1996.
Chesi et al., "Frequent dysregulation of the c-maf proto-oncogene at 16q23 by translocation to an Ig locus in multiple myeloma," *Blood*, 91:4457-4463, 1998.
Cleton-Jansen et al., "At least two different regions are involved in allelic imbalance on chromosome arm 16q in breast cancer," *Genes, Chromos, Cancer*, 9:101-107, 1994.
Crawford et al., "The PISSLRE gene: structure, exon skipping, and exclusion as tumor suppressor in breast cancer," *Genomics*, 56:90-97, 1999.
Duax and Ghosh, "Structure and function of steroid dehydrogenases involved in hypertension, fertility, and cancer," *Steroids*, 62:95-100, 1997.
Dutrillaux et al., "Characterization of chromosal anomalies in human breast cancer. A comparison of 30 paradiploid cases with few chromosome changes," *Cancer Genet. Cytogenet.*, 49:203-217, 1990.
GenBank Accession No. AF179633.
GenBank Accession No. AF211943.
GenBank Accession No. AF212843.
GenBank Accession No. AF227526.
GenBank Accession No. AF227527.
GenBank Accession No. AF227528.
GenBank Accession No. AF395123.
GenBank Accession No. AF395124.
GenBank Accession No. U13395, locus ID 9621.
Jornvall et al., "Short-chain dehydrogenases/reductases (SDR)," *Biochemistry*, 34:6003-6013, 1995.

(Continued)

*Primary Examiner*—Sheela J. Huff
(74) *Attorney, Agent, or Firm*—Fulbright & Jaworski, L.L.P.

(57) ABSTRACT

The present invention provides the isolation and cloning of WWOX, a novel WW domain-containing protein mapping to human chromosome 16q23.3–24.1, a region frequently affected in several cancers. This gene encodes a tumor suppressor with apoptotic functions. The invention provides WWOX nucleic acid- and polypeptide-based cancer therapies. The invention also provides methods for cancer detection, diagnosis and prognosis involving WWOX nucleic acids and polypeptides.

8 Claims, 5 Drawing Sheets

OTHER PUBLICATIONS

Krummel et al., "The characterization of the common fragile site FRA16D and its involvement in multiple myeloma translocation," *Genomics*, 69:37-46, 2000.

Lu et al., "Function of WW domains as phosphoserine—or phosphothreonine-binding modules," *Science*, 283:1325-1328, 1999.

Mangelsdorf et al., "Chromosomal fragile site FRA16D and DNA instability in cancer," *Cancer Res.*, 60: 1683-1689, 2000.

Paige et al., "A 700-kb physical map of a region of 16q23.2 homozygously deleted in multiple cancers and spanning the common fragile site FRA16D," *Cancer Res.* 60:1690-1697, 2000.

Paige et al., "WWOX: A candidate tumor suppressor gene involved in multiple tumor types," *Proc. Natl. Acad. Sci. USA*, 98:11417-11422, 2001.

Pandis et al., "Whole-arm t(1;16) and i(1q) as sole anomalies identify gain of 1q as a primary chromosomal abnormality in breast cancer," *Genes Chromosomes Cancer*, 5:235-238, 1992.

Price et al., "Tumorigenicity and metastasis of human breast carcinoma cell lines in nude mice," *Cancer Res.* 50:717-721, 1990.

Richards, "Fragile and unstable chromosomes in cancer: causes and consequences," *Trends Genet.*, 17:339-345, 2001.

Ried et al., "Common chromosomal fragile site FRA16D sequence: identification of the FOR gene spanning FRA16D and homozygous deletions and translocation breakpoints in cancer cells," *Human Molecular Genetics*, 9(11):1651-1663, 2000.

Sato et al., "Allelotype of breast cancer: cumulative allele losses promote tumor progression in primary breast cancer," *Cancer Res.*, 50:7184-7189, 1990.

Savino et al., "Characterization of copine VII, a new member of the copine family, and its exclusion as a candidate in sporadic breast cancers with loss of heterozygosity at 16q24.3," *Genomics*, 61:219-226, 1999.

Smith et al., "Common fragile sites and cancer (Review)," *Int. J. Oncol.*, 12:187-196, 1998.

Staub et al., "WW domains of Nedd4 bind to the proline-rich PY motifs in the epithelial Na+ channel deleted in Liddle's syndrome," *Embo. J.*, 15:2371-2380, 1996.

Sudol and Hunter, "NeW wrinkles for an old domain," *Cell*, 103:1001-1004, 2000.

Sudol et al., "Characterization of the mammalian YAP (Yes-associated protein) gene and its role in defining a novel protein module, the WW domain," *J. Biol. Chem.*, 270:14733-14741, 1995.

Sudol, "Yes-associated protein (YAP65) is a proline-rich phosphoprotein that binds to the SH3 domain of the Yes proto-oncogene product," *Oncogene*, 9:2145-2152, 1994.

Sutherland et al., "Fragile sites still breaking," *Trends Genet.*, 14:501-506, 1998.

Tsuda et al., "Allele loss on chromosome 16q24..2-qter occurs frequently in breast cancer irrespectively of differences in phenotype and extent of spread," *Cancer Res.*, 54:513-517, 1994.

Whitmore et al., "Construction of a high-resolution physical and transcription map of chromosome 16q24.3: a region of frequent loss of heterozygosity in sporadic breast cancer," *Genomics*, 50:1-8, 1998.

* cited by examiner

```
          10        20        30        40
MAALRYAGLDDTDSEDE LPPGWEERTTKDGWVYYANHTEEKTQWEHP KTG
          60        70        80        90
KRKRVAGD LPYGWEQETDENGQVFFVDHINKRTTYLDP RLAFTVDDNPTK
         110       120       130       140
PTTRQRYDGSTTAMEILQGRDFTGKVVVVTGANSGIGFETAKSFALHGAH
         160       170       180       190
VILACRNMARASEAVSRILEEWHKAKVEAMTLDLALLRSVQHFAEAFKAK
         210       220       230       240
NVPLHVLVCNAATFALPWSLTKDGLETTFQVNHLGHFYLVQLLQDVLCRS
         260       270       280       290
APARVIVVSSESHRFTDINDSLGKLDFSRL PTKNDYWAMLA    LCN
         310       320       330       340
ILFSNELHRRLSPRGVTSNAVHPGNMMYSNIHRSWWVYTLLFTLARPFTK
         360       370       380       390
SMQQGAATTVYCAAVPELEGLGGMYFNNCCRCMPSPEAQSEETARTLWAL
         410
SERLI QERLGSQSG
```

FIG. 2a

```
WW consensus    IppgWeerkdpdGrpYYyNhnTkeTqWekP
                IppgWeer++ dG +YY Nh   +TqWe+P
WWOX1        18 LPPGWEERTTKDGWVYYANHTEEKTQWEHP 47

WW consensus    IppgWeerkdpdGrpYYyNhnTkeTqWekP
                Ip gWe+ +d++G++++++h++k+T++ +P
WWOX1        59 LPYGWEQETDENGQVFFVDHINKRTTYLDP 88
```

FIG. 2b

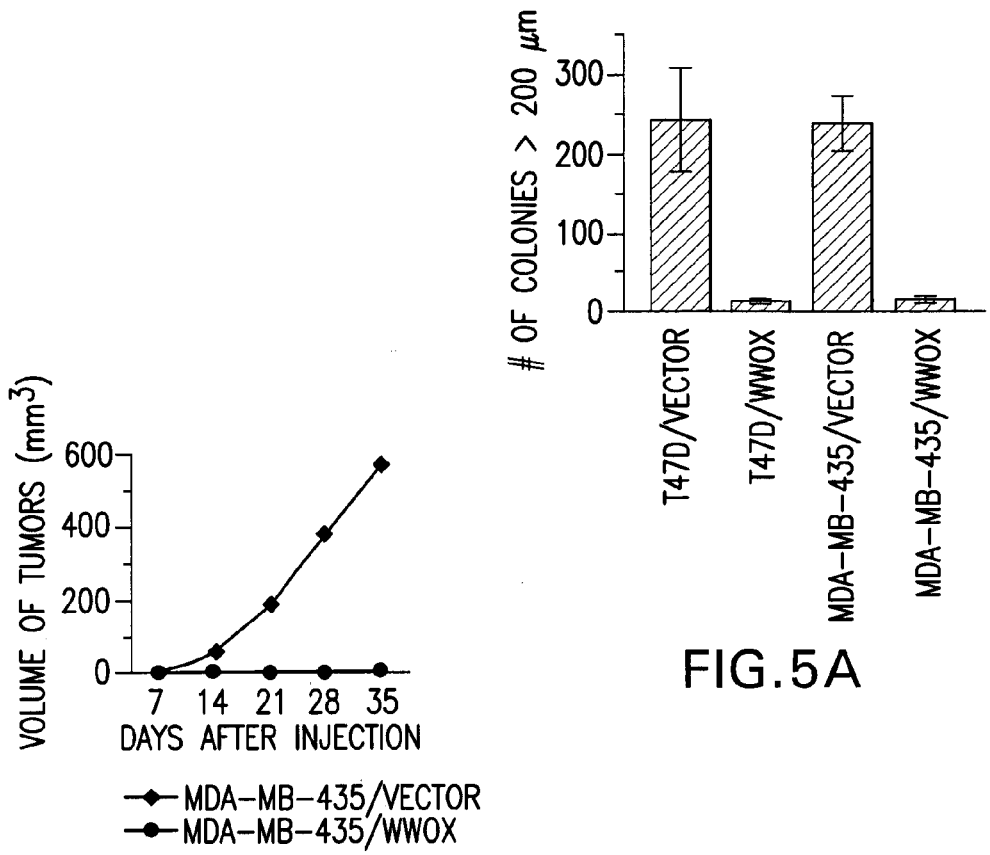
FIG.5A
FIG.5B
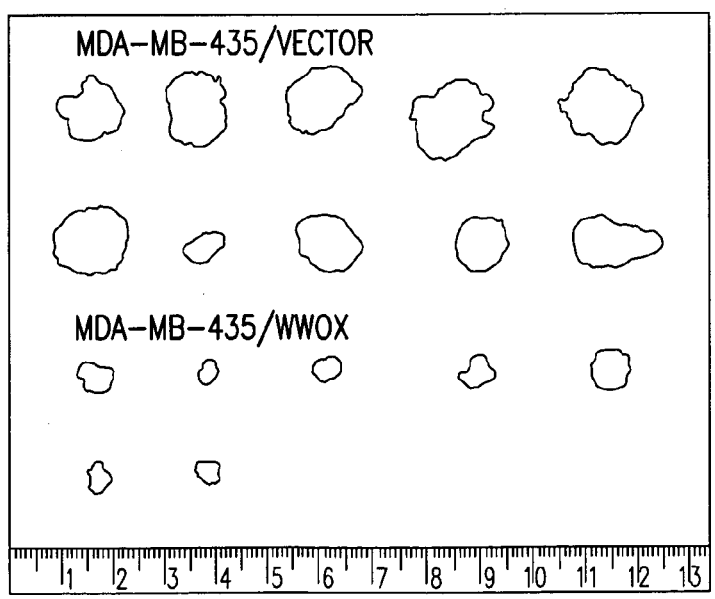
FIG.5C

WWOX: A TUMOR SUPPRESSOR GENE MUTATED IN MULTIPLE CANCERS

The present application claims priority to U.S. Provisional Patent Application Ser. No. 60/240,277 filed Oct. 13, 2000 now abandoned. The entire text of the above-referenced disclosure is specifically incorporated by reference herein without disclaimer.

The government may own rights in the present invention pursuant to grant number DAMD 17-94-J-4078 from the Breast Cancer Research Program sponsored by the Department of the Defense, U.S. Army Medical Research and Material Command, Congressionally Directed Medical Research Programs.

BACKGROUND OF THE INVENTION

1. Field of the Invention

The present invention relates generally to the fields of molecular biology, oncology and gene therapy. More particularly, it concerns the identification of a novel tumor suppressor gene, WWOX, which is mutated in several cancers. The invention provides methods of utilizing the tumor suppressor gene as a cancer diagnostic tool. The invention also provides methods to identify patients with a higher susceptibility to certain cancer types involving the status of the WWOX tumor suppressor. Furthermore, the invention provides methods for the treatment of cancers comprising administering a therapeutic nucleic acid and/or polypeptides based on the tumor suppressor gene.

2. Description of Related Art

Second only to heart disease, cancer is the leading cause of death in the United States, striking one in two men and one in three women (Landis, 1998). Normal tissue homeostasis is a highly regulated process of cell proliferation and cell death. The development of cancer is the culmination of complex, multistep biological processes, occurring through the accumulation of genetic alteration which typically cause an imbalance in the genes controlling either cell proliferation or cell death. Many if not all of these alterations involve specific cellular growth-controlling genes that are mutated. These genes typically fall into two categories: proto-oncogenes and tumor suppressor genes. Mutations in genes of either class generally lead to abnormal cell-growth and result in cancers.

The function of tumor suppressor genes is to antagonize cellular proliferation. When a tumor suppressor gene is inactivated, for example by mutations such as deletions or point mutations, the cell's regulatory machinery for controlling growth is upset. Several studies have shown that the neoplastic tendencies of such mutated cells can be suppressed by the addition of a nonmutated (wild-type) version of the tumor suppressor gene that expresses its gene product (Levine, 1995). For example, a point mutation in the p53 tumor suppressor protein results in the complete loss of wild-type p53 function (Vogelstein and Kinzler, 1992) and acquisition of "dominant" tumor promoting function.

Currently, there are few effective options for the diagnosis and treatment of many common cancer types. The most conventional options of cancer treatment are surgery, radiation therapy and chemotherapy. Typically, surgical methods are used for the diagnosis (by surgical biopsy) and treatment of cancer (surgery to remove cancerous growths). However, if the cancer has metastasized and is widespread, surgery is unlikely to result in a cure and an alternate approach must be taken. Radiation therapy, chemotherapy and immunotherapy are other forms of cancer treatment (Mayer, 1998; Ohara, 1989; Ho et al., 1998). However, both radiation therapy and chemotherapy are associated with numerous side effects since normal cells are also affected and these include skin irritation, difficulty swallowing, dry mouth, nausea, diarrhea, hair loss, mouth sores, fatigue, bleeding to name a few. Immunotherapy, a rapidly evolving area in cancer research, is yet another option for the treatment of certain types of cancers which unfortunately has not been sufficient to prevent most tumor growths.

Gene therapy is another emerging field in biomedical research with a focus on the treatment of disease by the introduction of therapeutic recombinant nucleic acids into somatic cells of patients. Various clinical trials using gene therapies have been initiated and include the treatment of various cancers, AIDS, cystic fibrosis, adenosine deaminase deficiency, cardiovascular disease, Gaucher's disease, rheumatoid arthritis, and others.

While there are some gene therapies for cancer treatments in clinical trials, not all cancer causing genes have been identified. As mutations in oncogenes and tumor-suppressor genes are the major causes for loss of cell-cycle control, there is a growing need to identify more genes of these two classes. Some examples of the tumor suppressor genes targeted for anticancer genetherapies are p53 and retinoblastoma. However, not all cancers are due to mutations of these two genes. Given the diverse types of cancers and the large population affected by cancer there is need to identify more such tumor suppressor genes involved in cancer to find better and effective anticancer treatments.

SUMMARY OF THE INVENTION

The present invention seeks to overcome drawbacks inherent in the art by disclosing the cloning and characterization of a novel gene, mutated versions of which are expressed in cancer cells. The invention further provides nucleic acids, polypeptides, proteins encoded by this gene and antibodies towards various WWOX polypeptides and proteins. The invention also encompasses methods of making and using such nucleic acids and the related polypeptides, proteins and antibodies. Furthermore, the invention provides methods for the diagnosis, detection, prognosis and treatment of cancers using one or more of the foregoing compositions.

Thus, the invention describes the isolation of a novel gene named WWOX. The WWOX gene is identified to be a tumor suppressor gene. Mutations of this gene are found to be expressed in the several tumor samples and in several cancer/tumor cell lines. Some of the mutations are alternatively or abnormally spliced forms. For example, in some of the alternatively spliced forms the central exons of the wild type transcript are found deleted (usually exons 5, 6, 7 and 8). Other mutations include hemizygous deletions of the WWOX locus that were identified in the vast majority of breast cancer lines analyzed (>80%). In addition, homozygous deletions were also found in coding and non-coding regions of the gene (i.e. intronic regions).

In one embodiment, the invention provides an isolated and purified polynucleotide comprising a nucleic acid sequence encoding a WWOX polypeptide. In another embodiment, the polynucleotide comprises a nucleic acid sequence encoding SEQ ID NO:2, SEQ ID NO:31, or SEQ ID NO:33. In yet another embodiment, the polynucleotide comprises SEQ ID NO:1, SEQ ID NO:30, or SEQ ID NO:32. It is contemplated that any other WWOX nucleic acid or protein sequence may be used in conjunction with this invention.

In one embodiment, the polynucleotide described above, comprises a nucleic acid sequence that encodes at least 90 contiguous amino acid residues of SEQ ID NO:2. In another embodiment the polynucleotide comprises a nucleic acid sequence encoding at least 150 contiguous amino acid residues of SEQ ID NO:2. In yet another embodiment, the polynucleotide comprises at least 1.5 contiguous kilobases of SEQ ID NO:1.

The invention also provides an expression vector comprising a nucleic acid sequence encoding a WWOX polypeptide. In one embodiment, the expression vector comprises the nucleic acid sequence encoding SEQ ID NO:2. In another embodiment, the expression vector comprises the nucleic acid sequence comprising SEQ ID NO:1. In yet other embodiments, the expression vector comprises the nucleic acid sequence comprising at least 1.5 contiguous kilobases of SEQ ID NO:1. In a related embodiment, the expression vector comprises a nucleic acid sequence encoding at least 90 contiguous amino acids of SEQ ID NO:2.

In further aspects of this embodiment of the invention, the expression vector further comprises a promoter operably linked to the WWOX-encoding nucleic acid sequence. In one related aspect, the promoter is heterologous. In another related aspect, the promoter is a constitutive promoter, a tissue-specific promoter, an inducible promoter, or a noninducible promoter.

In one embodiment, the expression vector is a viral vector. In a specific aspect of this embodiment, the viral vector is a vaccinia virus, adenovirus, herpesvirus, retrovirus, cytomegalovirus, or adeno-associated virus.

The invention also provides a recombinant host cell comprising a nucleic acid sequence encoding a WWOX polypeptide. In a specific aspect of this embodiment, the polypeptide comprises SEQ ID NO:2. In another specific aspect of this embodiment the nucleic acid sequence comprises SEQ ID NO:1.

The invention also provides several methods for preparing recombinant WWOX encoding polypeptides. Thus, in one embodiment a method of preparing recombinant WWOX is described that comprises: (a) transfecting a cell with a polynucleotide comprising a nucleic acid sequence encoding a WWOX polypeptide to produce a transformed host cell; and (b) maintaining the transformed host cell under biological conditions sufficient for expression of the WWOX polypeptide in the host cell. In a specific aspect of this method the nucleic acid sequence encodes SEQ ID NO:2. In another specific aspect of this method the nucleic acid sequence comprises SEQ ID NO:1. In a related embodiment of the method, the polynucleotide is comprised in a vector.

The invention also provides animal model studies which demonstrate the tumor suppressor properties of WWOX in vivo. In mice models of breast cancer, injection of vectors expressing WWOX supressed tumor growth in mice when compared to mice that were injected with control vectors. As the WWOX gene is a tumor suppressor gene with anticancer/antitumor properties, the inventors envision several therapeutic methods for anticancer therapies. Thus, the invention describes a method of treating a pre-cancer or cancer cell comprising providing to the cell an amount of a WWOX polypeptide effective to induce apoptosis in the cell. In one aspect of this method, the WWOX polypeptide is provided to the cell by administering an expression vector comprising a polynucleotide encoding a WWOX polypeptide under the transcriptional control of a promoter. In specific aspects of this method, the cell is a bladder, blood, bone, bone marrow, brain, breast, central nervous system, colon, esophagus, gastrointestine, head, kidney, liver, lung, nasopharynx, neck, ovary, prostate, skin, stomach, or uterus cell. In other specific embodiments of this method, the expression vector comprises a viral vector.

The invention also discloses a method of treating a subject having a hyperproliferative condition comprising contacting a cell within the subject with an expression vector comprising a polynucleotide encoding an WWOX polypeptide under the transcriptional control of a promoter, wherein expression of the WWOX polypeptide confers a therapeutic benefit on the subject. The term 'contacting' as used in this specification also includes administering, delivering and/or providing.

In one embodiment of the method, the cell is a cancer or pre-cancer cell. In a specific aspect of this embodiment, the cancer or pre-cancer cell is selected from a group consisting of a bladder, blood, bone, bone marrow, brain, breast, colon, esophagus, gastrointestine, head, kidney, liver, lung, nasopharynx, neck, ovary, prostate, skin, stomach, and uterus cell. In other aspects, the cancer or pre-cancer cell is derived from or is part of a solid tumor. In another embodiment of the method, the cell is involved with restenosis, primary psoriasis, angiogenesis, rheumatoid arthritis, inflammatory bowel disease, psoriasis, eczema, secondary cataracts, or bronchial dysplasia. In some embodiments of the method, the contacting occurs in vitro. In other embodiments, the contacting occurs in vivo. As described above the term 'contacting' as used in this specification also includes administering, delivering, and/or providing. In one embodiment of the method, the expression vector is delivered endoscopically, intravenously, intralesionally, percutaneously, or subcutaneously. In another embodiment, the expression vector is delivered by direct injection into the tumor. In yet other embodiments, the expression vector comprises a viral vector. In specific aspects of this embodiment, the viral vector is a vaccinia virus, adenovirus, herpesvirus, retrovirus, cytomegalovirus, or adeno-associated virus.

In one embodiment of this method, the contacting is performed at least twice. In other aspects of this embodiment, the second contacting follows the first by a period of about one day to one year.

The invention also contemplates methods for anticancer therapies wherein the therapies using WWOX encoding nucleic acids and or peptides are in combination or conjunction with other anticancer therapies. Thus, in one aspect the method described above further comprises contacting the tumor with an anticancer therapy. This anticancer treatment can be any one or more of the following: chemotherapy, immunotherapy, surgery, radiotherapy, gene therapy with a second therapeutic polynucleotide other than a polynucleotide encoding the WWOX polypeptide, or other biotherapy.

In further embodiments, chemotherapy involving at least one DNA damaging agent is implemented in combination with administration of an WWOX encoding nucleic acid molecule. The DNA damaging agent may be gamma-irradiation, X-rays, UV-irradiation, microwaves, electronic emissions, adriamycin, 5-fluorouracil (5FU), etoposide (VP-16), camptothecin, actinomycin-D, mitomycin C, cisplatin (CDDP), or hydrogen peroxide. In further embodiments, the DNA damaging agent is adriamycin. While in other embodiments, the chemotherapy comprises a cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, or methotrexate or any analog or derivative variant thereof. In one aspect of the invention, the chemotherapy comprises tamoxifen, while in another aspect is it comprises adriamycin. Further embodiments involve immunotherapy, such as Herceptin. In cases involving a cancerous tumor, a combination treatment may involve administration of a nucleic acid molecule encoding a WWOX polypeptide and tumor resection, which may occur before, after, or during the WWOX gene therapy administration. If WWOX treatment occurs after tumor resection, the expression construct or vector encoding WWOX may be administered to the tumor bed.

In yet other aspects of the method, the expression vector is contacted with the tumor prior to, at the same time as, or after contacting with the anticancer treatment.

In one embodiment, the method is used when the endogenous WWOX polypeptide of the cancer cell is mutated.

The invention also describes a method of treating a subject having pre-cancer or cancer comprising contacting a pre-cancer or cancer cell within the subject with an expression vector comprising a polynucleotide encoding WWOX polypeptide under the transcriptional control of a promoter, wherein expression of the WWOX polypeptide is at a level effective to kill the cell, thereby conferring a therapeutic benefit on the subject.

The invention further discloses a method of treating cancer in a cancer patient, comprising administering to a tumor site therapeutically effective amounts of an expression vector and an anticancer agent, wherein the expression vector comprises a polynucleotide encoding an WWOX polypeptide under the transcriptional control of a promoter, and wherein expression of the WWOX polypeptide and anticancer agent results in treatment of the cancer.

Yet another method described in the invention concerns arresting the cell cycle of a mammalian cancer cell comprising contacting the cell with an expression vector comprising a polynucleotide sequence encoding an WWOX polypeptide under the transcriptional control of a promoter, wherein expression of the WWOX polypeptide results in the cell cycle arrest of the cancer cell.

The invention also discloses another method for treating microscopic residual cancer comprising the steps of: (i) identifying a patient having a resectable tumor; (ii) resecting the tumor; and (iii) contacting the tumor bed with an expression vector comprising a promoter functional in eukaryotic cells and a polynucleotide encoding an WWOX polypeptide, wherein the polynucleotide is under the transcriptional control of a promoter.

The invention further describes a method for treating a subject having a tumor comprising the steps of: (i) surgically revealing the tumor; and (ii) contacting the tumor with an expression vector comprising a promoter functional in eukaryotic cells and a polynucleotide encoding an WWOX polypeptide, wherein the polynucleotide is under the transcriptional control of a promoter.

Yet another method described herein comprises a method for treating a subject having a tumor comprising the step of perfusing the tumor, over an extended period of time, with an expression vector comprising a promoter functional in eukaryotic cells and a polynucleotide encoding an WWOX polypeptide, wherein the polynucleotide is under the transcriptional control of a promoter.

In addition the invention describes a method of treating a subject having pre-cancer or cancer comprising administering a pre-cancer or cancer cell within the subject a first expression vector comprising a polynucleotide encoding an WWOX polypeptide under the transcriptional control of a promoter; and administering the pre-cancer or cancer cell within the subject a second expression vector comprising a polynucleotide encoding a wild-type tumor suppressor polypeptide under the transcriptional control of a promoter. In one aspect of this method, the first expression vector and the second expression vector are administered at the same time.

The invention also provides a method of killing a human cell comprising contacting the cell with an expression vector comprising a polynucleotide sequence encoding an WWOX polypeptide under the transcriptional control of a promoter, wherein expression of the WWOX polypeptide results in the killing of the cell.

A cancer includes diseases and conditions that are associated with any sort of abnormal cell growth or abnormal growth regulation. This includes but is not limited to tumors, precancerous lesions, pre-cancer cells, carcinomas, malignant cancers, microscopic residual cancers as some examples.

Nucleic acid molecules of the present invention may contain sequences encoding a full-length, human WWOX gene, as disclosed in SEQ ID NO:1. In some embodiments of the invention, a nucleic acid molecule may encode fewer nucleotides than is depicted in SEQ ID NO:1, such that the molecule contains fewer than 1245 contiguous nucleotides from SEQ ID NO:1. In some aspects, a nucleic acid molecule may contain about 50, 60, 70, 80, 85, 86, 87, 88, 89, 90, 100, 150, 200, 250, 300, 350, 400, 450, 500, 550, 600, 610, 617, 650, 675, 700, 750, 800, 850, 900, 950, 1000, 1050, 1100, 1150, 1200, 1210, 1220, 1230, 1240 contiguous nucleotides from SEQ ID NO:1. In additional aspects, specific coding fragments for functional domains of WWOX include two WW-domain coding regions, one of these is from nucleotide +55 to +142 (87 contiguous nucleotides from SEQ ID NO:1) and the other is +175 to +264 (89 contiguous nucleotides from SEQ ID NO:1) are contemplated. Furthermore, a short chain dehydrogenase domain encoded between nucleotides +373 and +990 (617 contiguous nucleotides from SEQ ID NO:1) are also contemplated as useful.

Proteins of the present invention may contain amino acids sequences for the full-length human WWOX protein, as disclosed in SEQ ID NO:2. In some embodiments of the invention, shorter polypeptides and peptides may be used. Such polypeptides and peptides can contains fewer than 414 contiguous amino acids of SEQ ID NO:2. In some aspects, these polypeptides and/or proteins may contain about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, to about 410 contiguous amino acids of SEQ ID NO:2. Polypeptides with intermediate lengths are also contemplated as useful. In addition, polypeptides encoding specific functional regions of the WWOX protein are also contemplated. Thus, polypeptides containing about 29 contiguous amino acids of SEQ ID NO:2 encoding the two WW-domains, one from amino acid number 18 to amino acid number 47 and another from amino acid number 59 to amino acid number 88 which are responsible for protein—protein interactions are also contemplated. Additionally a polypeptides containing 205 contiguous amino acids of SEQ ID NO:2 encoding a catalytic part of WWOX with homology to a family of short chain dehydrogenases (SDR) protein from amino acid number 125 to amino acid number 330 is also contemplated.

In embodiments describing expression constructs of WWOX suitable promoter and enhancer elements will be used. In some aspects the enhancers are 5' LTR enhancer sequences from retroviral vectors. However, another enhancer sequence may be used. In certain embodiments, the promoter is a 5' LTR promoter sequence from retroviral vectors, CMV IE, dectin-1, dectin-2, human CD11c, F4/80, SM22, RSV, SV40, Ad MLP, beta-actin, MHC class I or MHC class II promoter, however any other promoter that is useful to drive expression of the WWOX gene of the present invention, is believed to be applicable to the practice of the present invention. In other embodiments, a polyadenylation signal is operatively linked to a WWOX coding region.

In certain embodiments, the nucleic acid is a viral vector, wherein the viral vector dose is from about $10^3$, $10^4$, $10^5$, $10^6$, $10^7$, $10^8$, $10^9$, $10^{10}$, $10^{11}$, $10^{12}$, $10^{13}$ pfu and higher. Alternatively, dosage may be expressed in units of viral particles (vp); thus, the numbers listed above in "pfu" units may be expressed in units of "vp" units or "viral particles." It is contemplated that about $10^3$ to about $10^{15}$, about $10^5$ to about $10^{12}$, or $10^7$ to about $10^{10}$ viral particles may be administered to a patient.

The methods of the present invention include dispersing expression constructs, vectors, and cassettes in pharmacologically acceptable solution for administration to a patient. The pharmacologically acceptable solution can be a buffer, a solvent a diluent and may comprise a lipid. In one embodiment of the present invention, a nucleic acid molecule encoding a WWOX polypeptide is administered in a liposome. These nucleic acid molecules may be administered to the patient intravenously, intraperitoneally, intratracheally, intratumorally, intramuscularly, endoscopically, intralesionally, percutaneously, subcutaneously, regionally, or by direct injection or perfusion. It is further contemplated that treatment methods may involve multiple administrations.

The nucleic acid of the present invention may be administered by injection. Other embodiments include the administering of the nucleic acid by multiple injections. In certain embodiments, the injection is performed local, regional or distal to a disease or tumor site. In some embodiments, the administering of nucleic acid is via continuous infusion, intratumoral injection, or intravenous injection.

In another aspect, the invention provides methods for the detection and diagnosis of cancers. In a specific aspect, the type or subtype of cancer can be detected. One method comprises the generation of antibodies to different portions of the WWOX polypeptide and using these antibodies as biomarkers for the diagnosis of cancers. For example, some of the tumor specific alternatively spliced versions of WWOX have an open reading frame shift (such as the Δ5–8 form) which encodes for a protein with a different and longer carboxy terminus end. Specific antibodies will be generated to detect these tumor specific WWOX's alternative protein forms. Such antibodies would be useful as they recognize and distinguish the abnormal forms of WWOX even in the presence of the normal forms of the WWOX protein in the same specimen. These methods also allow the identification of tumor specific WWOX proteins in a cell that is suspected to be cancerous.

In addition, abnormal transcripts, such as the alternatively or abnormally spliced versions of WWOX, can also be identified on cDNA samples synthesized from tumor samples RNA by means of RT-PCR and employing deletion specific primers.

Yet another method comprises detection of changes in gene expression of the WWOX gene, such as increased or decreased gene expression, as an indicator of cancer.

The invention also provides methods for the prognosis of cancer using the WWOX gene. In one embodiment, the method comprises identification of the mutated version of the WWOX protein expressed by a cancerous cell. This identifies the exact cancer subtype and provides the prognosis.

Thus, the invention provides a method for detecting cancer comprising: (i) obtaining a sample; (ii) contacting the sample with an anti-WWOX antibody; and (iii) detecting the binding of the anti-WWOX-antibody to a WWOX polypeptide. A sample is defined herein as a cell, tissue, blood sample, cellular extract, biological fluid, serum/plasma, or a biopsy sample. The anti-WWOX antibody is specific for a mutated WWOX polypeptide.

The invention also provides a method for detecting the susceptibility of an individual to a certain cancer comprising: (i) obtaining DNA from an individual; (ii) obtaining probes specific to WWOX; and (iii) identifying a change in the WWOX gene and/or gene products. The DNA can be cDNA or genomic DNA such as, chromosomal DNA. The identifying may comprise amplification such as PCR-based amplification. The probes may in these embodiments encode nucleic acid primers. The change in the WWOX gene and/or gene products may be a mutation and/or an increase or decrease in the amount of a WWOX gene product. For example, alternatively or abnormally expressed WWOX transcripts were identified by PCR-based amplification in colonic adenocarcinoma cells, gastric adenocarcinoma cells, breast carcinoma cells and multiple myeloma cells. In the case of breast carcinomas, abnormal and alternatively expressed WWOX transcripts were also found to be expressed in primary breast tumor cells.

In embodiments of the method involving chromosomal DNA, the identifying comprises the technique of fluorescent in situ hybridization (FISH). The FISH probes encode nucleic acids spanning the WWOX chromosomal locus. The probes further comprise one or more fluorescent detection moieties. These methods can detect the susceptibility of individuals to different types of cancers, for example, multiple myeloma subtypes, breast cancers, colonic adenocarcinomas and gastric adenocarcinomas involving mutations in WWOX loci can be detected by these methods.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Sequence-tagged sites (STS) are ordered from centromere (left) to telomere (right). The relative distance between sequence-tagged site markers is arbitrary. The nomenclature used for the STSs derived from the ends of specific BACs indicates first the BAC clone address followed by S or T representing the SP6 or T7 (vector sequencing primers) end of the insert respectively. MM.1 and JJN3 indicate the relative position of translocation breakpoints observed in myelomas; t(14;16)(q32;q23). Based on the length of unordered contigs obtained from shotgun sequencing, the distance between markers 112B17S and 36O22T is ≧400 Kbp. (FIG. 1B) The isolated BACs and YACs are represented as horizontal lines; dashed vertical lines represent the position of STS markers in corresponding BACs and YACs. Size of clones are not to scale. There is only one gap in this BAC contig (between BACs 36O22 and 293D3). The homozygous deletion spanned from STS 249B4S to D16S3029 inclusive. (FIG. 1C) Black-filled rectangular blocks represent WWOX exons as numbered. The approximate position of each exon in each corresponding BAC clone is illustrated.

FIGS. 2A & 2B. (FIG. 2A) Predicted amino acid sequence of WWOX reveals two WW domains and a short chain dehydrogenase domain. WW domains are boxed and conserved tryptophans and prolines are shown in bold; note that in the second WW domain one tryptophan is replaced by a tyrosine (conservative change). The short chain dehydrogenase domain is underlined and the conserved residues YXXXK and S, characteristic of a substrate binding site, are highlighted; bases GXXXGXG, typical of a coenzyme binding site, are shown in bold italics (SEQ ID NO. 2). (FIG. 2B) Comparative alignment of the WW domains from WWOX vs. the Pfam WW domain prototypic amino acid sequence (SEQ ID NO. 69). In the consensus sequence, highly conserved amino acids are shown in upper-case. The middle line illustrates how well the WWOX sequence compares with the WW consensus; satisfactory replacements are represented by +. Numbering corresponds to WWOX amino acid sequence (SEQ ID NO. 70).

FIGS. 5A, 5B & 5C. (FIG. 5A) Ability of WWOX to suppress anchorage independent growth of MDA-MB-435 and T47D breast cancer cell lines transfected with expression vector carrying WWOX cDNA or transfected with control vector only in a soft agar growth assay. Comparative analysis on the number of colonies larger than 200 μm in diameter. Colonies were stained by incubation with nitro blue tetrazolium, complete culture fields were photographed, colony counting and measurements were performed using NIH Image analysis software. (FIG. 5B and FIG. C) Suppression of tumorigenesis of MDA-MB-435 breast cancer cells in nude mice by ectopically increased WWOX expression. Five animals per condition (i.e., cells transfected with vector alone or vector with the WWOX transgene) were injected bilaterally into the thoracic mammary fat pads with 1×10$^6$ cells per site. Tumor growth was monitored for 7 weeks and caliper measurements were conducted once per week. (FIG. 5B) Comparative analysis on the rate of tumor growth from cells transfected with vector alone or vector with WWOX. Tumor volumes were calculated as described in the section entitled Example 4. Note the clear difference in tumor latency and rate of tumor growth. (FIG. 5C) The top two rows display the tumors formed by the MDA-MB-435/vector cells innude mice at the end of the observation period. A total of 10 tumors out of 10 injection sites developed. The two bottom rows display the tumors that formed by MDA-MB-435 WWOX transfected cells at the end of the same observation period, 7 tumors out of 10 injection sites developed. Note the dramatic difference in size between both groups (P=0.00001).

DESCRIPTION OF ILLUSTRATIVE EMBODIMENTS

Figure 1:
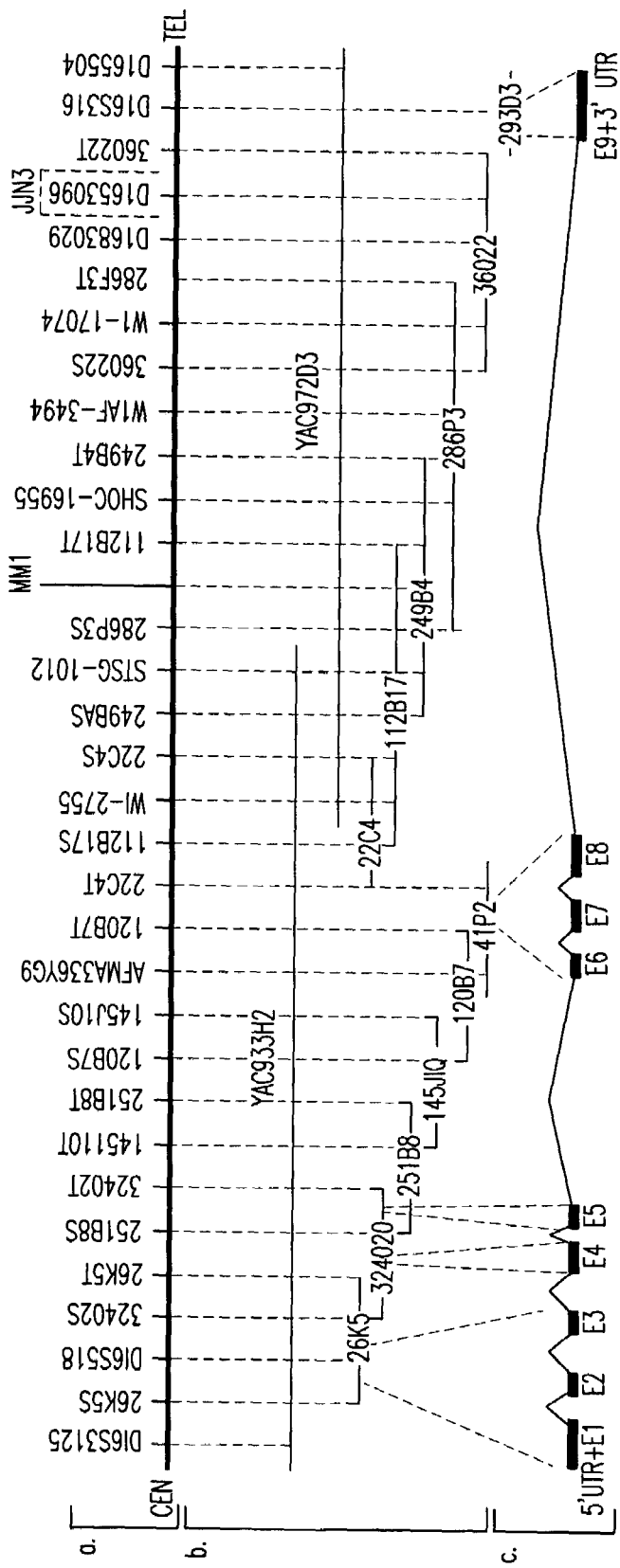
FIGS. 1A, 1B, & 1C. High-resolution physical map of the 16q23.3–24.1 chromosomal region containing WWOX.
Figure 3:
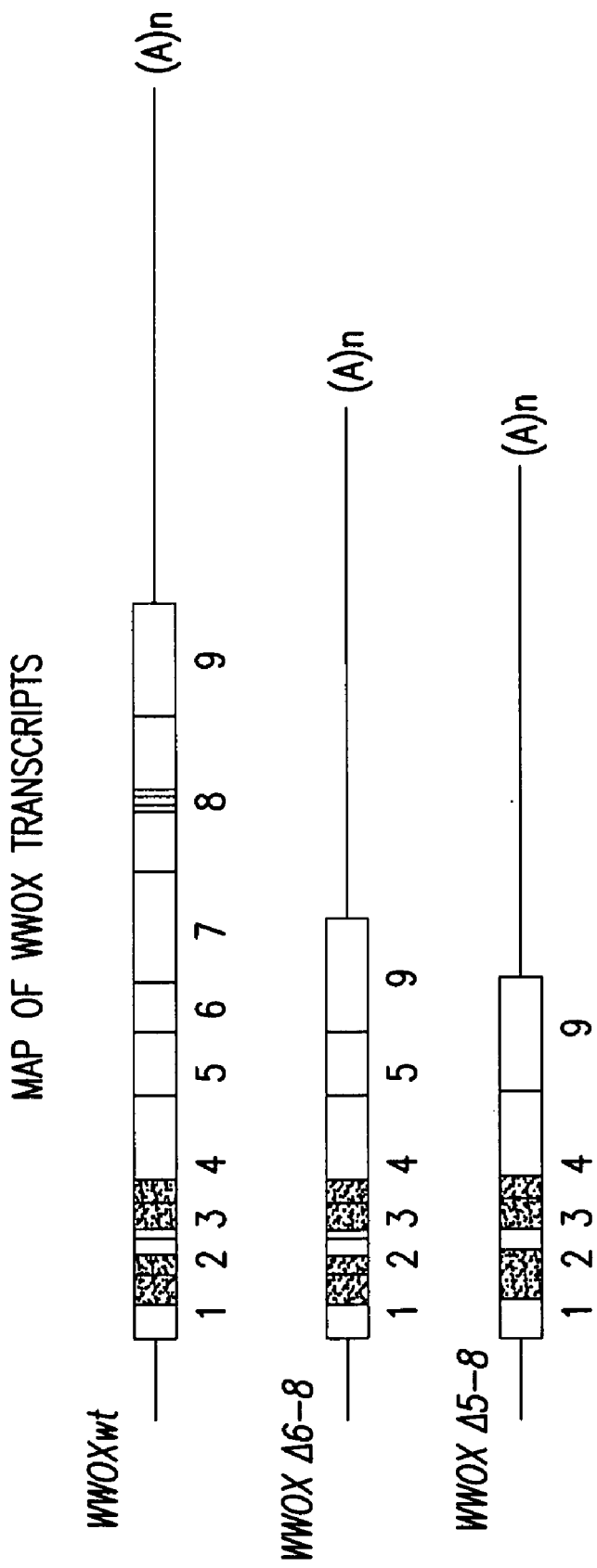
FIG. 3. Map of WWOX transcripts.

The present invention describes the identification of a novel gene, human WWOX, which has an open reading frame of 1245 bp and encodes a 414 amino-acid protein. The WWOX gene is composed of nine exons and was identified while mapping the chromosome region 16q23.3–24.1. The 16q23.3–24.1 region is an area commonly affected by allelic losses in breast cancer. The inventors generated a detailed physical map of the genomic region spanning between sequence-tagged site markers D16S518 and D16S516 and used shotgun genomic sequencing as well as isolation and analysis of transcripts mapping to this chromosomal region.

WWOX contains two WW domains coupled to a region with high homology to the short-chain dehydrogenase/reductase family of enzymes. WW domains are generally involved in interactions with other proteins (see below). The highest normal expression of WWOX is seen in hormonally regulated tissues such as testis, ovary, and prostate. This expression pattern and the presence of a short-chain dehydrogenase/reductase domain and specific amino acid features indicate a role for WWOX in steroid metabolism.

A mutation screening showed that mutations of the WWOX gene yield mutated WWOX protein products in various tumor samples and tumor lines. Abnormal versions of the WWOX transcript were also detected in tumor lines. Some of these mutations are abnormally or alternatively spliced versions of WWOX. For example, deletion of exons 6–8 (WWOX Δ6–8) was seen in cell lines MCF-7 and MDA-MB 453 (breast cancer cell lines); HCT116 (colon adenocarcinoma cell line); AGS (gastric adenocarcinoma cell line). Transcripts with deleted exons 5–8 (WWOX Δ5–8) were found in KMS11 a myeloma cell line. Other deletions were also found in following cell lines: JJN3 (myeloma cell line); MDA-MB157 and MDA-MB435 (breast cancer cell lines). In addition, expression studies show variable expression of WWOX in breast cancer cell lines as compared with normal breast cells and tissues. For example, some breast cancer cell lines show overexpression of WWOX transcripts while other breast cancer cell lines show little or no expression of WWOX.

Some of the abnormally or alternatively spliced WWOX forms found in cancer cell lines exhibit intact WW-domain regions but have a deleted enzymatic domain thus, representing non-functional forms of the protein. Since the protein—protein interaction domains are preserved in the abnormal forms these forms can act as dominant negative versions of the protein. In other words, the abnormal and enzymatically inactive forms compete with the wild type forms for binding with the WWOX binding partners. The kinetics of this alternative binding reaction may be preferred and thus the normal function of wild-type protein may be inhibited in cancer/tumor cells.

Since cancer is caused by mutations in genes that are responsible for cell-cycle control and cell growth, mutations or aberrant expression patterns of genes in normal versus cancer cells indicate their involvement in regulating the cell-cycle and growth. Abnormally expressed genes, which includes expression of mutant products including abnormally or alternatively spliced isoforms and changes in the level of gene expression, are indicators of the cancerous phenotype. The present inventors envision that the detection of such abnormal gene products in a biological sample obtained from a patient with a cancer can be effectively used for the detection and diagnosis of cancers. One can also obtain an indication on the specific type or subtype of cancer based on the species of abnormal gene products expressed. Therefore, the present invention provides methods for the detection, diagnosis, prognosis and the treatment of cancers using the WWOX nucleic acid and protein sequences.

Thus, the invention provides methods for identifying patients having abnormalities in the WWOX gene or its gene products. In some cases, the WWOX encoded proteins are mutated. In yet other cases, the amount of the expressed RNA and/or proteins are abnormal. For example, detecting an increase in gene expression of the WWOX gene is an indicator of cancer.

The invention also provides methods in which antibodies are generated to different portions of some WWOX polypeptides and used as biomarkers for the diagnosis of cancers. The WWOX polypeptides and/or epitopes thereof are those that are expressed in cancers as a result of mutations. The invention also provides methods to identify individuals susceptible to WWOX-associated hyperproliferative conditions. Such methods comprise generating fluorescent probes spanning the WWOX chromosomal locus to identify WWOX mutations. For example, fluorescent probes have been generated to identify multiple myeloma subtypes in individuals. Kits for the detecting cancers as well as kits for detecting individuals susceptible to cancers are also contemplated.

The present invention also provides in vitro and in vivo data that demonstrate the tumor supressor propoerties of WWOX. Ectopic expression of WWOX in breast cancer cell lines, mediated by transfecting recombinant retroviral constructs, inhibited the ability of the tumor cells to grow in soft agar. Reduced colony formation was observed in cancer cells expressing WWOX. In addition, in vivo studies using nude mice demonstrated that animals injected with vectors expressing WWOX had remarkably smaller tumors. For example, mice that were injected with a vector expressing WWOX had tumors with an average wet weight of 51±22 mg in dramatic contrast to mice that were injected with a control vector that had tumors with an average wet weight of 821±295 mg.

Therefore, the invention also provides methods for the treatment of cancer and hyperproliferative diseases by providing WWOX gene products. Nucleic acids encoding WWOX polypeptides and/or proteins can be provided as gene therapy to cells in need thereof as therapeutic and preventive treatments.

A. Cancer and WWOX

A variety of cancers including pre-cancers can be treated according to the methods of the present invention. Some of the cancer types contemplated for treatment in the present invention include breast, prostate, liver, myelomas, bladder, blood, bone, bone marrow, brain, colon, esophagus, gastrointestine, head, kidney, lung, nasopharynx, neck, ovary, skin, stomach, and uterus cancers are contemplated for treatment.

Cancer has become one of the leading causes of death in the western world, second only behind heart disease. Current estimates project that one person in three in the U.S. will develop cancer, and that one person in five will die from cancer. Cancers can be viewed as altered cells that have lost the normal growth-regulating mechanisms. Oncogenes are genes that control cell cycle and normal cell growth. Mutations in oncogenes therefore cause imbalances in cell cycle control and lead to cancers.

The WWOX gene was identified by the present inventors while mapping the chromosomal region 16q23.3–24.1. This region is an area that is affected by allelic losses in breast, liver and prostate carcinomas and by translocations in multiple myeloma. Furthermore, various epithelial tumors have chromosomal and genomic abnormalities affecting chromosome 16q. Homozygous deletions have been identified in the chromosome 16q area in various tumor cell lines: the AGS gastric adenocarcinoma cell line, the HCT116 colon adenocarcinoma cell line, the PEO4 ovarian adenocarcinoma cell line and the WX330 small cell lung carcinoma cell line (Paige et al., 2000; Manglesdorf et al., 2000). The WWOX gene identified in the present invention spans this entire region and is larger than 1 Mb in size. Furthermore, WWOX also spans the common fragile site FRA16D. Thus, WWOX is a prime target for genetic abnormalities affecting the common fragile site in the 16q arm. WWOX has been identified by the present inventors as a tumor suppressor gene and several cancer cells and cell lines express alternatively or abnormally spliced variants of the WWOX polypeptide.

WWOX has also been demonstrated to have strong tumor supressive properties in in vitro and in vivo studies. Inhibition of cancer cell growth and colony formation was seen in breast cancer cell lines that were transfected with recombinant retroviral constructs that resulted in ectopic expression of WWOX. More importantly, in vivo studies using nude mice have demonstrated that animals injected with vectors expressing WWOX have significantly smaller tumors. For example, mice that were injected with a vector expressing WWOX had tumors with an average wet weight of 51±22 mg in dramatic contrast to mice that were injected with a control vector that had tumors with an average wet weight of 821±295 mg.

The present invention therefore provides methods that involve a WWOX polypeptide or a WWOX polypeptide-encoding nucleic acid to treat patients with cancers where WWOX nucleic acids and/or proteins and/or polypeptides are involved, such that these patients are conferred a therapeutic benefit as a result of the treatment. By involvement, the WWOX encoding nucleic acid and/or protein and/or polypeptide may be mutated and/or abnormal and/or the overexpression of this gene and/or polypeptide may also suffice to cause the cancer. The term "therapeutic benefit" used herein refers to anything that promotes or enhances the well-being of the patient with respect to the medical treatment of the patient's cancer. A list of nonexhaustive examples of this includes extension of the patient's life by any period of time; decrease or delay in the neoplastic development of the disease; decrease in hyperproliferation; reduction in tumor growth; delay or prevention of metastases; reduction in the proliferation rate of a cancer cell or tumor cell; induction of apoptosis in any treated cell or in any cell affected by a treated cell; induction of cell killing; a decrease in cell growth; and/or a decrease in pain to the patient that can be attributed to the patient's condition.

In many contexts, it is not necessary that the cell be killed or induced to undergo normal cell death or "apoptosis." Rather, to accomplish a meaningful treatment, all that is required is that the cancer/tumor growth be slowed to some degree. It may be that the cell's growth is completely blocked, however, or that some tumor regression is achieved. Clinical terms such as "remission" and "reduction of tumor" also are contemplated given their normal usage.

B. Other Hyperproliferative Conditions and WWOX

The present invention also provides methods for the treatment of hyperproliferative conditions other than cancer and preneoplastic conditions. The types of conditions that may be treated, according to the present invention, are limited only by the involvement of WWOX. By involvement, it is not even a requirement that WWOX be mutated or abnormal. The overexpression, mislocalization, or abnormal processing of this polypeptide may also suffice to cause a hyperproliferative state. The hyperproliferative conditions include conditions such as but not limited to restenosis, primary psoriasis, angiogenesis, rheumatoid arthritis, inflammatory bowel disease, psoriasis, eczema, secondary cataracts, or bronchial dysplasia. Thus, the administration of a WWOX polypeptide or a WWOX polypeptide encoding nucleic acid to treat patients with hyperproliferative conditions confers a therapeutic benefit as a result of the treatment.

The term "therapeutic benefit" used herein refers to anything that promotes or enhances the well-being of the subject with respect to the medical treatment of his condition, which includes treatment of hyperproliferative conditions. A list of nonexhaustive examples of this includes extension of the subject's life by any period of time, decrease in hyperproliferation, a decrease in pain or symptoms of the subject that can be attributed to the subject's condition.

C. The WW Domain

The WW domain is a small functional domain that is characterized by two tryptophan residues, one in the amino terminal portion of the WW domain and one in the carboxyl terminal portion, and is found in a large number of proteins from a variety of species including humans, nematodes, and yeast. WW domains are 30 to 40 amino acids in length, which make them much smaller than typical functional domains, most of which are from 50 to about 150 residues long. WW domains are often flanked by stretches of amino acids rich in histidine or cysteine and these stretches might be metal-binding sites. The center of WW domains is hydrophobic although the remainder of the domain bears a number of charged residues. These features are characteristic of functional domains involved in protein—protein interactions (Bork and Sudol, 1994).

Andre and Springael, 1994, proposed the following consensus sequence for WW domains:

$WX_7 G(K/R)X_1 (Y/F)(Y/F)X_1 (N/D)X_2 (T/S)(K/R)$
$X_1 (T/S)(T/Q/S)WX_2 P$ where X represents any amino acid and bold letters represent highly conserved amino acids. They also proposed that WW domains led them to conclude that WW domains lack α-helical content and possess a central β-strand region flanked by unstructured regions. Other studies predict a structure of β-strands containing charged residues flanking a hydrophobic core composed of four aromatic residues (Chen and Sudol, 1995, and references cited therein).

The WW domain has been found in a wide variety of proteins of varying function. However, most proteins containing WW domains are predominantly involved in either cell signaling and growth regulation or in the organization of the cytoskeleton. For example, the WW domain-containing protein dystrophin belongs to a family of cytoskeletal proteins that includes α-actinin and β-spectrin. Mutations in dystrophin are responsible for Duchenne and Becker muscular dystrophies. The dystrophin gene gives rise to a family of alternatively spliced transcripts. The longest of these encodes a protein having four domains: (1) a globular, actin-binding region; (2) 24 spectrin-like repeats; (3) a cysteine-rich $Ca^{2+}$ binding region; and (4) a carboxyl terminal globular region. A short stretch of the dystrophin protein, after the spectrin-like repeats and before the $Ca^{2+}$ binding region, β-dystroglycan. This suggests that WW domains may be involved in protein—protein interactions (Bork and Sudol, 1994).

Another example is YAP, a protein that was discovered by virtue of its binding to the SH3 domain of the proto-oncogene Yes (Sudol, 1994). Murine YAP was found to have two WW domains and chicken and human YAP each have only a single WW domain (Sudol, et al., 1995). Chen and Sudol, 1995, screened a cDNA expression library with bacterially produced glutathione S-transferase fusion proteins of the WW domain from YAP. They identified and isolated two proteins from the library (WBP-1 and WBP-2) that specifically bound the YAP WW domain. Comparison of the amino acid sequences of WBP-1 and WBP-2 revealed a homologous proline-rich region in each protein. The proline-rich regions contained the shared motif PPPPY. Chen and Sudol then showed that as few as ten residues containing this motif conferred upon a fusion protein the ability to specifically bind the YAP WW domain. This binding was highly specific; the motif bound to the YAP WW domain but not to the WW domain from dystrophin or to a panel of SH3 domains.

Nedd4 is another protein which possesses three WW domains. In mouse, Nedd4 seems to play a role in embryonic development and the differentiation of the central nervous system (Kumar et al., 1992).

Among other proteins having WW domains, the rat transcription factor FE65 possesses an amino terminal activation region that includes a WW domain (Bork and Sudol, 1994). A yeast protein, ess1, contains a WW domain and is thought to be involved in cytokinesis and/or cell separation (Hanes et al., 1989). The human protein kiaa93 has 4 WW domains and may be the human version of mouse Nedd4 (Hoffman and Bucher, 1995). The human protein HUMORF1, although of unknown function, has a roughly 350 amino acid region, which is homologous to GTPase-activating proteins (Andre and Springael, 1994).

D. WWOX Nucleic Acids and Uses Thereof

One embodiment of the present invention is to transfer nucleic acids encoding a WWOX polypeptide to induce the destruction of cancers including precancers and/or hyperproliferative conditions. In one embodiment the nucleic acids encode a full-length, substantially full-length, or functional equivalent form of a WWOX protein. In other embodiments the WWOX is human WWOX.

Thus, in some embodiments of the present invention, the treatment of cancer involves the administration of a therapeutic nucleic acid expression construct encoding a WWOX polypeptide to a cancer cell. It is contemplated that the cancer cells take up the construct and express the therapeutic polypeptide encoded by nucleic acid, thereby restoring a growth control to the cancer cells.

Certain aspects of the present invention concern at least one WWOX nucleic acid molecule. In certain aspects, the WWOX nucleic acid comprises a wild-type or mutant WWOX nucleic acid. In particular aspects, the WWOX nucleic acid encodes for at least one transcribed nucleic acid. In particular aspects, the WWOX nucleic acid encodes at least one WWOX protein, polypeptide, or peptide, or biologically functional equivalent thereof. In other aspects, the WWOX nucleic acid comprises at least one nucleic acid segment of SEQ ID NO:1, SEQ ID NO:30, SEQ ID NO:32, or at least one biologically functional equivalent thereof. SEQ ID NO:30 and SEQ ID NO:32 represent alternatively spliced versions. In yet other aspects, the WWOX nucleic acid comprises a nucleic acid sequence which encodes at least 90 contiguous amino acid residues of SEQ ID NO:2. In still other aspects, the WWOX nucleic acid comprises a nucleic acid sequence encoding at least 150 contiguous amino acid residues of SEQ ID NO:2. Thus, the WWOX nucleic acid can comprise a nucleic acid sequence encoding 90, 91, 92, 93, 94, 95, 96, 97, 98, 99, 100, 101, 105, 110, 115, 120, 125, 130, 135, 140, 145, 150, 160, 165, 170, 175, 180, 185, 190, 200, 250, 300, 350, 400, 410, or 414 amino acids. In another aspect, the WWOX nucleic acid comprises at least 1.5 contiguous kilobases of SEQ ID NO:1. In some aspects the WWOX nucleic acid is a human WWOX nucleic acid.

The present invention also concerns the isolation or creation of at least one recombinant construct or at least one recombinant host cell through the application of recombinant nucleic acid technology known to those of skill in the art or as described herein. The recombinant construct or host cell may comprise at least one WWOX nucleic acid, and may express at least one WWOX protein, polypeptide, or peptide, or at least one biologically functional equivalent thereof.

In some embodiments the invention refers to DNA sequences identified by Database Accession numbers: GenBank AF211943, AF212843, AF179633, AF395124, AF395123.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e., two or more alleles exist) at a genetic locus in the individuals of a population. As used herein, "mutant" refers to a change in the sequence of a nucleic acid or its encoded protein, polypeptide, or peptide that is the result of recombinant DNA technology.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,683,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a WWOX nucleic acid, and/or encodes a WWOX polypeptide or peptide-coding sequences. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues that encode a portion of the full-length WWOX polypeptide. For example, a truncated gene may not contain the nucleic acid sequence for the N-terminal region of the WWOX polypeptide. It is envisioned that the nucleic acid sequences of the present invention may contain fewer than 95% of the contiguous nucleic acid residues of SEQ ID NO:1, SEQ ID NO:30, or SEQ ID NO:32. Alternatively, these sequences may comprise fewer than 90%, 85%, 80%, 75%, or 70% of the contiguous nucleic acid residues of SEQ ID NO:1 SEQ ID NO:30, or SEQ ID NO:32.

"Isolated substantially away from other coding sequences" means that the gene of interest, in this case the WWOX gene, forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by recombinant nucleic acid technology.

In certain embodiments, the nucleic acid is a nucleic acid segment. As used herein, the term "nucleic acid segment," are smaller fragments of a nucleic acid, such as for non-limiting example, those that encode only part of the WWOX peptide or polypeptide sequence. Thus, a "nucleic acid segment may comprise any part of the WWOX gene sequence, of from about 2 nucleotides to the full-length of the WWOX peptide- or polypeptide-encoding region. In certain embodiments, the "nucleic acid segment" encompasses the full-length WWOX gene sequence. In particular embodiments, the nucleic acid comprises any part of SEQ ID NO:1, SEQ ID NO:30, or SEQ ID NO:32, of from about 2 nucleotides to the full-length of the sequence encoding SEQ ID NO:2, SEQ ID NO:31, or SEQ ID NO:33.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to SEQ ID NO:1. Such a stretch of nucleotides, or a nucleic acid construct, may be or be about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 480, about 880, about 890, about 900, about 910, about 920, about 930, about 940, about 950, about 960, about 970, about 980, about 990, about 1,000, about 1010, about 1020, about 1030, about 1040, about 1050, about 1060, about 1070, about 1080, about 1090, about 1,100, about 1110, about 1120, about 1130, about 1140, about 1150, about 1160, about 1170, about 1180, about 1190, about 1200, 1210, about 1220, about 1230, about 1240, to about 1245 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the given values (i.e., all integers including and between such values).

It is further understood that a nucleic acid sequence encoding all or a portion of an WWOX polypeptide may be comprised of contiguous complementary or identical nucleic acid sequences of any of the lengths described above and from SEQ ID NO:1, SEQ ID NO:30, or SEQ ID NO:32.

It is contemplated that the nucleic acid constructs of the present invention may encode a full-length WWOX or encode a truncated version of WWOX, such that the transcript of the coding region represents the truncated version.

The term "a sequence essentially as set forth in SEQ ID NO:1, or SEQ ID NO:30, or SEQ ID NO:32" or "a sequence essentially as set forth in SEQ ID NO:1, or SEQ ID NO:30, or SEQ ID NO:32" means that the sequence substantially corresponds to a portion of SEQ ID NO:1, or SEQ ID NO:30, or SEQ ID NO:32, and has relatively few amino acids that are not identical to, or biologically functionally equivalent to, the amino acids of SEQ ID NO:2, or SEQ ID NO:31, or SEQ ID NO:33.

a. Oligonucleotide Probes and Primers

Naturally, the present invention also encompasses DNA segments that are complementary, or essentially complementary, to the sequence set forth in SEQ ID NO:1, or SEQ ID NO:30, or SEQ ID NO:32. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, or SEQ ID NO:30, or SEQ ID NO:32 under relatively stringent conditions such as those described herein. Such sequences may encode the entire WWOX protein or fragments thereof.

The nucleic acid detection techniques and conditions described herein serve both to define the functionally equivalent nucleic acids of the invention, as outlined structurally above, and to describe certain methods by which the cancer marker gene sequences and their equivalents may be used in practical terms to identify and characterize cancer cells and tissues.

Hybridizing fragments should be of sufficient length to provide specific hybridization to a RNA or DNA tissue sample. The use of a hybridization probe of between about 10–14 or 15–20 and about 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800, 900, 1000, 1100, 1200 and longer are contemplated as well. Such oligonucleotides will find use, for example, as probes in Southern and Northern blots and as primers in amplification reactions.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C.

One method of using probes and primers of the present invention is in the search for genes related to WWOX or, more particularly, homologs of WWOX from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected.

In certain embodiments, one may desire to employ a fluorescent label, electroluminescence or an enzyme tag such as urease, alkaline phosphatase or peroxidase, instead of radioactive or other environmentally undesirable reagents. In the case of enzyme tags, calorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions.

The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

b. Vectors and Regulatory Signals

Vectors of the present invention are designed, primarily, to transform cancer cells with a therapeutic WWOX gene under the control of regulated eukaryotic promoters (i.e., constitutive, inducible, repressable, tissue-specific). Also, the vectors may contain a selectable marker if, for no other reason, to facilitate their manipulation in vitro. However, selectable markers may play an important role in producing recombinant cells.

Tables 1 and 2, below, list a variety of regulatory signals for use according to the present invention.

TABLE 1

Inducible Elements

| Element | Inducer | References |
|---|---|---|
| MT II | Phorbol Ester (TFA) Heavy metals | Palmiter et al., 1982; Haslinger and Karin ®, 1985; Searle et al., 1985; Stuart et al., 1985; Imagawa et al., 1987; Karin , 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | E1A | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TFA) | Angel et al., 1987b |
| Murine MX Gene | Interferon, Newcastle Disease Virus | Hug et a., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |

TABLE 1-continued

Inducible Elements

| Element | Inducer | References |
|---|---|---|
| HSP70 | E1A, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | PMA | Hensel et al., 1989 |
| Thyroid Stimulating Hormone α Gene | Thyroid Hormone | Chatterjee et al., 1989 |

TABLE 2

Other Promoter/Enhancer Elements

| Promoter/Enhancer | References |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| γ-Globin | Bodine and Ley, 1987; Perez-Stable and Constantini, 1990 |
| β-Globin | Trudel and Constantini, 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_1$-antitrypsin | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |

TABLE 2-continued

Other Promoter/Enhancer Elements

| Promoter/Enhancer | References |
|---|---|
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present invention includes constitutive, inducible, and tissue-specific promoters.

The term "promoter" will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

One promoter that may be used in the present invention is the cytomegalovirus (CMV) promoter. This promoter is commercially available from Invitrogen in the vector pcDNAIII, which is preferred for use in the present invention. Also contemplated as useful in the present invention are the dectin-1 and dectin-2 promoters. Additional viral promoters, cellular promoters/enhancers and inducible promoters/enhancers that could be used in combination with the present invention are listed in Tables 2 and 3. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest. Alternatively, a tissue-specific promoter for cancer gene therapy (Table 3) or the targeting of tumors (Table 4) may be employed with the nucleic acid molecules of the present invention.

TABLE 3

Candidate tissue-specific promoters for cancer gene therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40–50% of gastric carcinomas; most pancreatic carcinomas; many breast carcinomas | Colonic mucosa; gastric mucosa; lung epithelia; eccrine sweat glands; cells in testes |

TABLE 3-continued

Candidate tissue-specific promoters for cancer gene therapy

| Tissue-specific promoter | Cancers in which promoter is active | Normal cells in which promoter is active |
|---|---|---|
| Prostate-specific antigen (PSA)** | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) cells | Many lung adenocarcinomas | Type II pneumocytes; Clara |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast, and in respiratory gastrointestinal, and, genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrncytes, Schwann cells; some neurons |
| Keratin 14 | Presumably many squamous cell carcinomas (eg: Head and neck cancers) | Keratinocytes |
| EBV LD-2 | Many squamous cell carcinomas of head and neck | Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 4

Candidate promoters for use with a tissue-specific targeting of tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas; keratinocytes; possibly many other cancers | Activated leukocytes: neurons; endothelial cells; cells in immunoprivileged tissues; some cells in lungs, ovaries, liver, and prostate |
| Myc-regulated promoter | Most lung carcinomas (both small cell and non-small cell); most epithelial colorectal carcinomas | Proliferating cells (only some cell-types): mammary cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/ BiP | Presumably many different cancers, since GRP7S expression is induced by tumor-specific conditions | Cells at sites of ischemia |
| CArG elements from Egr-1 | Induced by ionization radiation, so conceivably most tumors upon irradiation | Cells exposed to ionizing radiation; leukocytes |

A signal that may prove useful is a polyadenylation signal (hGH, BGH, SV40). The use of internal ribo some binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgene constructs of the present invention are functionally positioned downstream of a promoter element.

C. Gene Transfer i. Viral Transformation a) Adenoviral Infection

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and et al., 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

Recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

In nature, adenovirus can package approximately 105% of the wild-type genome (Ghosh-Choudhury et al., 1987), providing capacity for about 2 extra kb of DNA. Helper cell lines derived from human cells such as human embryonic kidney cells, muscle cells, hematopoietic cells or other human embryonic mesenchymal or epithelial cells may be used to make the construct. Alternatively, the helper cells may be derived from the cells of other mammalian species that are permissive for human adenovirus. Such cells include, e.g., Vero cells or other monkey embryonic mesenchymal or epithelial cells.

The adenovirus vector may be replication defective, or at least conditionally defective, the nature of the adenovirus vector is not believed to be crucial to the successful practice of the invention. The adenovirus may be of any of the 42 different known serotypes or subgroups A–F.

Adenovirus growth and manipulation is known to those of skill in the art, and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus et al., 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b) Retroviral Infection

A preferred method for delivery of the recombinant DNA in the present invention involves the use of an retroviral expression vector. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et 1988; Hersdorffer et al., 1990).

c) AAV Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

d) Other Viral Vectors

Other viral vectors may be employed as constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material.

In still further embodiments of the present invention, the nucleic acid encoding human WWOX is housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. Such modifications permit specific infection of cancer and/or hyperproliferative cells via specific receptors present on these cells.

For example, targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

ii. Non-Viral Delivery

In addition to viral delivery of the nucleic acid encoding full length or truncated WWOX protein, the following are additional methods of recombinant gene delivery to a given host cell and are thus considered in the present invention.

a) Electroporation

In certain preferred embodiments of the present invention, the gene construct is introduced into target hyperproliferative cells via electroporation. Electroporation involves the exposure of cells (or tissues) and DNA (or a DNA complex) to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for hyperproliferative cells from different sources may be optimized. One may particularly wish to optimize such parameters as the voltage, the capacitance, the time and the electroporation media composition. The execution of other routine adjustments will be known to those of skill in the art.

b) Particle Bombardment

Another embodiment of the invention for transferring a naked DNA construct into cells involves particle bombardment. This method depends on the ability to accelerate DNA-coated microprojectiles to a high velocity allowing them to pierce cell membranes and enter cells without killing them (Klein et 1987). The microprojectiles used have consisted of biologically inert substances such as tungsten, platinum, or gold beads.

It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force (Yang et al., 1990). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. Recently, results from a clinical trial evaluating utility of this delivery system for vaccination was published. The study was designed to determine the safety and immunogenicity of a DNA vaccine consisting of a plasmid encoding hepatitis B surface antigen delivered by the PowderJect XR1 gene delivery system into human skin (Tacket et al., 1999).

Accordingly, it is contemplated that one may wish to adjust various bombardment parameters in small scale studies to fully optimize the conditions. One may particularly wish to adjust physical parameters such as gap distance, flight distance, tissue distance and helium pressure. One also may optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

c) Calcium Phosphate Co-Precipitation or DEAE-Dextran Treatment

In other embodiments of the present invention, the transgenic construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

d) Direct Microinjection or Sonication Loading

Further embodiments of the present invention include the introduction of the nucleic acid construct by direct microinjection or sonication loading. Direct microinjection has been used to introduce nucleic acid constructs into *Xenopus* oocytes (Harland and Weintraub, 1985), and LTK⁻ fibroblasts have been transfected with the thymidine kinase gene by sonication loading (Fechheimer et al., 1987).

e) Lipid-Mediated Transformation

In a further embodiment of the invention, the gene construct may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987) and in vivo gene transfer (Zhu et al., 1993; Solodin et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydrationrehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1996). Numerous disease treatments are using lipid based gene transfer strategies to enhance conventional or establish novel therapies, in particular therapies for treating cancers.

In certain embodiments of the invention, the lipid vehicle may be complexed with a hemagglutinating virus (HVJ). This has been shown to facilitate fusion with the cell membrane and promote cell entry of lipid-encapsulated DNA (Kaneda et al., 1989). In other embodiments, the lipid vehicle may be complexed or employed in conjunction with nuclear non-histone chromosomal proteins (HMG-1) (Kato et al., 1991). In yet further embodiments, the lipid vehicle may be complexed or employed in conjunction with both HVJ and HMG-1.

E. WWOX Protein, Polypeptides, and Peptides

The invention contemplates the use of a WWOX polypeptide in the treatment of cancers. In some embodiments a full-length or a substantially full-length WWOX polypeptide may be used. The term "full-length" refers to a WWOX polypeptide that contains at least the 414 amino acids encoded by the WWOX cDNA. The term "substantially full-length" in the context of WWOX refers to a WWOX polypeptide that contains at least 80% of the contiguous amino acids of the full-length WWOX polypeptide. However, it is also contemplated that WWOX polypeptides containing at least about 85%, 90%, and 95% of SEQ ID NO:2, or SEQ ID NO:31, or SEQ ID NO:33, are within the scope of the invention as "substantially full-length" WWOX. In other embodiments the WWOX polypeptide comprises at least 90 contiguous amino acid residues of SEQ ID NO:2. In still other aspects, the WWOX polypeptide comprises at least 150 contiguous amino acid residues of SEQ ID NO:2

Some embodiments contemplate the attachment of a heterologous signal sequence to the WWOX polypeptide to make it secreted.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids of SEQ ID NO:2, or SEQ ID NO:31, or SEQ ID NO:33, will be a sequence that is "essentially as set forth in SEQ ID NO:2, or SEQ ID NO:31, or SEQ ID NO:33" provided the biological activity of the protein, polypeptide, or peptide is maintained.

The term "functionally equivalent codon" is used herein to refer to codons that encode the same amino acid, such as the six codons for arginine and serine, and also refers to codons that encode biologically equivalent amino acids (see Table 5).

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NO:1, or SEQ ID NO:30, or SEQ ID NO:32, will be nucleic acid sequences that are "essentially as set forth in SEQ ID NO:1, or SEQ ID NO:30, or SEQ ID NO:32." It will also be understood that this invention is not limited to the particular nucleic acid and amino acid sequences of SEQ ID NO:1, or SEQ ID NO:30, or SEQ ID NO:32, and SEQ ID NO:2, or SEQ ID NO:31, or SEQ ID NO:33, respectively. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent WWOX proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Recombinant changes may be introduced, for example, through the application of site-directed mutagenesis techniques as discussed herein below, e.g., to introduce improvements or alterations to the antigenicity of the protein, polypeptide or peptide, or to test mutants in order to examine WWOX protein, polypeptide, or peptide activity at the molecular level.

Fusion proteins, polypeptides or peptides may be prepared, e.g., where the WWOX coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively.

TABLE 5

CODON TABLE

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 5 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of WWOX, but with altered and even improved characteristics.

(a) Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

(b) Protein Purification

It may be desirable to purify WWOX or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Antibodies a. Antibody Generation

A "WWOX-antigen" is defined herein as mutated WWOX peptide(s) or polypeptide(s) and/or those WWOX polypeptides or proteins that are expressed in higher concentrations that are expressed in cancers or hyperproliferative states involving WWOX. Polyclonal or monoclonal antibodies specific for such WWOX-antigens have utilities in several applications. These include the production of diagnostic kits for use in detecting and diagnosing cancer. An additional use is to link such antibodies to therapeutic agents, such as chemotherapeutic agents, and to administer the antibodies to individuals with cancer, thereby selectively targeting the cancer cells for destruction.

Means for preparing and characterizing antibodies are well known in the art (See, e.g., Antibodies: A Laboratory Manual, Cold Spring Harbor Laboratory, 1988; incorporated herein by reference). Antibodies to WWOX peptides or protein may be generated using such standard techniques.

Briefly, a polyclonal antibody is prepared by immunizing an animal with an immunogenic composition in accordance with the present invention and collecting antisera from that immunized animal. A wide range of animal species can be used for the production of antisera such as, a rabbit, a mouse, a rat, a hamster, a guinea pig or a goat.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and tittering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified WWOX protein, polypeptide or peptide. The immunizing composition is administered in a manner effective to stimulate antibody producing cells. Rodents such as mice and rats are preferred animals, however, the use of rabbit, sheep, goat, monkey cells also is possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Selection of the hybridoma secreting the Mab of choice is performed by culturing the cells in selective media such as HAT and individual clonal supernatants are tested (after about two to three weeks) for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones can then be propagated indefinitely to provide MAbs.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

b. Antibody Conjugates

Antibody conjugates in which a WWOX antibody is linked to a detectable label or a cytotoxic agent form further aspects of the invention. Diagnostic antibody conjugates may be used both in vitro diagnostics, as in a variety of immunoassays, and in vivo diagnostics, such as in imaging technology.

Certain antibody conjugates include those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

c. Antibodies for use In Vitro also may be Radiolabeled Antibody Conjugates

In using an antibody-based molecule as an in vivo diagnostic agent to provide an image of, for example, breast, gastric, colon, pancreas, renal, ovarian, lung, prostate, hepatic, and lung cancer or respective metastases, magnetic resonance imaging, X-ray imaging, computerized emission tomography and such technologies may be employed. In the antibody-imaging constructs of the invention, the antibody portion used will generally bind to a WWOX polypeptide, used as a cancer marker, and the imaging agent will be an agent detectable upon imaging, such as a paramagnetic, radioactive or fluorescent agent.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies also may be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA).

Fluorescent labels include rhodamine, fluorescein isothiocyanate and renographin.

d. Immunotoxins

The invention further provides immunotoxins in which an antibody that binds to a mutated WWOX peptide or polypeptide that is expressed in a cancer or hyperproliferative state, i.e., a WWOX-antigen, is linked to a cytotoxic agent. Immunotoxin technology is fairly well-advanced and known to those of skill in the art. Immunotoxins are agents in which the antibody component is linked to another agent, particularly a cytotoxic or otherwise anticellular agent, having the ability to kill or suppress the growth or cell division of cells.

As used herein, the terms "toxin" and "toxic moiety" are employed to refer to any cytotoxic or otherwise anticellular agent that has such a killing or suppressive property. Toxins are thus pharmacologic agents that can be conjugated to an antibody and delivered in an active form to a cell, wherein they will exert a significant deleterious effect.

The preparation of immunotoxins is, in general, well known in the art (see, e.g., U.S. Pat. No. 4,340,535, incorporated herein by reference). It also is known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restirictocin, a ribonuclease, diphtheria toxin or pseudomonas exotoxin, to mention just a few examples. The use of toxin-antibody constructs is well known in the art of immunotoxins, as is their attachment to antibodies. Of course, combinations of the various toxins could also be coupled to one antibody molecule, thereby accommodating variable or even enhanced cytotoxicity.

One type of toxin for attachment to antibodies is ricin, with deglycosylated ricin A chain being particularly preferred. As used herein, the term "ricin" is intended to refer to ricin prepared from both natural sources and by recombinant means. Various 'recombinant' or 'genetically engineered' forms of the ricin molecule are known to those of skill in the art, all of which may be employed in accordance with the present invention.

Linking or coupling one or more toxin moieties to an antibody may be achieved by a variety of mechanisms, for example, covalent binding, affinity binding, intercalation, coordinate binding and complexation. Covalent binding methods use chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will generally desire to prepare it into a pharmaceutical composition that may be administered parenterally. This is done by using for the last purification step a medium with a suitable pharmaceutical composition. Such formulations will typically include pharmaceutical buffers, along with excipients, stabilizing agents and such like. The pharmaceutically acceptable compositions will be sterile, non-immunogenic and non-pyrogenic. Details of their preparation are well known in the art and are further described herein. It will be appreciated that endotoxin contamination should be kept minimally at a safe level, for example, less that 0.5 ng/mg protein.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

G. Immunological Detection a. Immunoassays

The anti-WWOX antibodies, directed to WWOX proteins, and/or polypeptides expressed in cancers, are useful in various diagnostic and prognostic applications connected with the detection and analysis of cancer. The WWOX proteins, and/or polypeptides include mutated versions of WWOX as well as those WWOX forms that are expressed in higher concentrations in cancers and hyperproliferative states involving WWOX.

In still further embodiments, the present invention thus concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the presence of the WWOX proteins including mutated, altered and increased levels.

The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a sample suspected of containing a WWOX-antigen as defined above, or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a cancer involving WWOX such as a breast, gastric, colon, pancreas, myeloma, renal, ovarian, lung, prostate, hepatic, lung, lymph node, brain, uterus or bone marrow tissue section or specimen, a homogenized tissue extract, an isolated cell, a cell membrane preparation, separated or purified forms of any of the above protein-containing compositions, or even any biological fluid that comes into contact with cancer tissues, including blood, lymphatic fluid, seminal fluid and urine.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present, such as WWOX encoded antigens. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of cancer. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

b. ELISAs

As noted, it is contemplated that the WWOX proteins or peptides of the invention, will find utility in ELISAs. For example, ELISAs can be used to detect the presence of mutated/abnormal versions of WWOX proteins in cancer cells, using antibodies specific for those abnormal WWOX proteins. Thus, one can detect cancer in a cell and it may be further possible to detect the specific sub-type of the cancer depending on which abnormal WWOX protein is expressed.

In one exemplary ELISA, antibodies binding to the encoded proteins of the invention are immobilized onto a selected surface exhibiting protein affinity, such as a well in a polystyrene microtiter plate. Then, a test composition suspected of containing the cancer disease marker antigen, e.g., a WWOX protein/polypeptide expressed in cancer cells, such as a clinical sample, is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA". Detection also may be achieved by the addition of a second antibody, followed by the addition of a third antibody that has binding affinity for the second antibody, with the third antibody being linked to a detectable label.

In another exemplary ELISA, the samples suspected of containing a WWOX polypeptide/protein are immobilized onto the well surface and then contacted with the antibodies of the invention. After binding and washing to remove non-specifically bound immunecomplexes, the bound antibody is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the a WWOX polypeptide/protein is immobilized, involves the use of antibody competition in the detection. In this ELISA, labeled antibodies are added to the wells, allowed to bind to the WWOX-antigen, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

In other embodiments, solution-phase competition ELISA is also contemplated. Solution phase ELISA involves attachment of a WWOX polypeptide/protein to a bead, for example a magnetic bead. The bead is then incubated with sera from human and animal origin. After a suitable incubation period to allow for specific interactions to occur, the beads are washed. The specific type of antibody is the detected with an antibody indicator conjugate. The beads are washed and sorted. This complex is the read on an appropriate instrument (fluorescent, electroluminescent, spectrophotometer, depending on the conjugating moiety). The level of antibody binding can thus by quantitated and is directly related to the amount of signal present.

c. Immunohistochemistry

The antibodies to the WWOX-antigens as defined above also may be used in conjunction with both fresh-frozen and formalin-fixed, paraffin-embedded tissue blocks prepared from study by immunohistochemistry (IHC). For example, each tissue block consists of 50 mg of residual "pulverized" tumor. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" tumor at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

d. FACS Analyses

Fluorescent activated cell sorting, flow cytometry or flow microfluorometry provides the means of scanning individual cells for the presence of an antigen, such as a WWOX polypeptide/protein. The method employs instrumentation that is capable of activating, and detecting the excitation emissions of labeled cells in a liquid medium.

FACS is unique in its ability to provide a rapid, reliable, quantitative, and multiparameter analysis on either living or fixed cells. The cancer antibodies of the present invention provide a useful tool for the analysis and quantitation of antigenic cancer markers of individual cells.

Cells would generally be obtained by biopsy, single cell suspension in blood or culture. FACS analyses would probably be most useful when desiring to analyze a number of cancer antigens at a given time, e.g., to follow an antigen profile during disease progression.

e. In Vivo Imaging

The invention also provides in vivo methods of imaging cancer using antibody conjugates. The term "in vivo imaging" refers to any non-invasive method that permits the detection of a labeled antibody, or fragment thereof, that specifically binds to cancer cells located in the body of an animal or human subject.

The imaging methods generally involve administering to an animal or subject an imaging-effective amount of a detectably-labeled cancer-specific antibody or fragment thereof (in a pharmaceutically effective carrier), such as a WWOX antibody, and then detecting the binding of the labeled antibody to the cancerous tissue. The detectable label is preferably a spin-labeled molecule or a radioactive isotope that is detectable by non-invasive methods.

An "imaging effective amount" is an amount of a detectably-labeled antibody, or fragment thereof, that when administered is sufficient to enable later detection of binding of the antibody or fragment to cancer tissue. The effective amount of the antibody-marker conjugate is allowed sufficient time to come into contact with reactive antigens that be present within the tissues of the patient, and the patient is then exposed to a detection device to identify the detectable marker.

Antibody conjugates or constructs for imaging thus have the ability to provide an image of the tumor, for example, through magnetic resonance imaging, x-ray imaging, computerized emission tomography and the like. Elements particularly useful in Magnetic Resonance Imaging ("MRI") include the nuclear magnetic spin-resonance isotopes $^{157}Gd$, $^{55}Mn$, $^{162}Dy$, $^{52}Cr$, and $^{56}Fe$, with gadolinium often being preferred. Radioactive substances, such as technicium$^{99m}$ or indium$^{111}$, that may be detected using a gamma scintillation camera or detector, also may be used. Further examples of metallic ions suitable for use in this invention are $^{123}I$, $^{131}I$, $^{131}I$, $^{97}Ru$, $^{67}Cu$, $^{67}Ga$, $^{125}I$, $^{68}Ga$, $^{72}As$, $^{89}Zr$, and $^{201}Tl$.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA).

Administration of the labeled antibody may be local or systemic and accomplished intravenously, intra-arterially, via the spinal fluid or the like. Administration also may be intradermal or intracavitary, depending upon the body site under examination. After a sufficient time has lapsed for the labeled antibody or fragment to bind to the diseased tissue, in this case cancer tissue, for example 30 min to 48 h, the area of the subject under investigation is then examined by the imaging technique. MRI, SPECT, planar scintillation imaging and other emerging imaging techniques may all be used.

The distribution of the bound radioactive isotope and its increase or decrease with time is monitored and recorded. By comparing the results with data obtained from studies of clinically normal individuals, the presence and extent of the diseased tissue can be determined.

The exact imaging protocol will necessarily vary depending upon factors specific to the patient, and depending upon the body site under examination, method of administration, type of label used and the like. The determination of specific procedures is, however, routine to the skilled artisan. Although dosages for imaging embodiments are dependent upon the age and weight of patient, a one time dose of about 0.1 to about 20 mg, more preferably, about 1.0 to about 2.0 mg of antibody-conjugate per patient is contemplated to be useful.

H. Combination Cancer Therapies

A wide variety of cancer therapies, known to one of skill in the art, may be used in combination with the anticancer peptides and nucleotides of the present invention. Thus, in order to increase the effectiveness of the anticancer therapy using a WWOX polypeptide, or expression construct coding therefor, it may be desirable to combine these compositions with other agents effective in the treatment of cancer such as but not limited to those described below.

For example, one can use radiation therapy followed by gene therapy with the WWOX-encoding nucleic acids. Alternatively, one can use the WWOX-based anti-cancer therapy in conduction with surgery and/or chemotherapy, and/or immunotherapy, and/or other genetherapy, and/or local heat therapy. Thus, one can use one or several of the standard cancer therapies existing in the art in addition with the WWOX-based therapies of the present invention. All other non-WWOX based cancer therapies are refereed to herein as 'other cancer therapies.'

The other cancer therapy may precede or follow the WWOX-based therapy by intervals ranging from minutes to days to weeks. In embodiments where the other cancer therapy and the WWOX-based therapy are administered together, one would generally ensure that a significant period of time did not expire between the time of each delivery. In such instances, it is contemplated that one would administer to a patient both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the other cancer therapy and the WWOX-based therapy will be required to achieve complete cancer cure. Various combinations may be employed, where the other cancer therapy is "A" and the WWOX-based therapy treatment is "B", as exemplified below:

A/B/A B/A/B B/B/A A/A/B B/A/A A/A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations also are contemplated.

In addition, the WWOX-based therapy can be administered to a patient in conjunction with other therapeutic methods such as for example standard AIDS treatments. The exact dosages and regimens can be suitable altered by those of ordinary skill in the art.

a) Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

b) Surgery

Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy, such as with WWOX nucleic acids or peptides. Such treatment may be repeated, for example, every 1, 2, 3, 4, 5, 6, or 7 days, or every 1,2, 3,4, and 5 weeks or every 1, 2, 3, 4, 5, 6, 7, 8, 9, 10, 11, or 12 months. These treatments may be of varying dosages as well.

c) Chemotherapeutic Agents

Agents that affect DNA function are defined as chemotherapeutic agents, for example, agents that directly cross-link DNA, agents that intercalate into DNA, and agents that lead to chromosomal and mitotic aberrations by affecting nucleic acid synthesis. Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), or any analog or derivative variant of the foregoing.

d) Immunotherapy

Immunotherapeutics, generally, rely on the use of immune effector cells and molecules to target and destroy cancer cells. The immune effector may be, for example, an antibody specific for some marker on the surface of a tumor cell. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. WWOX gene transfer to cancer cells causes cell death and apoptosis. The apoptotic cancer cells are scavenged by reticuloendothelial cells including dendritic cells and macrophages and presented to the immune system to generate anti-tumor immunity (Rovere et al., 1999; Steinman et al., 1999). Immune stimulating molecules may be provided as immune therapy: for example, cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with WWOX will enhance anti-tumor effects. This one may use (i) Passive Immunotherapy which includes: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow; and/or (ii) Active Immunotherapy wherein an antigenic peptide, polypeptide or protein, or an autologous or allogenic tumor cell composition or "vaccine" is administered, generally with a distinct bacterial adjuvant (Ravindranath & Morton, 1991) and/or (iii) Adoptive Immunotherapy wherein the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

(e) Gene Therapy

In yet another embodiment, the other treatment is a secondary gene therapy in which a second therapeutic polynucleotide is administered before, after, or at the same time a first therapeutic polynucleotide encoding a WWOX polypeptide. Delivery of a vector encoding a WWOX polypeptide in conjuction with a second vector encoding one of the following gene products will have a combined anti-hyperproliferative effect on target tissues. Alternatively, a single vector encoding both genes may be used. A variety of proteins are encompassed within the invention, some of which are described below. Table 6 lists various genes that may be targeted for gene therapy of some form in combination with the present invention.

TABLE 6

Oncogenes

| Gene | Source | Human Disease | Function |
|---|---|---|---|
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis virus; ALV promoter insertion; amplified human tumors | Amplified, deleted squamous cell cancer; glioblastoma | EGF/TGF-α/ Amphiregulin/ Hetacellulin receptor |
| ERBB-2/NEU /HER-2 | Transfected from rat Glioblastomas | Amplified breast, ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoieis |
| TRK | Transfection from human colon cancer | | NGF (nerve growth Factor) receptor |
| MET | Transfection from human osteosarcoma | | Scatter factor/HGF Receptor |

TABLE 6-continued

Oncogenes

| Gene | Source | Human Disease | Function |
|---|---|---|---|
| RET | Translocations and point mutations | Sporadic thyroid cancer; familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like transcription factor)/ PDGF receptor gene Fusion |
| TGF-β receptor | | Colon carcinoma mismatch mutation target | |

NONRECEPTOR TYROSINE KINASES

| ABL | Abelson Mul.V | Chronic myelogenous leukemia translocation with BCR | Interact with RB, RNA polymerase, CRK, CBL |
|---|---|---|---|
| FPS/FES | Avian Fujinami SV;GA FeSV | | |
| LCK | Mul.V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |

SER/THR PROTEIN KINASES

| AKT | AKT8 murine retrovirus | | Regulated by PI(3)K?; regulate 70-kd S6 k? |
|---|---|---|---|
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |

MISCELLANEOUS CELL SURFACE[1]

| APC | Tumor suppressor | Colon cancer | Interacts with catenins |
|---|---|---|---|
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophilia* homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALL | Signaling? |

MISCELLANEOUS SIGNALING

| BCL-2 | Translocation | B-cell lymphoma | Apoptosis |
|---|---|---|---|
| CBL | Mu Cas NS-1 V | | Tyrosine-Phosphorylated RING finger interact Abl |
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |

GUANINE NUCLEOTIDE EXCHANGERS AND BINDING PROTEINS

| BCR | | Translocated with ABL in CML | Exchanger; protein Kinase |
|---|---|---|---|
| DBL | Transfection | | Exchanger |
| GSP | | | |

TABLE 6-continued

Oncogenes

| Gene | Source | Human Disease | Function |
| --- | --- | --- | --- |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |

NUCLEAR PROTEINS AND TRANSCRIPTION FACTORS

| Gene | Source | Human Disease | Function |
| --- | --- | --- | --- |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |

CELL CYCLE/DNA DAMAGE RESPONSE[10–21]

| Gene | Source | Human Disease | Function |
| --- | --- | --- | --- |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (pre-disposition leukemia | |
| MDA-7 | Fragile site 3p14.2 | Lung carcinoma | Histidine triad-related diadenosine 5',3''''-tetraphosphate asymmetric hydrolase |
| hMLI/MutL | | HNPCC | Mismatch repair; MutL Homologue |
| hMSH2/MutS | | HNPCC | Mismatch repair; MutS Homologue |

TABLE 6-continued

Oncogenes

| Gene | Source | Human Disease | Function |
|---|---|---|---|
| hPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger |

(i) Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

(ii) Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Nobori et al., 1995; Orlow et al., 1994). Restoration of wild-type p16$^{INK4}$ function by transfection with a plasmid expression vector reduced colony formation by some human cancer cell lines (Okamoto, 1994).

Other genes that may be employed as secondary gene therapies in conduction with the genetherapy of the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC.

(iii) Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., Bcl$_{XL}$, Bcl$_W$, Bcl$_S$, Mcl-1, A1, Bfl-1) or counteract Bcl-2 function and promote cell death (e.g., Bax, Bak, Bik, Bim, Bid, Bad, Harakiri).

(f) Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. In other embodiments, cytostatic or differentiation agents can be used in combination with the present invention to improve the anti-hyerproliferative efficacy of the treatments.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

I. WWOX-Based Therapies and Pharmaceuticals a. Protein Therapy of WWOX

Another therapy approach is the provision, to a subject, of WWOX polypeptide, active fragments, synthetic peptides, mimetics or other analogs thereof. The protein may be produced by recombinant expression means or, if small enough, generated by an automated peptide synthesizer. Formulations would be selected based on the route of administration and purpose including but not limited to liposomal formulations and classic pharmaceutical preparations.

b. Genetic-Based Therapies with WWOX

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing a WWOX polypeptide to that cell. Because the sequence homology between the human, mouse, rat, rabbit, murine, primate and dog genes, any of these nucleic acids could be used in human therapy, as could any of the gene sequence variants which would encode the same, or a biologically equivalent polypeptide. The lengthy discussion above of expression vectors and the genetic elements employed therein is incorporated into this section by reference. Particularly preferred expression vectors are viral vectors.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100–1000, or up to $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass, or solid tumor, may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

The method of treating cancer includes treatment of a tumor as well as treatment of the region near or around the tumor. In this application, the term "residual tumor site" indicates an area that is adjacent to a tumor. This area may include body cavities in which the tumor lies, as well as cells and tissue that are next to the tumor.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way WWOX-based genetherapy may be utilized according to the present invention.

In some embodiments of the present invention a subject is exposed to a viral vector and the subject is then monitored for expression construct-based toxicity, where such toxicity may include, among other things, causing a condition that is injurious to the subject.

c. Pharmaceutical Formulations and Delivery

In a preferred embodiment of the present invention, a method of treatment for a cancer by the delivery of an expression construct encoding a WWOX polypeptide is contemplated. Cancers that are most likely to be treated in the present invention are those that result from mutations in the WWOX gene and/or the altered expression of the WWOX gene products in the cancer cells. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, preneoplastic lesions in the lung, colon cancer, melanoma or bladder cancer.

Additionally, the invention also provides WWOX-based therapies for hyperproliferative conditions such as but not limited to restenosis, primary psoriasis, angiogenesis, rheumatoid arthritis, inflammatory bowel disease, psoriasis, eczema, secondary cataracts, or bronchial dysplasia.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

Preferably, patients will have adequate bone marrow function (defined as a peripheral absolute granulocyte count of $>2,000/mm^3$ and a platelet count of $100,000/mm^3$), adequate liver function (bilirubin <1.5 mg/dl) and adequate renal function (creatinine <1.5 mg/dl).

(i) Administration

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the therapeutic expression construct. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

Intratumoral injection, or injection into the tumor vasculature is specifically contemplated for discrete, solid, accessible tumors. Local, regional or systemic administration also may be appropriate. For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a WWOX polypeptide or an WWOX-polypeptide-encoding nucleic acid construct. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100–1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

(ii) Injectable Compositions and Formulations

One method for the delivery of an expression construct encoding a WWOX polypeptide to hyperproliferative cells in the present invention is via intratumoral injection. However, the pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vaccuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

J. Detection of WWOX

In some embodiments of the present invention, the detection of WWOX polynucleotides or polypeptides is desirable, for example, to determine the level of expression from an expression construct that contains an WWOX polynucleotide encoding an WWOX polypeptide and/or for detecting which truncated WWOX products are expressed in a cancer cell. Methods of detecting polynucleotides, such as the mRNA transcripts encoded by the WWOX polynucleotide of the expression construct, include Northern detection methods and nucleic acid amplification methods, such as the polymerase chain reaction (PCR) described in detail in U.S. Pat. Nos. 4,683,195, 4,683,202 and 4,800,159. Such techniques are known to those of ordinary skill in the art. Various methods of detecting polypeptides are also within the ordinary skill of those in the art. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. The basic ELISA technique and its variations are known to those of skill in the art. Assays for the presence of expression of WWOX may be performed directly on tissue samples. Methods for in vitro situ analysis are well known and involve assessing binding of antigen-specific antibodies to tissues, cells, or cell extracts. These are conventional techniques well within the grasp of those skilled in the art.

K. Kits

The materials and reagents required for detecting a cancer cell based on the expression of WWOX gene products may be assembled together in a kit. In one embodiment, such a kit generally will comprise anti-WWOX antibodies; and reagents to detect the formation of an antigen-antibody complex. In one embodiment, the anti-WWOX antibodies may be antibodies to mutated versions of the WWOX protein.

The materials and reagents required for detecting an individual prone to certain cancer types, based on mutations of the WWOX, may also be assembled together in a kit. Such a kit will generally comprise reagents to isolate chromosomal DNA from cells; a set of fluorescent probes spanning the WWOX gene locus; and reagents to detect the binding of these probes to mutated regions of the genome. The fluorophore may comprise: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In each case, the kits will preferably comprise distinct containers for each individual reagent; antibody type; and probe. Each biological agent will generally be suitable aliquoted in their respective containers. The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

In further embodiments, the invention provides immunological kits for use in detecting cancer cells, e.g., in biological samples. Such kits will generally comprise one or more antibodies that have immunospecificity for the mutated and abnormal proteins or peptides encoded by the WWOX gene in cancer cells. The antibodies will be specific for the abnormal versions of WWOX such as, the Δ5–8 form of WWOX, which is a frameshifted version that expresses a different protein from the normal WWOX. Thus, such antibodies can be used to identify cancer cells by using immunohistochemical methods such as ELISA's.

As the anti-WWOX proteins or peptide antibodies may be employed to detect cancer cells either or both of such components may be provided in the kit. The immunodetection kits will thus comprise, in suitable container means, a WWOX polypeptide/protein, a first antibody that binds to such a protein or peptide, and an immunodetection reagent.

In certain embodiments, the abnormal WWOX proteins or peptides, or the first antibody that binds to the protein or peptide, such as an anti-WWOX antibody as described above, may be bound to a solid support, such as a column matrix or well of a microtitre plate.

The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen.

Further suitable immunodetection reagents for use in the present kits include the two-component reagent that comprises a secondary antibody that has binding affinity for the first antibody or antigen (generally a anti-WWOX or a WWOX antigen), along with a third antibody that has binding affinity for the second antibody, wherein the third antibody is linked to a detectable label.

As noted above in the discussion of antibody conjugates, a number of exemplary labels are known in the art and all such labels may be employed in connection with the present invention. Radiolabels, nuclear magnetic spin-resonance isotopes, fluorescent labels and enzyme tags capable of generating a colored product upon contact with an appropriate substrate are suitable examples.

The kits may contain antibody-label conjugates either in fully conjugated form, in the form of intermediates, or as separate moieties to be conjugated by the user of the kit.

The kits may further comprise a suitably aliquoted composition of a WWOX protein or polypeptide, whether labeled or unlabeled, as may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

Additional embodiments provide RT-PCR-based kits which utilize primers specific for the tumor specific abnormal transcripts. As abnormally and/or alternatively spliced transcripts of WWOX are expressed in tumor cells detection of these abnormal transcripts is indicative of the presence of cancer. It is envisioned that human tissue samples will be screened for the presence of abnormal WWOX gene products to identify the cancer. Such samples could consist of cells, cellular fluid, needle biopsy cores, surgical resection samples, lymph node tissue, serum/plasma or any biological fluid.

In one example of such a kit a common 5' primer such as, 5'-AGGCAGTGCGCAGGCGTGAGC-3' (SEQ ID NO:14) and 3' specific primers spanning the new exon—exon junctions found only in the abnormal alternatively spliced forms such as, the abnormal or truncated forms of WWOX, will be provided in the kit. Some 3' specific primers contemplated are:

useful in monitoring the effectiveness of a treatment regimen. In any event, the methods of the present invention will assist physicians in diagnosing cancer and in determining optimal treatment courses for individuals with tumors of varying malignancy.

In other embodiments the prognosis comprises determining the susceptibility of individuals to certain WWOX dependent cancers. In one aspect this comprises 1) generating fluorescent probes spanning the WWOX chromosomal locus; 2) obtaining chromosomal DNA samples from individuals and 3) identifying different mutations of the WWOX gene, thereby identifying individuals susceptible to a particular cancer types.

As described herein in detail, the amount of a WWOX transcript and/or protein and/or polypeptide present within a biological sample, such as a tissue, blood or serum sample, may be determined by means of a molecular biological assay to determine the level of a nucleic acid that encodes such a polypeptide, or by means of an immunoassay to determine the level of the polypeptide itself.

It is envisioned that in clinical applications, human tissue samples will be screened for the presence of the WWOX gene products identified as markers of cancer herein. Such samples could consist of needle biopsy cores, surgical resection samples, lymph node tissue, or serum/plasma.

In certain embodiments, nucleic acids would be extracted from these samples and amplified as described above. Some embodiments would utilize kits containing pre-selected primer pairs or hybridization probes. The amplified nucleic acids would be tested for the markers by any of the detection methods described herein or other suitable methods known in the art.

In other embodiments, tissue extracts containing marker proteins would be extracted from a sample and subjected to an immunoassay as described herein. Immunoassays of tissue sections are also possible. Kits containing the antibodies of the invention would be useful.

```
A8:     5'-ACGGTGGTGGCAGCTCCCTGTTGCGATGG-3';        (SEQ ID NO:4)

A7-8:    5'-ACGGTGGTGGCAGCTCCCTGTTGACATTCTTGG-3';    (SEQ ID NO.5)

A6-8:     5'-ACGGTGGTGGCAGCTCCCTGTTGCCATTCTTC-3';    (SEQ ID NO:6)

A5-8:   5'-ACGGTGGTGGCAGCTCCCTGTTGCTATTCC-3'        (SEQ ID NO:7)

A4-8:    5'-TGGTGGCAGCTCCCTGTTGTCAACAAAAAACAC-3'    (SEQ ID NO:8)

A3-8:   5'-ACGGTGGTGGCAGCTCCCTGTTGCTCC-3'           (SEQ ID NO:9)

A2-8:   5'-ACGGTGGTGGCAGCTCCCTGTTGTTG-3'            (SEQ ID NO:3)
```

Thus, the RT-PCR-based kits will contain in suitable containers the appropriate primers, the enzymes required for reverse transcription and PCR, and other suitable buffers and reagents.

L. Prognostic Applications

Mutations and overexpression of the WWOX gene and its products was identified in a variety of cancer cells and cell lines. Thus, the WWOX encoded gene products are useful as markers for a cancer phenotype. Evaluation of the expression of WWOX in the cancer tissues of a patient will be useful in determining whether that patient's cancer will progress and, therefore, will allow a proper determination of the need for additional therapy to be made.

The expression levels of WWOX as well as the type of truncated or otherwise mutated WWOX protein will also be M. Screening for Modulators of WWOX As the WWOX polypeptides are mainly implicated in protein—protein interactions, either via the WW domain, and/or the SDR domain, and/or via other domains, another objective of the present invention is to provide methods for identifying molecules that interact with WWOX polypeptides. These molecules include proteins, peptides, polypeptides, oligopeptides, and/or any other molecule that can bind to and modulate the function and/or localization of a WWOX polypeptide.

The screening assays may comprise random screening of large libraries of candidate substances; alternatively, the assays may be used to focus on particular classes of compounds selected with an eye towards structural attributes that are believed to make them more likely to modulate the function and/or localization of WWOX. Modulators of WWOX polypeptides are also referred to as 'binding partners' in this specification.

By function, it is meant that one may assay for a change in the tumor suppressive ability of a WWOX polypeptide. For example, binding to or interaction with a modulator may inhibit the tumor suppressive ability of WWOX. Alternatively, modulators that increase the tumor suppressive properties of WWOX may be identified by the screening methods provided herein.

By localization, it is meant that one may assay for the cellular localization of WWOX. Normal wild-type WWOX localizes in the cytoplasm. However, the present inventors have shown that some aberrant or alternatively spliced WWOX polypeptides that are expressed in cancer cells localize to the Golgi bodies. WWOX-localization assays are described later in the section entitled 'Examples' and utilize WWOX proteins fused with fluorescent proteins such as the green fluorescent protein (GFP).

In some embodiments, the present inventors have identifies several binding partners of WWOX using far-Western blot analysis in conjunction with GST-fusion constructs of the WW domains of WWOX polypeptides. Some of the binding partners identified include proline rich oligopeptides such as Ld10, P3, CDC25 and WBP1 which have the proline rich motifs PPLP, PPR, PLT*P and PPPY respectively.

Other methods may also be used to identify a WWOX modulator. These methods will generally comprise determining the function of WWOX in the presence and absence of the candidate substance. A modulator is defined as any substance that alters function. For example, a method generally comprises:
(a) providing a candidate modulator;
(b) admixing the candidate modulator to a cell expressing WWOX or a suitable experimental animal expressing WWOX;
(c) measuring one or more characteristics cell or animal in step (c); and
(d) comparing the characteristic measured in step (c) with the characteristic of the cell or animal in the absence of said candidate modulator,
wherein a difference between the measured characteristics indicates that said candidate modulator is, indeed, a modulator of WWOX.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially inhibit or enhance WWOX activity or cause a change in the cellular localization of a WWOX polypeptide. The candidate substance may be a protein or fragment thereof, a small molecule, or even a nucleic acid molecule. It may prove to be the case that the most useful pharmacological compounds will be compounds that can bind to domains of WWOX polypeptides. This includes molecules with proline rich motifs which are known to interact with WW domains as well as other smaller ligands and/or co-factors that may bind to the SDR domain of WWOX polypeptides. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on a WWOX polypeptide. Regardless of the type of inhibitor or activator identified by the present screening methods, the effect of the inhibition or activation results in a change in the activity or localization of WWOX as compared to that observed in the absence of the added candidate substance.

2. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge—charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

3. In Cyto Assays

The present invention also contemplates the screening of compounds for their ability to modulate WWOX function/activity or localization in cells. Various cell lines can be utilized for such screening assays, including cells specifically engineered for this purpose. For example, one may use cancer cell lines that express alternatively spliced or aberrant WWOX polypeptides to screen for modulators that bind to these polypeptides and cause a decrease in the overall tumor suppression of WWOX. One can also used normal cells (i.e., non-cancerous cells), and screen for molecules that bind and regulate the function of wild-type WWOX.

Depending on the assay, a cell culture method may be required. The cell or cells are examined using any of a number of different physiologic assays. Such assays are known to the skilled artisan. Alternatively, molecular analysis may be performed, for example, looking at protein expression, mRNA expression (including differential display of whole cell or polyA RNA) and others.

4. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators of WWOX may be conducted using an animal model derived from any of these species.

In such assays, one or more candidate substances are administered to an animal, and the ability of the candidate substance(s) to alter one or more characteristics that relate to WWOX function, as compared to a similar animal not treated with the candidate substance(s), identifies a modulator. The characteristics may be any of those discussed above with regard to the function of a WWOX polypeptide including ability to suppress tumor formation.

The present invention provides methods of screening for a candidate substance that modulate the function of WWOX. In these embodiments, the present invention is directed to a method for determining the ability of a candidate substance to modulate the tumor suppressive properties of a WWOX polypeptide, generally including the steps of:

a) administering a candidate substance to the animal; and
b) determining the ability of the candidate substance to reduce one or more characteristics relating to WWOX function.

For example, a animal tumor model of cancer may be treated with a candidate substance in conjunction with a WWOX-based nucleic acid or protein therapy as discussed in this invention and the ability of the candidate substance to modulate the tumor suppressive properties of WWOX may be analyzed. Thus, enhancers and inhibitors of WWOX-function may be identified.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratumoral, intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an tumor site or tumor vasculature.

Determining the effectiveness of a compound in vivo may involve a variety of different criteria. Also, measuring toxicity and dose response can be performed in animals in a more meaningful fashion than in in vitro or in cyto assays.

N. Screening for Anti-Tumor Activity Using Animal Models

Animal models may be used as a screen for tumor suppressive effects of the WWOX gene or gene combinations. Preferably, orthotopic animal models will be used so as to closely mimic the particular disease type being studied and to provide the most relevant results.

One type of orthotopic model involves the development of an animal model for the analysis of microscopic residual carcinomas and microscopic seeding of body cavities. "Carcinoma," as used herein, may refer to a single cell or a multicellular tumor mass. In microscopic disease, the "tumor" will consist or one or a few carcinoma cells which cannot be observed with the naked eye. The animal model described herein is particularly advantageous mimicking (i) the post surgical environment of head and neck cancer patients, particularly in advanced stages of disease and (ii) the body cavity of an affected subject wherein microscopic carcinoma has been established. The model, similar to other animal models for cancer, derives from inoculation of tumor cells into an animal. A distinction, however, lies in the creation, subcutaneously, of a pouch that is a physiologic equivalent of a natural body cavity or a post-surgical cavity created by the excision of a tumor mass.

Virtually any animal may be employed, however, for use according to the present invention. Particularly preferred animals will be small mammals that are routinely used in laboratory protocols. Even more preferred animals will be those of the rodent group, such as mice, rats, guinea pigs and hamsters. Rabbits also are a preferred species. The criteria for choosing an animal will be largely dependent upon the particular preference of an investigator.

The first step is to create a tissue flap in the experimental animal. The term "tissue flap" means any incision in the flesh of the animal that exposes the target tissue. It is generally preferred that an incision be made in the dorsal flank of an animal, as this represents a readily accessible site. However, it will be understood that an incision could well be made at other points on the animal, and the choice of tissue sites may be dependent upon various factors such as the particular type of therapeutics that are being investigated.

Once a target tissue site is exposed, carcinoma cells, either individually or in microscopic tumors, are contacted with the tissue site. The most convenient manner for seeding the cancer cells into the tissue site is to apply a suspension of tissue culture media containing the cells to the exposed tissue. Cancer cell application may be achieved simply using a sterile pipette or any other convenient applicator. Naturally, this procedure will be conducted under sterile conditions.

In a particular example, $2.5 \times 10^6$ cells are inoculated into the exposed tissue flap of a nude mouse. Those of skill in the art will be able to readily determine, for a given purpose, what the appropriate number of cells will be. The number of cells will be dependent upon various factors, such as the size of the animal, the site of incision, the replicative capacity of the tumor cells themselves, the time intended for tumor growth, the potential anti-tumor therapeutic to be tested, and the like. Although establishing an optimal model system for any particular type of tumor may require a certain adjustment in the number of cells administered, this in no way represents an undue amount of experimentation. Those skilled in the area of animal testing will appreciate that such optimization is required.

This can be accomplished, for example, by conducting preliminary studies in which differing numbers of cells are delivered to the animal and the cell growth is monitored following resealing of the tissue flap. Naturally, administering larger numbers of cells will result in a larger population of microscopic residual tumor cells.

However, it is envisioned that persons skilled in the art may use any of a variety of methods routinely used to seal the incision such as the use of adhesives, clamps, stitches, sutures, etc., depending on the particular use contemplated.

Other orthotopic animal models are well known in the art. The orthotopic lung cancer model, for example has been described in the literature. This protocol involves injection of tumor cells into the bronchus of a mouse wherein tumors will form in the bronchus and bronchioles, mimicking tumors commonly found in non-small cell lung cancer patients. The skilled artisan will readily be able to adapt or modify each particular model for his intended purpose without undue experimentation.

O. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Isolation And Cloning of WWOX

Chromosomal and genomic abnormalities affecting chromosome 16q (ch 16q), have been reported in cytogenetic and allelotypic studies of various epithelial tumors. The loss of heterozygosity (LOH), affecting the long arm of this autosome is often observed in breast carcinomas and pre-invasive breast lesions (Sato et al., 1990; Tsuda et al., 1994; Cleton-Jansen et al., 1994; Aldaz et al., 1995; Chen et al., 1996). Other tumor types, such as prostate and hepatic carcinomas also exhibit similar abnormalities (Chen et al., 1996; Carter et al., 1990). Therefore, identification of putative tumor suppressor gene(s) that may reside in the distal portion of ch 16q has been the subject of several studies (Whitmore et al., 1998; Crawford et al., 1999 Savino et al., 1999).

One of the most commonly affected areas spans the region between STS markers D16S515 and D16S504 with the most affected locus D16S518 at 16q23.3–24.1 (Chen et al., 1996). The high incidence of LOH observed at pre-invasive stages of tumor development indicates the possibility of a candidate tumor suppressor gene or genes at location 16q23.3–24.1 which may play an important role in early breast carcinogenesis (Chen et al., 1996). Describe herein are the physical mapping of the chromosomal region between STS markers D16S518 and D16S516, and the cloning of a novel gene from within this area.

Methods

BACs Identification and Development of STSs and DNA Sequencing. YAC and BAC clones spanning the region of interest were identified by PCR screening of STSs. BACs were isolated from BAC library CITB-HSP-C (Research Genetics, Huntsville, AB). BAC ends were sequenced using SP6 and T7 vector primers to generate novel STSs for contig building.

Genomic DNA shotgun sequencing was performed using DNAseI BAC DNA digestion and subsequent cloning into pZErO-1 vector (Invitrogen). Inserts were amplified with vector specific primers. Cycle sequencing reactions were performed using ABI PRISM BigDye Terminator cycle sequencing chemistry (Perkin Elmer/Applied Biosystems) and analyzed on an ABI 377 automated fluorescent sequencer (Perkin Elmer/Applied Biosystems). Some clones were sequenced manually with $^{32}$P labeled primers.

Isolation of Candidate cDNAs. cDNA clones were isolated following a modification of a solution hybrid capture method described by Futreal et al., (1994), using BAC clones from the region of interest, as selector DNA, and isolating cDNA clones from a human mammary gland cDNA library (5'-STRECH, Clontech Laboratories, Inc). All cloned cDNAs were sequenced and analyzed using the BLAST algorithm, searching all available GenBank human databases. The isolated cDNA clones were mapped back to the corresponding BAC (selector) DNAs and compared with the genomic DNA sequence.

WWOX cDNA Isolation and Exon-Intron Structure Determination. A consensus sequence was generated by alignment of the primary cloned cDNA sequence and matching ESTs. From this sequence primers were prepared to isolate the full length cDNA. Two independent clones were isolated from a placenta cDNA library panel (Rapid Screen, OriGene Technologies, Inc.). Additionally, a second strategy was followed using the 5' and 3' RACE PCR method on a human mammary gland cDNA library (Marathon-Ready, Clontech Laboratories, Inc.) according to the manufacturer's protocol. The cDNAs isolated by this method were cloned, System Promega) with full length WWOX cDNA as template. $^{35}$S-methionine labeled products were analyzed by SDS-polyacrylamide gel electrophoresis followed by phosphorimager detection.

Mutation Screening. Genomic DNA isolated from a panel of 27 breast cancer cell lines was used to resequence each of the exons of WWOX. Primers for individual exon amplification and sequencing are specified in Table 7.

TABLE 7

WWOX intron-exon junctions and PCR/sequencing primers

| Exon or Intron | Starting position in cDNA | Exon length (bp) | Acceptor splice site[a] | Donor splice site[a] | Intronic primers for mutation screening (5'-3') | PCR product size (bp) |
|---|---|---|---|---|---|---|
| 1 | 1 | 232 | | ACGCCAA/gtaagggggc (SEQ ID 61) | 1F- ACTGGATTTCAGCTTCGTGGTCG (SEQ ID 35)<br>1R- TCCGTGGGCTGTGCAGGGTC (SEQ ID 36) | 334 |
| 2 | 233 | 65 | tttttaacag/TCACACC (SEQ ID 53) | GCAGGAG/gtttgtatgt (SEQ ID 62) | 2F-TTCCCCCTACTTCCTTCTTATATCTGGC (SEQ ID 37)<br>2R- ATCCTCACTCCACCCTATGATCTCATC (SEQ ID 38) | 373 |
| 3 | 298 | 58 | tgtgtttcag/ATTGCC (SEQ ID 54) | TTGTTGA/gtaagtgtct (SEQ ID 63) | 3F- ATGGTCTTTACTTCTCCCTGGCAC (SEQ ID 39)<br>3R- ACTTCTGCTAAGATTACAGATACACACTG (SEQ ID 40) | 244 |
| 4 | 356 | 179 | tttgggcag/CCATATA (SEQ ID 55) | GGAATAG/gtaggctctt (SEQ ID 64) | 4F- AGTTCTTTCAGGTTTAAGGAATAAGC (SEQ ID 41)<br>4R- TAGATCTAAGTGGATCTCATTATAGCAG (SEQ ID 42) | 370 |
| 5 | 535 | 107 | taaaccatag/GGTTCGA (SEQ ID 56) | AGAATGG/gtaagcgctt (SEQ ID 65) | 5F- ACTTGGGGTAATTTAAGTGGTGCTC (SEQ ID 43)<br>5R- AACTTTACACACTCCACTGAAATCTCC (SEQ ID 44) | 296 |
| 6 | 642 | 90 | ctcattgcag/CATAAAG (SEQ ID 57) | GAATGTG/gtaagcgctt (SEQ ID 66) | 6F- ATTAAACAGGGGAATTCCGAC (SEQ ID 45)<br>6R- TCTCCCAATTGTGTTCATCTG (SEQ ID 46) | 278 |
| 7 | 732 | 185 | tttttcagg/CCTCTTC (SEQ ID 58) | CCCATCG/gtgggtttga (SEQ ID 67) | 7F- ACATCCATGGATCCCGAAG (SEQ ID 47)<br>7R- TGGTATGAGAAAGGGGATAAGTG (SEQ ID 48) | 318 |
| 8 | 917 | 265 | tattttaag/ATTTACA (SEQ ID 59) | GTCCATG/gtaagagaac (SEQ ID 68) | 8F- TGCACCCAGCATTCCTTAGATTTCC (SEQ ID 49)<br>8R- ACCAGACTCATGCCCGCAAG (SEQ ID 50) | 459 |
| 9 | 1182 | 1060 | ggatttccag/CAACAGG (SEQ ID 60) | | 8F- AAATGACGCCATCTCATCACTCC (SEQ ID 51)<br>8R- TGTTTTCCTGGCATCTACGAGAAG (SEQ ID 52) | 1259 |

[a]Exonic sequences indicated in upper-case; Intronic sequences indicated in lower-case.

sequenced, aligned and compared with the clones isolated from the placenta library to determine the full-length cDNA. Primers for the 5' and 3' ends of WWOX cDNA were used as a first step to isolate additional BAC genomic clones. After the intron-exon junctions for a specific exon were determined, primers for the next exon were designed. The whole length cDNA sequence was compared with the genomic sequence to determine the genomic structure of WWOX.

Protein Sequence Analysis. The WWOX amino acid sequence was analyzed using the BLASTP and PSI-BLAST algorithms in search for matches or homologies in the GenBank protein databases. The identification of protein family domains were determined by using the Pfam domain models (PFAM: Multiple alignments and profile HMMs of protein domains. Release 4.3. The Pfam Consortium, http://pfam.wustl.edu/).

Northern Analysis. Northern blots using 2 μg polyA RNA from breast cancer cell lines and normal human breast epithelium were prepared using standard procedures. The multi-tissue Northern blot was purchased from Clontech. A 1553 bp EcoRI restriction fragment of WWOX clone, spanning the 5' end and amino acid coding region, was used as probe after labeling with [$^{32}$P]α-dCTP using random priming (Prime It II, Stratagene, Calif.). The membranes were hybridized in Rapid-hyb buffer (Amersham), followed by washing according to the manufacturer's protocol.

In vitro translation. In vitro translation was performed using an in vitro transcription-translation reticulocyte lysate assay (TNT T7 Quick Coupled Transcription/Translation, Results General Characterization of the Chromosome 16q Region of Interest. The present inventors focused on the 16q23.3–24.1 chromosome region due to the LOH analyses (Chen et al., 1996) and an allelotypic study using a panel of 27 breast cancer cell lines which revealed a very high incidence of hemizygosity within this area affecting 70–80% of these cell lines and one primary tumor case with a homozygous deletion (Bednarek and Aldaz, 1998). Two approaches were used to characterize the chromosomal region of interest to isolate the putative tumor suppressor gene/s. After building a YAC and BAC contig spanning the D16S518-D16S516 region conventional shotgun cloning and sequencing and cDNA isolation were performed. Several cDNA clones were isolated from the area using a solution hybrid cDNA capture method (Futreal et al., 1994). A total of 35 cDNAs were isolated and sequenced, of which 17 matched previously isolated ESTs, and 18 showed no matches in any of the GenBank databases. All the isolated cDNA clones were mapped back to the corresponding BAC DNAs and their sequence compared with the genomic DNA sequence in order to identify evidence of exon-intron structure. Only the cDNA corresponding to the WWOX gene showed such features.

Approximately 400,000 bp of the region covered by the overlapping BACs 112B7, 249B4, 286F3 and 36022 was sequenced (FIG. 1) including a continuous sequence of 96371 bp (accession number AF179633). This genomic sequence was also analyzed for matching EST clusters from GenBank databases. Of the numerous ESTs identified and analyzed none showed evidence of ORF or exon-intron structure.

Isolation and Characterization of WWOX. Following sequencing the mentioned cDNA two independent full-length cDNA clones were isolated from a placenta cDNA library using specific PCR primers which spanned the transcript. These full-length cDNAs showed a consensus sequence of 2264 bp long with a predicted ORF of 1245 bp, a 125 bp long 5' untranslated region and a 3' untranslated region (3'UTR) 870 bp long with a polyadenylation signal AATAAA starting at position +2091 (cDNA reported to GenBank under accession number AF211943). The putative start ATG codon is located within a strong Kozak sequence (TCAGCCatgG) which contains a highly conserved G residue (position +4) and purine (G residue at position −3) (Kozak, 1996). An in frame stop codon is present −30 bp from the predicted translation start site, indicating that the whole ORF was cloned. This gene was named WWOX for the reasons discussed below.

WWOX's exon structure and exon-intron boundaries were determined and the chromosomal location of the gene was confirmed to the region of interest. To this end various combinations of PCR primers were designed based on the cDNA sequence and then mapped back to the corresponding BACs. Subsequent sequencing of the predicted exons permitted the exon-intron boundaries to be established at the genomic DNA level (FIG. 1).

WWOX is composed of nine exons, ranging in size from 58 bp to 1060 bp (Table 7). Based on analysis of the promoter region (reported to GenBank under accession number AF212843) the first exon was localized within a CpG island starting at position −660 and extending into the first intron at 292 bp from the ATG translation start site. This area shows a 63% content of C+G and 8% CpG with the highest percentage within the area from −300 bp to ATG (68% and 11%, respectively).

The 3' end of WWOX had high sequence homology to a previous GenBank entry of a human putative oxidoreductase (U13395, locus ID 9621). Furthermore, the physical map of WWOX spanned the whole region of interest. Exon1 mapped WWOX to the BAC containing D16S518 and exon9 and the 3' UTR to the BAC containing D16S516 (FIG. 1). WWOX spans a large genomic region of approximately 1 Mb in size. Although the exact lengths of the intronic portions of this gene were not determined this estimate was based on the known size of the YAC clones, the average size of BAC clones (~150 kb) and the shotgun sequencing (described above) wherein the approximately 400,000 bp corresponded to WWOX's intron 8 area (FIG. 1). Interestingly, analysis of sequence contigs from this large intronic region allowed identification of two previously described translocation breakpoints mapping to this same area. These translocation breakpoints, MM.1 and JJN3 have been described in multiple myeloma involving chromosomes 14 and 16, i.e. t(14;16)(q32;q23), (Chesi et al., 1998). Further sequence analysis of this area also identified the existence of a pseudogene for Ribosomal Protein S3 matching to sequence within this intronic region (AF179633). This is the first report of a gene in this chromosomal area (i.e. D16S518-D16S516).

WWOX protein structure. The 1245 bp WWOX ORF encodes for a 414 amino acid protein (FIG. 2). The BLAST and PSI-BLAST algorithms were used to search for matches in GenBank databases. Interestingly, the N terminus of the putative WWOX protein showed homology to ubiquitin ligases such as NEDD4, YES-associated protein YAP65 and other WW-domain containing proteins. Further amino acid sequence analysis using the PROSITE database identified two regions within the putative WWOX protein (amino acids 18–47 and 59–88) which have high homology to WW-domain sequences. The first motif exhibits typical features of a WW domain, is 26 bp long with the two highly conserved tryptophan, and one proline, residues. In the second WW domain one tryptophan is replaced by a tyrosine residue, this is an alternative functional replacement which is also found in other WW domain proteins (FIG. 2).

The amino acid sequence also revealed homology to numerous proteins known as members of the short chain dehydrogenase/reductase family (SDR). The SDR family encompasses a wide variety of enzymes which act on diverse hydroxy/keto substrates. The most conserved features of SDR proteins are two domains constituting the cofactor, GXXXGXG, and substrate, YXXXK, binding sites (Jornvall et al., 1995). Further WWOX amino acid sequence analysis identified both the coenzyme, NAD(H) or NADP (H), binding site GANSGIG at position 131–137, and the potential substrate binding site, YNRSK, at positions 293–297 (FIG. 2).

Due to the presence of the WW domains and the homology to SDR this novel protein was named WWOX. Analysis using the PSORT algorithm predicts that WWOX has no N terminal signal peptide and its localization is probably in the cytoplasm (Nakai and Kanehisa, 1992).

WWOX expression analysis. Northern blot analysis with a probe derived from 5' end of WWOX revealed a 2.2 kb mRNA which is in agreement with the length of the cDNA clone i.e. 2264 bp.

Analysis of the WWOX expression pattern in normal human tissues showed that expression was highest in testis, prostate and ovary, and significantly lower in the other examined tissues including bulk breast tissues which showed very low levels of expression.

Analysis of the expression of WWOX in normal mammary epithelial cells in culture and in breast cancer cell lines was also performed. All the breast cancer lines analyzed showed higher WWOX expression than normal breast tissue and normal mammary epithelial cells (HME-87). However, amongst the breast cancer lines analyzed, WWOX expression levels varied from relatively low in T47D and MDA-MB435 to high overexpression in ZR75-1 and MCF-7 cells. Of these cell lines, previous extensive allelotypic analysis using highly polymorphic STS markers allowed the determination that T47D, ZR-75, MDA-MB435, MDA-MB453, SKBR3 and UACC812 were amongst the group of breast cancer lines with no evidence of STS heterozygosity along most or all of 16q (13). This indicated the high likelihood that they had lost all or a large portion of one of the original parental 16q arms including the region spanned by WWOX. However the putative hemizygous status of WWOX did not impede expression. No correlation was found between the estrogen receptor status of the breast cancer lines and the levels of WWOX expression.

To examine whether the translation of the ORF of WWOX produced the predicted protein, an in vitro transcription/translation system was used. SDS PAGE analysis of the translated product revealed a single protein product of approximately 46 kDa. This agrees with the predicted molecular weight of WWOX based on its amino acid sequence (i.e. 46676.8 Da).

Mutation screening in breast cancer cell lines. As mentioned above, WWOX spans the whole chromosomal area of interest between STS markers D16S518 and D16S516. The high incidence of LOH affecting this region suggested the presence of a putative tumor suppressor gene within this area. Thus, in order to investigate whether WWOX is a target for mutations in breast cancer, we performed a mutation screening on a panel of 27 breast cancer cell lines.

This panel of breast cancer cell lines were of particular interest because the inventors had previously observed a high incidence of hemizygosity within the chromosome 16q area of interest (Bednarek and Aldaz, 1998), i.e., cell lines in which the majority had already lost one WWOX allele via chromosomal rearrangements. Only one breast cancer case displayed a homozygous deletion in this region (Bednarek and Aldaz, 1998). This deletion spanned part of WWOX's intron 8 region from STS 249B4S to D16S3029 inclusive (see FIG. 1).

Each of the WWOX exons was amplified from each of the 27 breast cancer lines genomic DNA and the products were sequenced. The intronic primers used for amplification and sequencing are detailed in Table 7.

No evidence for point mutations was seen. Two substitutions were found which may be polymorphic rather than a mutational. The first, a C/T found at position −5 in the Kozak sequence, was observed in 50% of the tumor samples but it was also observed that DNA isolated from normal mammary gland was polymorphic at this position. The second substitution, a G/A at position +534, results in an amino acid change, alanine/threonine, but because of the approximate frequency of 50% for either allele in the samples examined and because heterozygosity at this position was also found in normal DNA, it may also represents a polymorphism.

Abnormally spliced WWOX transcripts in tumor cell lines. Expression analysis was also performed on a panel of multiple myeloma cell lines using Northern blot analysis. Multiple myeloma cell lines were of particular interest because various myeloma specific chromosomal translocations breakpoints were identified within the genomic region spanned by WWOX. A subset of the cell lines used were known to carry a chromosomal translocation involving chromosomes 14 and 16, t(14;16). Northern blot analysis identified variable levels of expression among these various myeloma cell lines. Two of the myeloma cultures showed strong hybridization of the WWOX probe to lower size transcripts to that expected for the wild type WWOX mRNA. These two cell lines were among those known to carry the t(14;16) translocation. RT-PCR analysis and sequencing of the transcript detected in the KMS11 cell line showed that the shorter transcript represents an abnormally spliced version of WWOX in which exons 5 through 8 are deleted (WWOX Δ5–8). The second myeloma cell line, JJN3, showed a strong alternative band on the Northern blot. This small transcript comprised exons 1–3.

As described above Northern hybridization demonstrated overexpression of WWOX in several breast cancer cell lines when compared to normal breast mRNA. The highest expression level was found in cell lines ZR75-1 and MCF-7. Interestingly, the MCF-7 cell line also showed a lower size transcript in the Northern analysis. An expression analysis was performed by RT-PCR on numerous cell lines derived from different types of cancer with numerous normal tissue samples as controls. This analysis identified the existence of several alternatively spliced forms of the WWOX transcript which were only observed in the tumor cells and not in the normal cells. Sequencing analysis confirmed that these were abnormally spliced transcripts of WWOX. For example, in cell lines MCF-7 and MDA-MB 453 which are breast cancer cell lines; HCT116 a colon adenocarcinoma cell line; and AGS a gastric adenocarcinoma cell line have deleted exons 6 through 8 (WWOX Δ6–8). Additional alternative transcripts detected in other lines appear not to encode functional forms since a translation initiation site was not detected in such transcripts.

Identification of WWOX binding partners and studies on cell localization. Identification of putative binding proteins for WWOX were performed by Far-Western blot studies employing GST-Fusion constructs of the WW domains of WWOX proteins. The present inventors have detected a preference of WWOX for binding PPPY motif. In studies using protein membrane arrays, a series of potential binding partners for WWOX were identified. These include the proline rich ligand containing oligopeptides such as, Ld10 (PPLP), P3 (PPR), CDC25 (PLT*P) and WBP1 (PPPY). The inventors contemplate further experiments to identify WWOX binding target proteins.

The cellular localization of WWOX proteins have been studies. A WWOX-GFP fusion protein was generated and transfected into normal breast cells. Perinuclear aggregates of WWOX were seen inside specific organelles. Double labeled studies indicate that WWOX proteins localize to the Golgi apparatus and not to the mitochondria.

Discussion

The inventors outlined the physical map of a 16q chromosomal region commonly affected by abnormalities in breast and other cancers. The area spans from STS marker D16S518 to D16S516 in the 16q23.3–24.1 region. A novel gene mapping to this area, with unique characteristics was cloned. This gene, WWOX, contains two WW-domains on the N terminus of the protein and a SDR central domain. By analogy to other WW domain containing proteins, the WW motifs should play a role in protein—protein interactions. The SDR domain can bind low molecular weight ligands and cofactors and the corresponding putative binding motifs have also been identified in WWOX.

The protein motif called WW or WWP was identified in very different types of proteins including peptidyl-prolyl isomerases involved in mitosis regulation (Lu et al., 1996; Maleszka et al., 1996), the cytoskeletal protein, dystrophin (Bork and Sudol, 1994), spliceosome-associated proteins (Bedford et al., 1998), the ubiquitin-protein ligase NEDD4 (Staub et al., 1996), signal transducing protein YAP65 (Chen and Sudol, 1995). This domain is characterized by the presence of very conserved proline and tryptophan residues (Bork and Sudol, 1994; Andre and Springael, 1994; Hofmann and Bucher, 1995). WW domains are known to interact with the proline rich motifs of other proteins. So far, four different WW binding proline rich motifs have been identified; PPXY (23), PPLP (Chan et 1996), PGM/PPR (Bedford et al., 1998) and phosphoserine/phosphothreonine (Lu et al., 1999).

Short chain dehydrogenases/reductases represent a wide spectrum of enzymes. The protein domain database (PROSITE) identifies more than 60 different proteins from bacteria, fungi, plants and animals, which belong to this family. These are typically enzymes which metabolize different alcohols, sugars, keto-acyls, retinoids, steroids and other hydroxy/keto substrates. One important group among the SDR proteins is the family of hydroxysteroid dehydrogenases. The average size of SDR enzymes is 250–300 amino acids. Even-though overall similarity between the different SDRs can be as low as 15–30%, a small conserved substrate binding motif, YXXXK, and a coenzyme binding motif, GXXXGXG, are characteristic for these proteins (Jornvall et al., 1995). Although the 414 amino acids of WWOX make it larger than the average SDR enzyme, the WWOX dehydrogenase domain exhibits the typical sequence features and distances between conserved motifs that are characteristic of SDR enzymes (Duax and Ghosh, 1997). WWOX is, as yet, the only protein described which contains both binding motifs for low molecular weight ligands/substrates and WW-domains.

WWOX has one additional putative signature, which is a serine residue 12 amino acids upstream of the YNRSK substrate binding motif. This serine is at a nearly identical location to that observed in steroid dehydrogenases (usually position −13 from Y) which is suggested to play an important role in the catalysis of steroid substrates (Duax and Ghosh, 1997).

Hydroxysteroid dehydrogenases/reductases usually show a wide tissue expression profile. Although some enzymes of this family are tissue specific. Northern analysis has shown that WWOX transcripts are highly represented in hormonally active tissues with testis showing the highest expression. This tissue specificity in addition to the SDR domain features, indicates that WWOX's substrate for dehydrogenase/reductase activity is probably a steroid. As WWOX has the ability to interact with other proteins via the WW domains, this protein can participate in steroid-receptor interaction regulation. Based on amino-acid sequence analysis WWOX localizes to the cytoplasm of cells (Nakai and Kanehisa, 1992).

WWOX is overexpressed in breast cancer cells when compared with normal tissues. The cell line with the highest WWOX mRNA expression is the MCF7 line, which is characterized by its high dependence on estradiol for growth. This indicates that WWOX plays a role in estradiol/ER interaction regulation.

As WWOX spans a chromosomal area characterized by a very high incidence of allelic loss and chromosomal rearrangements. Furthermore, two previously described chromosomal breakpoints, MM.1 and JJN3, were mapped to the last intron of WWOX (FIG. 1). These specific 16q translocation breakpoints, t(14;16)(q32;q23) were previously described in multiple myeloma (Chesi et al., 1998). Consequently at least one of the alleles of WWOX is truncated in some multiple myeloma lines. Hence, WWOX inactivation plays a role in multiple myeloma. In myeloma studies it was also observed that other additional translocation breakpoints such as KMS11 and ANBL6, also map to the same region covered by YACs 933h2 and 972d3 and hence in very close vicinity of WWOX. Nevertheless, the putative oncogenic target for transcriptional dysregulation in the myeloma translocations was proposed to be c-maf oncogene which is located telomeric of WWOX and in the opposite 5'-3'orientation. Hence, the present inventors investigated whether the c-maf oncogene showed any expression alterations in the breast cancer lines. No abnormalities of c-maf expression was seen when comparing breast cancer lines with normal breast cells and tissues.

Several translocations and deletions affecting ch16q23 have been described as primary cytogenetic anomalies in several breast cancers (Dutrillaux et al., 1990; Pandis et al., 1992). The inventors found one breast cancer case with a homozygous deletion also mapping within the same intron 8 region in which the translocation breakpoints were mapped. Interestingly, the locus for the yet uncharacterized common fragile site FRA16D has been cytogenetically mapped to this very same chromosome region 16q23.2–23.3.

All these evidence suggest that the whole genomic region spanned by WWOX and in particular the intron 8 region appear to be an area prone to chromosomal fragility. This indicates that this area could be the same as the mentioned common fragile site FRA16D, since it displays features of genomic fragility similar to those observed in other better characterized common fragile site loci (e.g. FRA3B) (Sutherland et al., 1998; Smith et al., 1998).

EXAMPLE 2

Identification of Abnormal Transcripts

Abnormal WWOX transcripts, such as the alternatively or abnormally spliced versions of WWOX, are identified using cDNA samples synthesized from RNA isolated from tumor samples by means of RT-PCR and employing deletion specific primers.

In one embodiment, a common 5' primer 5'-AGGCAGT-GCGCAGGCGTGAGC-3' (SEQ ID NO:14) was used in conjunction with 3' specific primers spanning the new exon—exon junctions found only in these alternatively spliced forms expressed in tumors:

The 3' specific primers used were:

```
Δ8   (5'-ACGGTGGTGGCAGCTCCCTGTTGCGATGG-3');      (SEQ ID NO:4)

Δ7-8 (5'-ACGGTGGTGGCAGCTCCCTGTTGACATTCTTGG-3'); (SEQ ID NO:5)

Δ6-8 (5'-ACGGTGGTGGCAGCTCCCTGTTGCCATTCTTC-3');  (SEQ ID NO:6)

Δ5-8 (5'-ACGGTGGTGGCAGCTCCCTGTTGCTATTCC-3')     (SEQ ID NO:7)

Δ4-8 (5'-TGGTGGCAGCTCCCTGTTGTCAACAAAAAACAC-3')  (SEQ ID NO:8)

Δ3-8 (5'-ACGGTGGTGGCAGCTCCCTGTTGCTCC-3')        (SEQ ID NO:9)

Δ2-8 (5'-ACGGTGGTGGCAGCTCCCTGTTGTTG-3')         (SEQ ID NO:3)
```

Using these methods the inventors have identified truncated WWOX transcript in cell lines derived from multiple myeloma subtypes, breast cancers, colonic adenocarcinomas and gastric adenocarcinomas.

EXAMPLE 3

Fluorescent In Situ Hybridization

Metaphase or Interphase cells from normal or tumor samples were analyzed with probes spanning the WWOX, fragile site 16 D (FRA16D) genomic region. Induction of chromosomal fragility in normal cells such as, peripheral lymphocytes, is achieved by treatment with Aphidicolin (0.4 mM) dissolved in DMSO during the last 26 hrs. of culture. Spontaneous WWOX FRA16D genomic region breakage in tumor cells from diverse origin can also be analyzed.

Metaphase spreads from normal or tumor cells are prepared after 1 hr. incubation in culture media Colcemid (50 mg/ml). This is followed by standard KCL hypotonic incubation and acid-methanol fixation. Samples from the cells are then spread onto clean glass slides. YAC or BAC probes spanning or flanking the WWOX (FRA16D) genomic region are labeled with digoxigenin or biotin or a fluorescent dye such as FITC or Texas Red and use for in situ hybridization on the cell spreads. Prior to hybridization DNA from the samples is denatured using high temperature and Formamide. Hybridization of the labeled probe to the samples is conducted at 37° C. overnight following standard in situ hybridization procedures. Detection of the signal is performed by multiple procedures depending on the original method of labeling the probe. Analysis and digital imaging is performed utilizing a CCD cooled camera mounted in a conventional fluorescent microscope.

The signal is detected as two distinctive spots in normal interphase cells with no breakage, and is detected as additional spots when breakage on the region of interest has occurred. The frequency of cells with WWOX breakage is determined. Individuals at higher risk of cancer will show a higher frequency of WWOX FRA16D breakage when cells are exposed to Aphidicolin. The same method can be used to asses the frequency of spontaneous breakage in individuals at risk of cancer, i.e. in untreated normal cells.

In an alternative method, closely flanking WWOX FRA16D probes can be labeled with two different labels (e.g. red and green) in interphase cells. When no breakage both colors will overlap and be detected as yellow. When breakage occurs both colors will be distinctive. These methods can be used for the analysis of normal and tumor cells.

EXAMPLE 4

Suppression of Tumor Growth by WWOX in In Vitro and In Vivo Systems

This example is concerned with evidence demonstrating the function of WWOX as a suppressor of tumor growth in vivo in a mouse model of tumor. Furthermore, in vitro experiments demonstrate that ectopically expressed WWOX supresses tumor cell growth in breast cancer cell lines. Also reported herein is the detection of aberrantly spliced WWOX mRNA forms with deletion of exons 5–8 or 6–8 in cancer cell lines and in primary breast tumors. These aberrant mRNA forms were not detected in normal tissues. The present inventors have also demonstrated that proteins translated from such abnormal transcripts have a different cellular localization than wild-type WWOX protein.

Materials and Methods

Cell Lines, Normal and Tumor Tissues. Cell lines used in these experiments were derived from the inventor's collection or were obtained from ATCC. Normal and breast tumor samples were obtained from the Cooperative Human Tissue Network.

Nucleic Acids. RNA was isolated using Trizol reagent (Gibco BRL) according to the manufacturer protocol. Isolated RNAs were treated with DNAse I (Promega) prior to cDNA synthesis, which was performed using Superscript II Reverse Transcriptase (Gibco BRL) according to the manufacturer protocol. For the methylation study, MDA-MB-435 cells were treated in culture with 5-aza-2'-deoxycytidine (3.5 µg/ml) for 48 hours.

Real-time and Nested RT-PCR. Real-time RT-PCRs were performed with primers for the wild type WWOX transcript designed to span intron 8. The primers used were: forward primer 5'TCGCAGCTGGTGGGTGTAC3' (SEQ ID NO:10) located on exon 8 and reverse primer 5'AGCTC-CCTGTTGCATGGACTT3' (SEQ ID NO:11) on exon 9.

Real-time RT-PCR was performed on a Perkin-Elmer Biosystems Gene Amp 7700 Sequence Detection System. All reaction components were purchased from PE Biosystems. Detection of double-stranded PCR products was performed with SYBR Green I. All reactions were performed in triplicate. Relative levels of expression were normalized using as internal reference control the P2-microglobulin gene (5'TGAGTGCTGTCTCCATGTTTGA3' (SEQ ID NO:12) and 5'TCTGCTCCCCACCTCTAAGTTG3') (SEQ ID NO:13) (Mitas et al., 2001). Nested RT-PCR to determine the existence of aberrant transcripts of WWOX was performed using primers spanning the whole ORF: forward 5'AGGCAGTGCGCAGGCGTGAGC3' (SEQ ID NO:14); reverse 5'CAGCCCTGGCACTTGCGTGAGG3' (SEQ ID NO:15) and nested primer set; forward 5'AGCAGGCGT-GAGCGGTCGG3' (SEQ ID NO:34); reverse 5'TGCGT-GAGGGGACACACACAGG3' (SEQ ID NO:16). RT-PCR screening for aberrantly spliced WWOXΔ6–8 mRNA was performed using primers: forward 5'GAGTTCCTGAGC-GAGTGGACCCG3' (SEQ ID NO:17) and reverse primer 5'ACGGTGGTGGCAGCTCCCTGTTGCCATTCTTC3' (SEQ ID NO:6) which is positioned on a novel exon—exon junction between exons 5 and 9 and does not amplify the wild-type transcript. These RT-PCR reactions were performed using Expand High Fidelity PCR System (Roche).

Bisulfite DNA Sequencing. Cell lines DNA was isolated using standard methods and bisulfite sequencing was performed as previously described (Clark et al., 1994). Primers for amplification of modified DNA for the sense strand; 5'TAGTTTTTATTATTATTAGTTTTTATTATT3' (SEQ ID NO:18) and 5'AATACTACATCCTAAACAACAA3' (SEQ ID NO:19) and for nested PCR; 5'AGTTTTTATTATTAT-GAGTTTTTATTAAAT3' (SEQ ID NO:20) and 5'CCRCR-CAATACTACATCCTA3' (SEQ ID NO:21). For the antisense strand PCR; 5'GGGATGAGGTYGTTTTGTTT3' (SEQ ID NO:22) and 5'TCATAAATCTCTATTAAACAA-CAA3' (SEQ ID NO:23) and nested PCR set; 5'GYGTAGT-GTTGTATTTTGAAT3' (SEQ ID NO: 24) and 5'TCA-CAATCTCTATTATATATTTAACTA3' (SEQ ID NO: 25). For sequencing nested primers 5'TCCTCCCCRCR-CAAATAAC3' (SEQ ID NO: 26) and 5'TTATTATTAT-GAGTTTTTATTAAATAATAG3' (SEQ ID NO:27) for the sense strand and 5'ACCTAAACTACATTTCCCATATCC3' (SEQ ID NO:28) and 5'TAGTGTTGTATTTTGAATAG-TAG3' (SEQ ID NO:29) for the anti-sense strand were used.

Vector Construction and Stable Transfection. WWOX wild-type cDNA was cloned into the pHOOK3 vector (Invitrogen) or the pLNCX2 retroviral vector (Clontech). Transfections were performed using a standard calcium phosphate precipitation method with 10 µg DNA of vector or WWOX cDNA clone.

For retroviral transduction, WWOX cloned into pLNCX2 vector was transfected into the PT67 packaging cell line (Clontech). Positive transfectants were selected for one week with G418 (200 µg/ml). Viruses were produced according to the manufacturer protocol. Target cells were grown to 30% confluence and infected with viruses (approx. $10^6$ cfU/ml) mixed with cell specific culture medium with polybren as vehicle (8 µg/ml). After 24 hrs medium was replaced and stable transfectants were selected with 200 µg/ml of G418 for two weeks.

Soft agar growth assay. The assay was performed using $5 \times 10^3$ of MDA-MB-435 cells in 2 ml medium (DMEM+10% FBS) supplemented with 0.34% agarose (FMC) and layered on 3 ml base of 0.9% agarose with medium. For T47D cells $5 \times 10^4$ cells and medium containing DMEM+10% FBS+10 µg/ml insulin was used. Experiments were performed in triplicate in 35 mm 6 well plates. After 4 weeks of growth cells were stained by incubation with nitro blue tetrazolium, cultures were photographed and colonies with diameter larger than 200 μm were counted and measured using the NIH Image analysis software.

In vivo tumorigenicity assay. Female BALB/c athymic nude mice (NCI) were used. Eight weekold animals (five for each construct) were injected bilaterally into the thoracic mammary fat pad area with $1 \times 10^6$ cells (per side) MDA-MB-435/vector or MDA-MB-435/WWOX. Tumor growth was monitored for a period of 7 weeks. Tumor diameter was determined by caliper measurements once per week and tumor volume was calculated using the formula: "π/6×larger diameter×(smaller diameter)$^2$". At the end of the experiment tumors were dissected and the individual tumor wet weight was determined.

GFP-WWOX fusion and cellular localization. GFP-WWOX N-terminal fusion proteins were constructed using pEGFP-N Vector Systems (Clontech). MCF-10F cells ($1 \times 10^7$) were electroporated in 400 μl complete medium with 20 μg of the GFP-WWOX construct DNA. Cells were plated into 4-well cover-slip chambers and incubated for 24 hrs prior to confocal microscopy analysis. Golgi system was visualized with the anti-Golgi 58 K monoclonal mouse anti-human antibody (Sigma) and Cy5 labeled anti-mouse IgG donkey secondary antibody (Jackson ImmunoResearch Lab.). Brefeldin A (BFA) (Sigma) treatment was performed 72 hrs post-electroporation (5 μg/ml) for 45 min. followed by 35 min. recovery in BFA free media. Mitochondria were visualized using MitoTracker RedCMXRos (Molecular Probes).

Results

Analysis of WWOX expression in cancer cell lines and breast tumors. Northern blot analysis demonstrated that breast cancer cell lines express highly variable levels of WWOX mRNA with some of these cell lines expressing very low to undetectable levels of expression (Bednarek et al., 2000). In order to perform a comparative analysis of levels of expression of WWOX, a quantitative analysis using a real-time RT-PCR was performed. The results on the relative expression of WWOX are summarized in FIG. 4. Some breast cancer cell lines showed very low or almost undetectable levels of WWOX expression as determined by this highly sensitive assay, for example, MDA-MB-435, MDA-MB-231, BT-549 and T47D.

Interestingly, several of these breast cancer cell lines, that have very low to undetectable WWOX levels, are known to be highly tumorigenic as determined by their ability to form tumors in nude mice (Price et al., 1990; Xie et al., 2001). In contrast, cell lines such as MCF7 and BT-20, which showed higher levels of WWOX expression, have a much lower tumorigenic potential (Xie et al., 2001).

Promoter methylation study. Very often silencing of expression of a tumor suppressor gene is the result of methylation of cytosine residues in CpG pairs within the gene's promoter region. As WWOX is variably expressed in breast cancer cells, bisulfite genomic sequencing of the WWOX promoter region was performed in several breast cancer cell lines. This analysis was performed on cells which showed the lowest levels of WWOX mRNA, including, BT549, MDA-MB-231, and MDA-MB-435 as well as on cells with high level of WWOX transcription such as, MCF-7 and SKBr-3.

Figure 4:
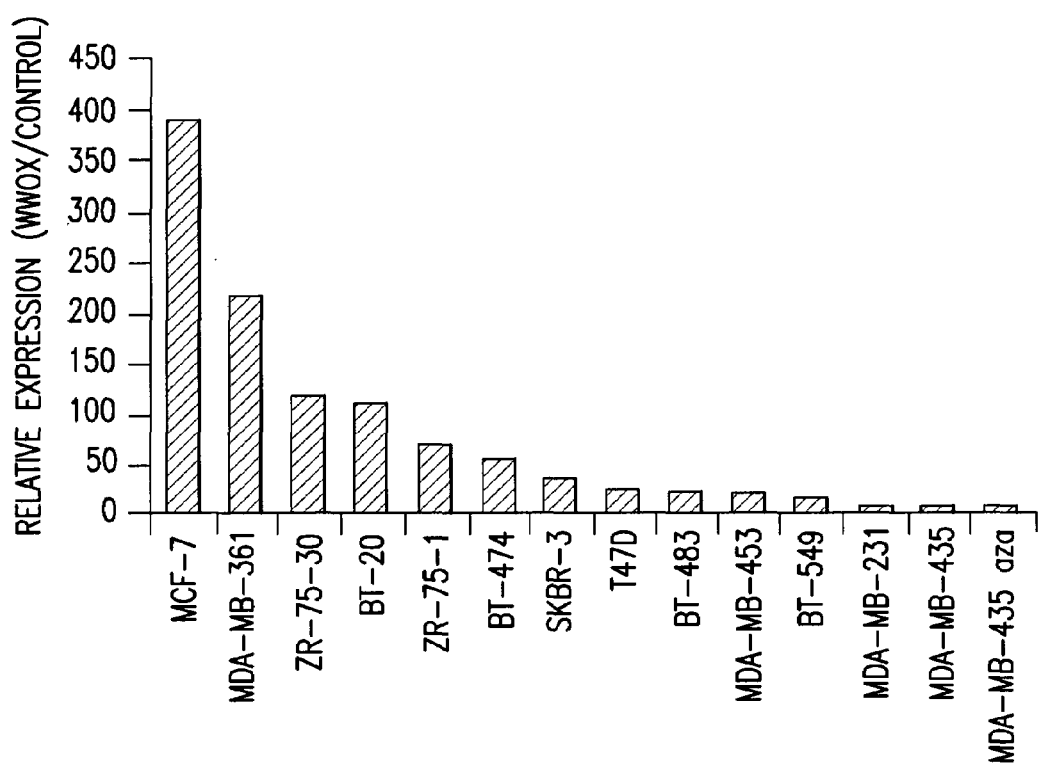
FIG. 4. WWOX mRNA expression in breast cancer cell liness determined by real-time RT-PCR analysis. Levels of WWOX expression are represented as relative to those of the control gene β2-microglobulin.

A CpG rich area surrounding the translation start codon (from −630 to +280) including a putative TATA box (−301 to −292) was sequenced. No CpG methylation was seen in this region. Further, treatment of MDA-MB-435 cells with 5-azacytidine, an inhibitor of CpG methylation, also did not significantly increase the level of WWOX expression (FIG. 4).

Phenotype Analysis of WWOX Transfectants

In vitro studies. It has been previously demonstrated that restoring or increasing the expression of a tumor suppressor gene in cancer cell lines negatively affects anchorage independent growth and/or tumorigenic potential. To determine if increased WWOX expression changes the phenotype of cancer cell lines expressing low levels of WWOX mRNA, recombinant retroviruses carrying the cloned WWOX cDNA were used to transduce the breast cancer cell lines MDA-MB-435 and T47D. Expression of the ectopic WWOX cDNA in transduced cells was confirmed using real-time RT-PCR. WWOX vs. empty vector breast cancer lines transfectants were compared for their ability to grow in monolayer culture and no detectable differences were seen. However, dramatic differences were observed, when the growth of the cells were compared in soft agar. Increased WWOX expression, as a result of ectopic expression, strongly inhibits soft agar growth of MDA-MB-435 cells. The average number of colonies formed by MDA-MB-435/vector cells was 236±33 while MDA-MB-435/WWOX cells formed only 17±3 colonies (P=0.006). Similarly, T47D cells transfected with WWOX showed a dramatic decrease in their ability to grow in soft agar, 14±2 colonies compared to 243±64 colonies formed by T47D/vector cells (P=0.02) (FIG. 5A). In summary, breast cancer cells that ectopically express WWOX formed fewer and much smaller colonies than control cells transfected with vector alone.

In vivo studies. The ability to supress the formation of tumors was also analyzed by in vivo studies. Intramammary fat pad injections were performed in nude mice with the MDA-MB-435/WWOX and MDA-MB-435/vector cells to compare their tumorigenicity. Tumor growth was monitored for 7 weeks and tumor size was measured once per week as described above. Tumors generated by the MDA-MB-435/vector cells were palpable already by seven days post-injection, growing in size rapidly from that point on. On the other hand, for the MDA-MB-435/WWOX injected animals, the first very small tumors were detected by 25 days post-injection, but only in some of the mice. FIG. 5B illustrates dramatic difference in kinetics of tumor growth as determined by caliper size measurements between both groups of animals. At termination of the experiment MDA-MB-435/vector cells formed tumors displaying an average weight of 821±295 mg and tumors forming at all the injection sites (10 out of 10 sites), whereas MDA-MB-435/WWOX cells formed much smaller tumors with an average wet weight of 51±22 mg, with tumors forming at 7 out of 10 sites (FIG. 5C). Such a remarkable difference in the tumor growth rate and size (P=0.00001) demonstrates the strong tumor growth suppressing ability of WWOX.

Analysis of aberrantly spliced WWOX mRNAs. Northern blot analyses from breast, ovarian cancer and multiple myeloma cell lines showed the presence of transcripts of smaller size in some of the cancer cell lines analyzed, which represent abnormal WWOX mRNAs. In order to further characterize other aberrant transcripts, a full length mRNA nested RT-PCR approach was used. Several cancer cell lines showed smaller size amplification products, in addition to the normal PCR product (1422 bp), confirming the northern analysis observations. All such RT-PCR products were isolated and sequenced. Sequencing of the shorter transcripts further confirmed that these are abnormally spliced versions of WWOX. Transcripts displaying deletions of exons 6–8 (WWOXΔ6–8) were detected in MDA-MB-453, MCF-7, HCT116 (colonadenocarcinoma) and AGS (gastric adenocarcinoma) cancer cell lines. A transcript bearing a deletion of exons 5–8 as the highly and only expressed transcript was obtained from KMS11, a multiple myeloma cell line. This deletion found in KMS11 also results in a frame shift. The first 136 out of the 311 amino acids in the new protein are conserved but the following 175 are different than in the wildtype protein. The cDNA sequence of such aberrant transcripts has been reported to GenBank under accession numbers AF395123 and AF395124 respectively. Other aberrant transcripts, displaying no wild-type translation start codon, were found in breast cancer cell lines MDA-MB-157 and MDA-MB-435. In contrast, RT-PCR analysis of several normal breast tissues showed only the wild-type length of WWOX mRNA. Due to the finding of WWOXΔ6–8 aberrant transcripts in breast cancer lines, specific primers were designed to detect this form. To provide specificity the 3'RT-PCR primer was designed to span the abnormal exons 5–9 junction. Using this primer set, cDNAs obtained from a panel of 53 fresh breast cancer samples, were screened to detect the abnormal WWOXΔ6–8 product. The WWOXΔ6–8 aberrant transcript was detected in 17 of the 53 specimens, which represents 32% of the examined tumors. In contrast, the WWOXΔ6–8 transcripts was not detected in any from 18 normal breast adjacent tissue samples tested.

Normal and Abnormal WWOX Cellular Localization. To determine the normal cellular localization of WWOX and to compare this with the localization of proteins resulting from the aberrant transcripts detected in cancer cells, WWOX proteins fused to the green fluorescence protein (GFP) was used. Confocal microscopy analysis of normal breast MCF-10F cells transiently transfected with GFP-WWOX showed that WWOX is cytoplasmic protein localized in distinct perinuclear particles. Dual color detection of GFP-WWOX and a mitochondria specific staining showed no co-localization indicating that WWOX does not localize in the mitochondria. The ability of GFP-WWOX to localize to the Golgi complex was demonstrated by its co-localization with an Golgi specific antibody, the anti-Golgi 58K. This specific antibody binds a Golgi protein epitope located on the Golgi membrane. In order to confirm this finding, GFP-WWOX transfected cells were exposed to Brefeldin A (BFA). BFA is known to cause disassembly of the Golgi complex and redistribution of its contents to the cytoplasm. After BFA treatment, GFP-WWOX was diffusely distributed in the cytoplasm confirming the Golgi localization. After removing BFA from the culture media and allowing a short time for recovery GFP-WWOX again localized within the recovered Golgi apparatus. In contrast to the wild-type WWOX protein localization within the Golgi complex, GFP-WWOXΔ6–8 as well the GFP-WWOXΔ5–8 forms localize to the cell nucleus. These WWOX abnormal proteins display a specific pattern in the nucleus, which may be associated with distinct nuclear particles and/or putative transcription sites.

Discussion

Provided here is evidence demonstrating that WWOX is a tumor suppressor gene when ectopically expressed in breast cancer cells with low or undetectable levels of endogenous expression. WWOX expression induces strong suppression of anchorage independent growth of breast cancer cell lines T47D and MDA-MB-435. More importantly, tumorigenicity of the MDA-MB-435 breast cancer line was dramatically reduced by ectopically expressing WWOX.

In several cancer cell lines and in more than 30% of primary breast tumors expression of aberrant mRNA transcripts of WWOX displaying deletions of exons encoding major portions of the enzymatic WWOX domain, for example, WWOXΔ5–8 and WWOXΔ6–8 were seen. Furthermore, such aberrant transcripts were not detected in any normal tested breast tissues obtained either from normal mammoplasty specimens or normal samples adjacent to tumors. The aberrant proteins resulting from the WWOXΔ5–8 and WWOXΔ6–8 transcripts were found to localize in the cell nucleus in contrast to the normal Golgi complex localization of the wild type protein. The resultant disruption in the catalytic function of the oxidoreductase domain consequential to the deletion of exons 5 or 6 through 8 in addition to the shift in normal cellular localization is believed to dramatically alter the function of WWOX in a cancer cell. It is envisioned that different protein partners could bind to the WW domains of WWOX in the nucleus than in its normal cytoplasmic localization. It is also contemplated that the WWOXΔ6–8 and WWOXΔ5–8 proteins may behave in a dominant negative fashion competing with wild type WWOX for its normal partners and eventually transporting them to the cell nucleus.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,367,110
U.S. Pat. No. 4,452,901
U.S. Pat. No. 4,472,509
U.S. Pat. No. 4,554,101
U.S. Pat. No. 4,683,195
U.S. Pat. No. 4,683,202
U.S. Pat. No. 4,797,368
U.S. Pat. No. 4,800,159
U.S. Pat. No. 4,816,567
U.S. Pat. No. 4,867,973
U.S. Pat. No. 5,021,236
U.S. Pat. No. 5,139,941
U.S. Pat. No. 5,399,363
U.S. Pat. No. 5,466,468
U.S. Pat. No. 5,543,158
U.S. Pat. No. 5,565,332

U.S. Pat. No. 5,641,515
U.S. Pat. No. 5,693,762
U.S. Pat. No. 5,705,629
U.S. Pat. No. 5,846,225
U.S. Pat. No. 5,846,233
Abbondanzo, "Paraffin immunohistochemistry as an adjunct to hematopathology," *Ann Diagn Pathol,* 3(5):318–327, 1999.
Aksentijevich, Pastan, Lunardi-Iskandar, Gallo, Gottesman Thierry, "In vitro and in vivo liposome-mediated gene transfer leads to human MDR1 expression in mouse bone marrow progenitor cells," *Hum Gene Ther,* 7(9):1111–1122, 1996.
Aldaz, Chen, Sahin, Cunningham, Bondy, "Comparative allelotype of in situ and invasive human breast cancer: high frequency of microsatellite instability in lobular breast carcinomas," *Cancer Res.,* 55:3976–3981, 1995.
Allred, Bustamante, Daniel, Gaskill, Cruz Jr., "Immunocytochemical analysis of estrogen receptors in human breast carcinomas. Evaluation of 130 cases and review of the literature regarding concordance with biochemical assay and clinical relevance," *Arch Surg,* 125(1):107–13, 1990.
Andre and Springael, "WWP, a new amino acid motif present in single or multiple copies in various proteins including dystrophin and the SH3-binding Yes-associated protein YAP65," *Biochem. Biophys. Res. Commun.,* 205: 1201–1205, 1994.
Angel, Bauman, Stein, Dellus, Rahmsdorf, and Herrlich, "12-0-tetradecanoyl-phorbol-13-acetate induction of the human collagenase gene is mediated by an inducible enhancer element located in the 5' flanking region," *Mol. Cell. Biol.,* 7:2256, 1987.
Angel, Imagawa, Chiu, Stein, Imbra, Rahmsdorf, Jonat, Herrlich, and Karin, "Phorbol ester-inducible genes contain a common cis element recognized by a TPA-modulated trans-acting factor," *Cell,* 49:729, 1987
Antibodies: A Laboratory Manual, Cold Spring Harbor Laboratory, 1988
Atchison and Perry, "Tandem κ immunoglobulin promoters are equally active in the presence of the κ enhancer: Implications for model of enhancer function," *Cell,* 46:253, 1986.
Atchison and Perry, "The role of the κ enhancer and its binding factor nf-κ β in the developmental regulation of κ gene transcription," *Cell,* 48:121, 1987.
Baichwal and Sugden, In: *Gene Transfer*, Kucherlapati (ed.), New York, Plenum Press, 117–148, 1986.
Bakhshi, Jensen, Goldman, Wright, McBride, Epstein, Korsmeyer, "Cloning the chromosomal breakpoint of t(14;18) human lymphomas: clustering around JH on chromosome 14 and near a transcriptional unit on 18," *Cell,* 41(3): 899–906, 1985.
Banerji, Olson, Schaffner, "A lymphocyte-specific cellular enhancer is located downstream of the joining region in immunoglobulin heavy chain genes," *Cell,* 33(3):729–740, 1983.
Banerji, Rusconi, Schaffner, "Expression of a β-globin gene is enhanced by remote SV40 DNA sequences," *Cell,* 27(2 Pt 1):299–308, 1981.
Bedford, Reed, Leder, "WW domain-mediated interactions reveal a spliceosome-associated protein that binds a third class of proline-rich motif: the proline glycine and methionine-rich motif," *Proc. Natl. Acad. Sci. USA,* 95:10602–10607, 1998.
Bednarek and Aldaz, "Characterization of transcripts from a commonly deleted area of chromosome 16 (q23.3–q24.1) in human breast cancer," *Proc. Amer. Assoc. Cancer Res.,* 872, 1998.
Bednarek, Laflin, Daniel, Liao, Hawkins, Aldaz, "WWOX, a novel WW domain-containing protein mapping to human chromosome 16q23.3–24.1, a region frequently affected in breast cance," *Cancer Res.,* 60(8):2140–2145, 2000.
Berkhout, Silverman, Jeang, "Tat trans-activates the human immunodeficiency virus through a nascent RNA target," *Cell,* 59:273–282, 1989.
Blanar, Baldwin, Flavell, and Sharp, "A gamma-interferon-induced factor that binds the interferon response sequence of the MHC class I gene, H-2Kb," *EMBO J,* 8:1139, 1989.
Bodine and Ley, "An enhancer element lies 3' to the human a gamma globin gene," *EMBO J,* 6:2997, 1987.
Bork and Sudol, "The WW domain: a signalling site in dystrophin?" *Trends Biochem. Sci.,* 19:531–533, 1994.
Boshart, Weber, Jahn, Dorsch-Hasler, Fleckenstein, and Schaffner, "A very strong enhancer is located upstream of an immediate early gene of human cytomegalovirus," *Cell,* 41:521, 1985.
Bosze, Thiesen, Charnay, "A transcriptional enhancer with specificity for erythroid cells is located in the long terminal repeat of the Friend murine leukemia virus," *EMBO J,* 5(7):1615–1623, 1986.
Braddock, Chambers, Wilson, Esnouf, Adams, Kingsman, and Kingsman, "HIV-I Tat activates presynthesized RNA in the nucleus," *Cell,* 58:269, 1989.
Brown, Linsley, Horn, "Development and evaluation of monoclonal antibody-based immunoassays: breast carcinoma-associated mucins as tumor markers," *Immunol Ser,* 53:69–82, 1990.
Bulla and Siddiqui, "The hepatitis B virus enhancer modulates transcription of the hepatitis B virus surface-antigen gene from an internal location," *J. Virol.,* 62:1437, 1986.
Caldas, Hahn, da Costa, Redston, Schutte, Seymour, Weinstein, Hruban, Yeo, Kern, "Frequent somatic mutations and homozygous deletions of the p16 (MTS1) gene in pancreatic adenocarcinoma," *Nat. Genet.,* 8(1):27–32, 1994.
Caley, Betts, Irlbeck, Davis, Swanstrom, Frelinger, Johnston, "Humoral, mucosal, and cellular immunity in response to a human immunodeficiency virus type 1 immunogen expressed by a Venezuelan equine encephalitis virus vaccine vector," *J Virol,* 71(4):3031–3038, 1997.
Campbell and Villarreal, "Functional analysis of the individual enhancer core sequences of polyoma virus: cell-specific uncoupling of DNA replication from transcription," *Mol. Cell. Biol.,* 8:1993, 1988.
Campere and Tilghman, "Postnatal repression of the α-fetoprotein gene is enhancer independent," *Genes and Dev.,* 3:537, 1989.
Campo, Spandidos, Lang, Wilkie, "Transcriptional control signals in the genome of bovine papilloma virus type 1," *Nature,* 303:77, 1983.
Capaldi, Bell, Branchek, "Changes in order of migration of polypeptides in complex III and cytochrome C oxidase under different conditions of SDS polyacrylamide gel electrophoresis," *Biochem. Biophys. Res. Comm.,* 74(2): 425–433, 1977.
Carter, Ewing, Ward, Treiger, Aalders, Schalken, Epstein, Isaacs, "Allelic loss of chromosomes 16q and 10q in human prostate cancer," *Proc. Natl. Acad. Sci. USA,* 87: 8751–8755, 1990.

Celander and Haseltine, "Glucocorticoid regulation of murine leukemia virus transcription elements is specified by determinants within the viral enhancer region," *J. Virology*, 61:269, 1987.

Celander, Hsu, and Haseltine, "Regulatory Elements Within the Murine Leukemia Virus Enhancer Regions Mediate Glucocorticoid Responsiveness," *J. Virology*, 62:1314, 1988.

Chandler, Maler, and Yamamoto, "DNA sequences bound specifically by glucocorticoid receptor in vitro render a heterlogous promoter hormone responsive in vivo," *Cell*, 33:489, 1983.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chatterjee, Lee, Rentoumis, and Jameson, "Negative regulation of the thyroid-stimulating hormone alpha gene by thyroid hormone: receptor interaction adjacent to the TATA box," *Proc Natl. Acad. Sci. U.S.A.*, 86:9114, 1989.

Chen and Okayama, "High-efficiency transformation of mammalian cells by plasmid DNA," *Mol. Cell Biol.*, 7(8):2745–2752, 1987.

Chen and Sudol, "The WW domain of Yes-associated protein binds a proline-rich ligand that differs from the consensus established for Src homology 3-binding modules," *Proc. Natl. Acad. Sci. USA*, 92:7819–7823, 1995.

Chen, Sahin, Aldaz, "Deletion map of chromosome 16q in ductal carcinoma in situ of the breast: refining a putative tumor suppressor gene region," *Cancer Res.* 56: 5605–5609, 1996.

Cheng, Jhanwar, Klein, Bell, Lee, Altomare, Nobori, Olopade, Buckler, Testa Jr., "p16 alterations and deletion mapping of 9p21–p22 in malignant mesothelioma," *Cancer Res.*, 54(21):5547–5551, 1994.

Chesi, Bergsagel, Shonukan, Martelli, Brents, Chen, Schrock, Ried, Kuehl, "Frequent dysregulation of the c-maf proto-oncogene at 16q23 by translocation to an Ig locus in multiple myeloma," *Blood*, 91:4457–4463, 1998.

Choi, Chen, Kriegler, and Roninson, "An altered pattern of cross-resistance in multi-drug-resistant human cells results from spontaneous mutations in the mdr-1 (p-glycoprotein) gene," *Cell*, 53:519, 1988.

Clark, Harrison, Paul, Frommer, "High sensitivity mapping of methylated cytosines," *Nucleic Acids Res*, 22(15): 2990–2997, 1994.

Clark, Voulgaropoulou, Fraley, Johnson, "Cell lines for the production of recombinant adeno-associated virus," *Hum. Gene Ther.*, 6(10):1329–1341, 1995.

Cleary and Sklar, "Nucleotide sequence of a t(14;18) chromosomal breakpoint in follicular lymphoma and demonstration of a breakpoint-cluster region near a transcriptionally active locus on chromosome 18," *Proc. Natl. Acad. Sci. USA*, (21):7439–7443, 1985.

Cleary et al., *J. Exp. Med.*, 164(1):315–320, 1986.

Cleton-Jansen, Moerland, Kuipers-Dijkshoorn, Callen, Sutherland, Hansen, Devilee, Cornelisse, "At least two different regions are involved in allelic imbalance on chromosome arm 16q in breast cancer," *Genes, Chromos, Cancer*, 9:101–107, 1994.

Coffin, Retroviridae and Their Replication. In: *Virology*, Fields et al., eds., Raven Press, New York, pp. 1437–1500, 1990.

Cohen, Walter, and Levinson, "A Repetitive Sequence Element 3' of the Human c-Ha-ras1 Gene Has Enhancer Activity," *J. Cell. Physiol.*, 5:75, 1987.

Costa, Lai, Grayson, and Darnell, "The cell-specific enhancer of the mouse transthyretin (prealbumin) gene binds a common factor at one site and a liver-specific factor(s) at two other sites," *Mol. Cell. Biol.*, 8:81–90, 1988.

Coupar, Andrew, Boyle, "A general method for the construction of recombinant vaccinia viruses expressing multiple foreign genes," *Gene*, 68:1–10, 1988.

Crawford, Ianzano, Savino, Whitmore, Cleton-Jansen, Settasatian, d'apolito, Seshadri, Pronk, Auerbach, Verlander, Mathew, Tipping, Doggett, Zelante, Callen, Savoia, "The PISSLRE gene: structure, exon skipping, and exclusion as tumor suppressor in breast cancer," *Genomics*, 56:90–97, 1999.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J*, 6:3745, 1987.

Culotta and Hamer, "Fine Mapping of a Mouse Metallothionein Gene Metal-Response Element," *Mol. Cell. Biol.*, 9:1376–1380, 1989.

Dandolo, Blangy, and Kamen, "Regulation of Polyma Virus Transcription in Murine Embryonal Carcinoma Cells," *J. Virology*, 47:55–64, 1983.

Davis et al., "A viral vaccine vector that expresses foreign genes in lymph nodes and protects against mucosal challenge," *J. Virol.*, Jun; 70(6):3781–7, 1996.

De Villiers, Schaffner, Tyndall, Lupton, and Kamen, "Polyoma Virus DNA Replication Requires an Enhancer," *Nature*, 312(5991):242–246, 1984.

Deschamps, Meijlink, and Verma, "Identification of a transcriptional enhancer element upstream from the proto-oncogene fos," *Science*, 230:1174–1177, 1985.

Duax and Ghosh, "Structure and function of steroid dehydrogenases involved in hypertension, fertility, and cancer," *Steroids*, 62:95–100, 1997.

Dutrillaux, Gerbault-Seureau, Zafrani, "Characterization of chromosomal anomalies in human breast cancer. A comparison of 30 paradiploid cases with few chromosome changes," *Cancer Genet. Cytogenet.*, 49:203–217, 1990.

Edbrooke, Burt, Cheshire, and Woo, "Identification of cis-acting sequences responsible for phorbol ester induction of human serum amyloid a gene expression via a nuclear-factor-kappa β-like transcription factor," *Mol. Cell. Biol.*, 9:1908–1916, 1989.

Edlund, Walker, Barr, and Rutter, "Cell-specific expression of the rat insulin gene: evidence for role of two distinct 5' flanking elements," *Science*, 230:912–916, 1985.

European Patent No. EP266,032

Fechheimer, Boylan, Parker, Sisken, Patel, Zimmer, "Transfection of mammalian cells with plasmid DNA by scrape loading and sonication loading," *Proc. Nat'l Acad. Sci. USA*, 84:8463–8467, 1987.

Felgner, Gadek, Holm, Roman, Chan, Wenz, Northrop, Ringold, Danielsen, "Lipofection: a highly efficient, lipid-mediated DNA-transfection procedure," *Proc Natl Acad Sci USA*, 84(21):7413–7, 1987.

Feng and Holland, "HIV-I Tat Trans-Activation Requires the Loop Sequence Within Tar," *Nature*, 334:6178, 1988.

Firak and Subramanian, "Minimal Transcription Enhancer of Simian Virus 40 is a 74-Base-Pair Sequence that Has Interacting Domains," *Mol. Cell. Biol.*, 6:3667, 1986.

Flotte, Afione, Conrad, McGrath, Solow, Oka, Zeitlin, Guggino, Carter, "Stable in vivo expression of the cystic fibrosis transmembrane conductance regulator with an adeno-associated virus vector," *Proc Natl Acad Sci USA*, 90(22):10613–7, 1993.

Flotte, Solow, Owens, Afione, Zeitlin, Carter, "Gene expression from adeno-associated virus vectors in airway epithelial cells," *Am J Respir Cell Mol Biol*, 7(3):349–356, 1992.

Foecking and Hofstetter, "Powerful and Versatile Enhancer-Promoter Unit for Mammalian Expression Vectors," *Gene*, 45(1):101–105, 1986.

Fraley, Fornari, Kaplan, "Entrapment of a bacterial plasmid in phospholipid vesicles: potential for gene transfer," *Proc. Nat'l Acad. Sci. USA*, 76:3348–3352, 1979.

Friedmann, "Progress toward human gene therapy", *Science*, 244:1275–1281, 1989.

Froehler et al., "Synthesis of DNA via deoxynucleoside H-phosphonate intermediates." *Nucleic Acids Res*, Jul 11;14(13):5399–407, 1986.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Futreal, Cochran, Rosenthal, Miki, Swenson, Hobbs, Bennett, Haugen-Strano, Marks, Barrett et al., "Isolation of a diverged homeobox gene, MOX1, from the BRCA1 region on 17q21 by solution hybrid capture," *Hum. Mol Genet.*, 3:1359–1364, 1994.

Gabizon, Price, Huberty, Bresalier, Papahadjopoulos, "Effect of liposome composition and other factors on the targeting of liposomes to experimental tumors: biodistribution and imaging studies," *Cancer Res*, 50(19):6371–8, 1996.

Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87–104, 1991.

Gilles, Morris, Oi, and Tonegawa, "A tissue-specific transcription enhancer element is located in the major intron of a rearranged immunoglobulin heavy-chain gene," *Cell*, 33:717, 1983.

Gloss, Bernard, Seedorf, and Klock, "The upstream regulatory region of the human papilloma virus-16 contains an E2 protein-independent enhancer which is specific for cervical carcinoma cells and regulated by glucocorticoid hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goding, In: *Monoclonal Antibodies: Principles and Practice*, 2d ed., Academic Press, Orlando, Fla., pp. 60–61, and 71–74, 1986.

Gomez-Foix et al., *J. Biol. Chem.*, 267:25129–25134, 1992.

Goodbourn and Maniatis, "Overlapping Positive and Negative Regulatory Domains of the Human β-Interferon Gene," *Proc. Natl. Acad. Sci. USA*, 85:1447, 1988.

Goodbourn, Burstein, and Maniatis, "The Human Beta-Interferon Gene Enhancer is Under Negative Control," *Cell*, 45:601, 1986.

Gopal, "Gene transfer method for transient gene expression, stable transformation, and cotransformation of suspension cell cultures," *Mol. Cell Biol.*, 5:1188–1190, 1985.

Graham and Prevec, "Adenovirus-based expression vectors and recombinant vaccines," *Biotechnology*, 20:363–390, 1992.

Graham and van der Eb, "A new technique for the assay of infectivity of human adenovirus 5 DNA," *Virology*, 52:456–467, 1973.

Greene, Bohnlein, and Ballard, "HIV-1, and Normal T-Cell Growth: Transcriptional Strategies and Surprises," *Immunology Today*, 10:272, 1989

Grosschedl and Baltimore, "Cell-type specificity of immunoglobulin gene expression is regulated by at least three dna sequence elements," *Cell*, 41:885, 1985.

Grunhaus, Cho, Horwitz, "Association of vaccinia virus-expressed adenovirus E3-19K glycoprotein with class I MHC and its effects on virulence in a murine pneumonia model," *Seminar in Virology*, 200(2):535–546, 1992.

Hanes et al., *Yeast*, 5:55–72, 1989.

Harland and Weintraub, "Translation of mRNA injected into *Xenopus* oocytes is specifically inhibited by antisense RNA," *J. Cell Biol.*, 101: 1094–1099, 1985.

Haslinger and Karin, "Upstream Promoter Element of the Human Metallothionein-II Gene Can Act Like an Enhancer Element," *Proc Natl. Acad. Sci. U.S.A.*, 82:8572, 1985.

Hauber and Cullen, "Mutational Analysis of the Trans-Activiation-Responsive Region of the Human Immunodeficiency Virus Type I Long Terminal Repeat," *J. Virology*, 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321: 249, 1986.

Hensel, Meichle, Pfizenmaier, and Kronke, "PMA-responsive 5' flanking sequences of the human TNF gene," *Lymphokine Res.*, 8:347, 1989.

Hermonat and Muzycska, "Use of adeno-associated virus as a mammalian DNA cloning vector: transduction of neomycin resistance into mammalian tissue culture cells," *Proc. Nat'l Acad. Sci. USA*, 81:6466–6470, 1984.

Herr and Clarke, "The SV40 Enhancer is Composed of Multiple Functional Elements That Can Compensate for One Another," *Cell*, 45:461, 1986.

Hersdorffer et al., *DNA Cell Biol.*, 9:713–723, 1990.

Herz and Gerard, *Proc. Nat'l Acad. Sci. USA*, 90:2812–2816, 1993.

Hirochika, Browker, and Chow, "Enhancers and Trans-Acting E2 Transcriptional Factors of Papilloma Viruses," *J. Virol.*, 61:2599, 1987.

Hirsch, Gaugler, Deagostini-Bauzin, Bally-Cuif, and Gordis, "Identification of positive and negative regulatory elements governing cell-type-specific expression of the neural-cell-adhesion-molecule gene," *Mol. Cell. Biol.*, 10:1959, 1990.

Ho et al., Internal radiation therapy for patients with primary or metastatic hepatic cancer: a review. *Cancer.* Nov 1;83(9):1894–907, 1998.

Hoffman and Bucher, *FEBS Lett.*, 358:153–157, 1995a.

Hofmann and Bucher, "The FHA domain: a putative nuclear signalling domain found in protein kinases and transcription factors [letter]," *Trends Biochem. Sci.*, 20:347–349, 1995b.

Holbrook, Gulino, and Ruscetti, "cis-Acting Transcriptional Regulatory Sequences in the Gibbon Ape Leukemia Virus (GALV) Long Terminal Repeat," *Virology*, 157:211, 1987.

Horlick and Benfield, "The Upstream Muscle-Specific Enhancer of the Rat Muscle Creatine Kinase Gene is Composed of Multiple Elements," *Mol. Cell. Biol.*, 9:2396, 1989.

Horwich, Furtak, Pugh, Summers, "Synthesis of hepadnavirus particles that contain replication-defective duck hepatitis B virus genomes in cultured HuH7 cells," *Virol.*, 64:642–650, 1990.

Huang, Ostrowski, Berard, and Hagar, "Glucocorticoid regulation of the ha-musv p21 gene conferred by sequences from mouse mammary tumor virus," *Cell*, 27:245, 1981.

Hug, Costas, Staeheli, Aebi, and Weissmann, "Organization of the Murine Mx Gene and Characterization of its Interferon- and Virus-Inducible Promoter," *Mol. Cell. Biol.*, 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa, Chiu, and Karin, "Transcription Factor AP-2 Mediates Induction by Two Different Signal-Transduction Pathways: Protein Kinase C and cAMP," *Cell*, 51:251, 1987.

Imbra and Karin, "Phorbol Ester Induces the Transcriptional Stimulatory Activity of the SV40 Enhancer," *Nature*, 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.*, 8:62, 1988.

Johnson, Wold, and Hauschka, "Muscle creatine kinase sequence elements regulating skeletal and cardiac muscle expression in transgenic mice," *Mol. Cell. Biol.*, 9:3393, 1989.

Jornvall, Persson, Krook, Atrian, Gonzalez-Duarte, Jeffery, Ghosh, "Short-chain dehydrogenases/reductases (SDR)," *Biochemistry*, 34:6003–6013, 1995.

Kadesch and Berg, "Effects of the Position of the Simian Virus 40 Enhancer on Expression of Multiple Transcription Units in a Single Plasmid," *Mol. Cell. Biol.*, 6:2593, 1986.

Kamb, Shattuck-Eidens, Eeles, Liu, Gruis, Ding, Hussey, Tran, Miki, Weaver-Feldhaus et al., "Analysis of the p16 gene (CDKN2) as a candidate for the chromosome 9p melanoma susceptibility locus," *Nat. Genet.*, 8(1):23–2, 1994.

Kaneda, Iwai, Uchida, "Increased expression of DNA cointroduced with nuclear protein in adult rat liver," *Science*, 243:375–378, 1989.

Karin, Haslinger, Heguy, Dietlin, and Cooke, "Metal-Responsive Elements Act as Positive Modulators of Human Metallothionein-IIA Enhancer Activity," *Mol. Cell. Biol.*, 7:606, 1987.

Katinka, Vasseur, Montreau, Yaniv, and Blangy, "Polyoma DNA Sequences Involved in the Control of Viral Gene Expression in Murine Embryonal Carcinoma Cells," *Nature*, 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell*, 20:393, 1980.

Kato et al., *J. Biol. Chem.*, 266:3361–3364, 1991.

Kawamoto, Makino, Niw, Sugiyama, Kimura, Anemura, Nakata, and Kakunaga, "Identification of the Human Beta-Actin Enhancer and its Binding Factor," *Mol. Cell. Biol.*, 8:267, 1988.

Kerr, Wyllie, Currie, "Apoptosis: a basic biological phenomenon with wide-ranging implications in tissue kinetics," *Br. J. Cancer*, 26(4):239–257, 1972.

Kiledjian, Su, Kadesch, "Identification and characterization of two functional domains within the murine heavy-chain enhancer," *Mol. Cell. Biol.*, 8:145, 1988.

Klamut, Gangopadyhay, Worton, and Ray, "Molecular and Functional Analysis of the Muscle-Specific Promoter Region of the Duchenne Muscular Dystrophy Gene," *Mol. Cell. Biol.*, 10:193, 1990.

Klein et al., *Nature*, 327:70–73, 1987.

Koch, Benoist, and Mathis, "Anatomy of a new β-cell-specific enhancer," *Mol. Cell. Biol.*, 9:303, 1989.

Kotin, Siniscalco, Samulski, Zhu, Hunter, Laughlin, McLaughlin, Muzyczka, Rocchi, Berns, "Site-specific integration by adeno-associated virus," *Proc Natl Acad Sci USA*, 1990 March;87(6):2211–5, 1990.

Kozak, "Interpreting cDNA sequences: some insights from studies on translation," *Mamm. Genome.*, 7:563–574, 1996.

Kriegler and Botchan, "A retrovirus LTR contains a new type of eukaryotic regulatory element," In: *Eukaryotic Viral Vectors*, Gluzman (ed.), Cold Spring Harbor, Cold Spring Harbor Laboratory, NY, 1982.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler et al., "Promoter substitution and enhancer augmentation increases the penetrance of the sv40 a gene to levels comparable to that of the harvey murine sarcoma virus ras gene in morphologic transformation," In: *Gene Expression*, Alan Liss (Ed.), Hamer and Rosenberg, New York, 1983.

Kriegler et al., "Viral Integration and Early Gene Expression Both Affect the Efficiency of SV40 Transformation of Murine Cells: Biochemical and Biological Characterization of an SV40 Retrovirus," In: *Cancer Cells 2/Oncogenes and Viral Genes*, Van de Woude et al. eds, Cold Spring Harbor: Cold Spring Harbor Laboratory, 1984.

Kriegler, Perez, Hardy and Botchan, "Transformation mediated by the sv40 t antigens: separation of the overlapping sv40 early genes with a retroviral vector," *Cell*, 38:483, 1984.

Kuhl, De La Fuenta, Chaturvedi, Parinool, Ryals, Meyer, and Weissman, "Reversible Silencing of Enhancers by Sequences Derived From the Human IFN-alpha Promoter," *Cell*, 50:1057, 1987.

Kumar et al., *Biochem. Biophys. Res. Comm.*, 185:115–1161, 1992.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.*, 17:1121, 1989.

Kyte and Doolittle, "A simple method for displaying the hydropathic character of a protein," *J Mol Biol*, 57(1): 105–32, 1982.

LaFace, Hermonat, Wakeland, Peck, "Gene transfer into hematopoietic progenitor cells mediated by an adeno-associated virus vector," *Virology*, 162(2):483–486, 1988.

Landis, Murray, Bolden, Wingo., "Cancer statistics, 1998," *CA Cancer J Clin*, 48(1):6–29, 1998.

Larsen, Harney, and Moore, "Repression medaites cell-type-specific expression of the rat growth hormone gene," *Proc Natl. Acad. Sci. USA.*, 83:8283, 1986.

Laspia, Rice, and Mathews, "HIV-1 Tat protein increases transcriptional initiation and stabilizes elongation," *Cell*, 59:283, 1989.

Latimer, Berger, and Baumann, "Highly conserved upstream regions of the alpha.sub.1-antitrypsin gene in two mouse species govern liver-specific expression by different mechanisms," *Mol. Cell. Biol.*, 10:760, 1990.

Laughlin, Cardellichio, Coon, "Latent infection of KB cells with adeno-associated virus type 2," *J Virol*, 60(2):515–24, 1986.

Le Gal La Salle et al., *Science*, 259:988–990, 1993.

Lebkowski et al., *Mol Cell Biol*, 8(10):3988–3996, 1988.

Lee, Mulligan, Berg, and Ringold, "Glucocorticoids Regulate Expression of Dihydrofolate Reductase cDNA in Mouse Mammary Tumor Virus Chimaeric Plasmids," *Nature*, 294:228, 1981.

Levine et al., "The spectrum of mutations at the p53 locus. Evidence for tissue-specific mutagenesis, selection of mutant alleles, and a "gain of function" phenotype," *Ann N Y Acad Sci*. Sep 30;768:111–28, 1995.

Levinson, Khoury, VanDeWoude, and Gruss, "Activation of SV40 Genome by 72-Base-Pair Tandem Repeats of Moloney Sarcoma Virus," *Nature*, 295:79, 1982.

Levrero et al., *Gene*, 101:195–202, 1991.

Lin, Cross, Halden, Dragos, Toledano, and Leonard, "Delineation of an enhancerlike positive regulatory element in the interleukin-2 receptor .alpha.-chain gene," *Mol. Cell. Biol.*, 10:850, 1990.

Lu, Hanes, Hunter, "A human peptidyl-prolyl isomerase essential for regulation of mitosis," *Nature*, 380:544–547, 1996.

Lu, Zhou, Shen, Lu, "Function of WW domains as phosphoserine- or phosphothreonine-binding modules," *Science*, 283:1325–1328, 1999.

Luria, Gross, Horowitz, and Givol, "Promoter Enhancer Elements in the Rearranged Alpha-Chain Gene of the Human T-Cell Receptor," *EMBO J.*, 6:3307, 1987.

Lusky and Botchan, "Transient Replication of Bovine Papilloma Virus Type 1 Plasmids: cis and trans Requirements," *Proc Natl. Acad. Sci. U.S.A.*, 83:3609, 1986.

Lusky, Berg, Weiher, and Botchan, "Bovine Papilloma Virus Contains an Activator of Gene Expression at the Distal End of the Early Transcription Unit," *Mol. Cell. Biol.* 3:1108, 1983.

Macejak and Sarnow, "Internal initiation of translation mediated by the 5' leader of a cellular mRNA," *Nature*, 353:90–94, 1991.

Majors and Varmus, "A small region of the mouse mammary tumor virus long terminal repeat confers glucocorticoid hormone regulation on a linked heterologous gene," *Proc. Natl. Acad. Sci. USA*, 80:5866, 1983.

Maleszka, Hanes, Hackett, de Couet, Miklos, "The *Drosophila melanogaster* dodo (dod) gene, conserved in humans, is functionally interchangeable with the ESS1 cell division gene of *Saccharomyces cerevisiae*," *Proc. Natl. Acad. Sci. USA*, 93:447–451, 1996.

Mangelsdorf, M., K. Ried, E. Woollatt, S. Dayan, H. Eyre, M. Finnis, L. Hobson, J. Nancarrow, D. Venter, E. Baker & R. I. Richards Chromosomal fragile site FRA16D and DNA instability in cancer. *Cancer Res.*, 60:1683–1689, 2000.

Mann, Mulligan, Baltimore, "Construction of a retrovirus packaging mutant and its use to produce helper-free defective retrovirus," *Cell*, 33:153–159, 1983.

Markowitz et al., *J. Virol.*, 62:1120–1124, 1988.

Mayer et al., Chemotherapy of resistant and recurrent lymphoma based on a combination of ifosfamide and etoposide. Antitumor effects, toxicity and stimulation of peripheral stem cells]. *Cas Lek Cesk.* Oct 5;137(19):590–7, Czech, 1998.

McCarty, Christensen, Muzyczka, "Sequences required for coordinate induction of adeno-associated virus p19 and p40 promoters by Rep protein," *J Virol*, 65(6):2936–45, 1991.

McLaughlin, Collis, Hermonat, Muzyczka, "Adeno-associated virus general transduction vectors: analysis of proviral structures," *J Virol*, 62(6):1963–73, 1988.

McNeall, Sanchez, Gray, Chesterman, and Sleigh, "Hyperinducible Gene Expression From a Metallotionein Promoter Containing Additional Metal-Responsive Elements," *Gene*, 76:81, 1989.

Miksicek, Heber, Schmid, Danesch, Posseckert, Beato, and Schutz, "Glucocorticoid Responsiveness of the Transcriptional Enhancer of Moloney Murine Sarcoma Virus," *Cell*, 46:203, 1986.

Mitas et al., "Quantitative real-time RT-PCR detection of breast cancer micrometastasis using a multigene marker panel," *Int J Cancer.* Jul 15;93(2):162–71, 2001.

Mordacq and Linzer, "Co-localization of elements required for phorbol ester stimulation and glucocorticoid repression of proliferin gene expression," *Genes and Dev.*, 3:760, 1989.

Moreau, Hen, Wasylyk, Everett, Gaub, and Chambon, "The SV40 base-repair repeat has a striking effect on gene expression both in sv40 and other chimeric recombinants," *Nucl. Acids Res.*, 9:6047, 1981.

Musesing, Smith, and Capon, "Regulation of mRNA Accumulation by a Human Immunodeficiency Virus Trans-Activator Protein," *Cell*, 48:691, 1987.

Muzyczka, "Use of adeno-associated virus as a general transduction vector for mammalian cells," *Curr Top Microbiol Immunol*, 158:97–129, 1992.

Nakai and Kanehisa, "A knowledge base for predicting protein localization sites in eukaryotic cells," *Genomics*, 14:897–911, 1992.

Ng, Gunning, Liu, Leavitt, and Kedes, "Regulation of the Human Beta-Actin Promoter by Upstream and Intron Domains," *Nuc. Acids Res.*, 17:601, 1989.

Nicolas and Rubinstein, In: *Vectors: A survey of molecular cloning vectors and their uses*, Stoneham: Butterworth, pp. 494–513, 1988.

Nicolau and Sene, "Liposome-mediated DNA transfer in eukaryotic cells. Dependence of the transfer efficiency upon the type of liposomes used and the host cell cycle stage," *Biochim. Biophys. Acta*, 721:185–190, 1982.

Nicolau, Legrand, Grosse, "Liposomes as carriers for in vivo gene transfer and expression," *Methods Enzymol.*, 149: 157–176, 1987.

Nobori, Miura, Wu, Lois, Takabayashi, Carson, "Deletions of the cyclin-dependent kinase-4 inhibitor gene in multiple human cancers," *Nature*, 368(6473):753–756, 1994.

Ohara, Dorit, Gilbert, "One-sided polymerase chain reaction: the amplification of cDNA," *Proc. Nat'l Acad. Sci. USA,* 86: 5673–5677, 1989.

Ohi, Dixit, Tillery, Plonk, "Construction and replication of an adeno-associated virus expression vector that contains human beta-globin cDNA," *Gene,* 89(2):279–282, 1990.

Okamoto et al., "Mutations and altered expression of p16INK4 in human cancer. *Proc Natl Acad Sci USA.,* Nov 8;91(23):11045–9, 1994.

Omitz, Hammer, Davison, Brinster, and Palmiter, "Promoter and enhancer elements from the rat elastase i gene function independently of each other and of heterologous enhancers," *Mol. Cell. Biol.* 7:3466, 1987.

Ondek, Sheppard, and Herr, "Discrete Elements Within the SV40 Enhancer Region Display Different Cell-Specific Enhancer Activities," *EMBO J.,* 6:1017, 1987.

Orlow, Lianes, Lacombe, Dalbagni, Reuter, Cordon-Cardo, "Chromosome 9 allelic losses and microsatellite alterations in human bladder tumors,", *Cancer Res,* 54(11): 2848–2851, 1994.

Paige, A. J., K. J. Taylor, A. Stewart, J. G. Sgouros, H. Gabra, G. C. Sellar, J. F. Smyth, D. J. Porteous & J. E. Watson, "A 700-kb physical map of a region of 16q23.2 homozygously deleted in multiple cancers and spanning the common fragile site FRA16D," *Cancer Res.* 60: 1690–1697, 2000.

Palmiter, Chen, and Brinster, "Differential regulation of metallothionein-thymidine kinase fusion genes in transgenic mice and their offspring," *Cell,* 29:701, 1982.

Pandis, Heim, Bardi, Idvall, Mandahl, Mitelman, "Whole-arm t(1;16) and i(1q) as sole anomalies identify gain of 1q as a primary chromosomal abnormality in breast cancer," *Genes Chromosomes Cancer,* 5:235–238, 1992.

Paskind, Weinberg, Baltimore, "Dependence of Moloney murine leukemia virus production on cell growth," *Virology,* 67:242–248, 1975.

Pech, Rao, Robbins, and Aaronson, "Functional identification of regulatory elements within the promoter region of platelet-derived growth factor 2," *Mol. Cell Biol.,* 9:396, 1989.

Pelletier and Sonenberg, "Internal initiation of translation of eukaryotic mRNA directed by a sequence derived from poliovirus RNA," *Nature,* 334(6180):320–325, 1988.

Perez-Stable and Constantini, "Roles of fetal y-globin promoter elements and the adult β-globin 3' enhancer in the stage-specific expression of globin genes," *Mol. Cell. Biol.,* 10:1116, 1990.

Picard and Schaffner, "A lymphocyte-specific enhancer in the mouse immunoglobulin kappa gene," *Nature,* 307:83, 1984.

Pinkert, Omitz, Brinster, and Palmiter, "An albumin enhancer located 10 kb upstream functions along with its promoter to direct efficient, liver-specific expression in transgenic mice," *Genes and Dev.,* 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.,* 82:1020, 1985.

Porton, Zaller, Lieberson, and Eckhardt, "Immunoglobulin heavy-chain enhancer is required to maintain transfected .gamma.2a gene expression in a pre-b-cell line," *Mol. Cell. Biol.,* 10:1076, 1990.

Potter, Weir, Leder, "Enhancer-dependent expression of human kappa immunoglobulin genes introduced into mouse pre-B lymphocytes by electroporation," *Proc. Nat'l Acad. Sci. USA,* 81:7161–7165, 1984.

Price, J. E., Polyzos, A., Zhang, R. D., and Daniels, L. M., "Tumorigenicity and metastasis of human breast carcinoma cell lines in nude mice," *Cancer Res.* 50:717–21, 1990.

Queen and Baltimore, "Immunoglobulin gene transcription is activated by downstream sequence elements," *Cell,* 35:741, 1983.

Quinn, Farina, Gardner, Krutzsch, and Levens, "Multiple components are required for sequence recognition of the ap1 site in the gibbon ape leukemia virus enhancer," *Mol. Cell. Biol.,* 9:4713, 1989.

Ragot et al., "Efficient adenovirus-mediated transfer of a human minidystrophin gene to skeletal muscle of mdx mice," *Nature,* 361:647–650, 1993.

Ravindranath and Morton, "Role of gangliosides in active immunotherapy with melanoma vaccine," *Intern. Rev. Immunol.,* 7: 303–329, 1991.

Redondo, Hata, Brocklehurst, and Krangel, "A T-cell-specific transcriptional enhancer within the human T-cell receptor .delta locus," *Science,* 247:1225, 1990.

Reisman and Rotter, "Induced expression from the moloney murine leukemia virus long terminal repeat during differentiation of human myeloid cells is mediated through its transcriptional enhancer," *Mol. Cell. Biol.,* 9:3571, 1989.

Remington's Pharmaceutical Sciences" 15th Edition, pages 1035–1038 and 1570–1580

Renan, "Cancer genes: current status, future prospects, and applicants in radiotherapy/oncology," *Radiother. Oncol.,* 19:197–218, 1990.

Resendez Jr., Wooden, and Lee, "Identification of highly conserved regulatory domains and protein-binding sites in the promoters of the rat and human genes encoding the stress-inducible 78-kilodalton glucose-regulated protein," *Mol. Cell. Biol.,* 8:4579, 1988.

Rich, Couture, Cardoza, Guiggio, Armentano, Espino, Hehir, Welsh, Smith, Gregory, "Development and analysis of recombinant adenoviruses for gene therapy of cystic fibrosis," *Hum. Gene Ther.,* 4:461–476, 1993.

Ridgeway, "Mammalian expression vectors," *In: Vectors: A survey of molecular cloning vectors and their uses.* Rodriguez and Denhardt, eds. Stoneham: Butterworth, pp. 467–492, 1988.

Ripe, Lorenzen, Brenner, and Breindl, "Regulatory elements in the 5' flanking region and the first intron contribute to transcriptional control of the mouse alpha-1-type collagen gene," *Mol. Cell. Biol.,* 9:2224, 1989.

Rippe, Brenner and Leffert, "DNA-mediated gene transfer into adult rat hepatocytes in primary culture," *Mol. Cell Biol.,* 10:689–695, 1990.

Rittling, Coutinho, Amarm, and Kolbe, "AP-1/jun-binding sites mediate serum inducibility of the human vimentin promoter," *Nuc. Acids Res.,* 17:1619, 1989. Rosen, Sodroski, and Haseltine, "The location of cis-acting regulatory sequences in the human t-cell lymphotropic virus type III (HTLV-111/LAV) long terminal repeat," *Cell,* 41:813, 1988.

Rosenberg et al., *Ann Surg.* 210(4):474–548, 1989

Rosenberg et al., *N. Engl. J. Med.,* 319:1676, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant alpha. 1-antitrypsin gene to the lung epithelium in vivo," *Science,* 252:431–434,1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell*, 68:143–155,1992.

Roux, Jeanteur, Piechaczyk, "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Rovere, Sabbadini, Vallinoto, Fascio, Recigno, Crosti, Ricciardi-Castagnoli, Balestrieri, Tincani, Manfredi, "Dendritic cell presentation of antigens from apoptotic cells in a proinflammatory context: role of opsonizing anti-beta2-glycoprotein I antibodies," *Arthritis Rheum*, 42(7): 1412–1420, 1999

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.*, 2:1144, 1988.

Sambrook et. al., In: *Molecular Cloning: A Laboratory Manual*, 2d Ed., Cold Spring Harbor Laboratory Press, Cold Spring Harbor, N.Y., 1989.

Samulski, Chang, and Shenk, "Helper-free stocks of recombinant adeno-associated viruses: Normal integration does not require viral gene expression," *J Virol*, 63:3822–3828, 1989.

Samulski, Zhu, Xiao, Brook, Housman, Epstein, and Hunter, "Targeted integration of adeno-associated virus (AAV) into human chromosome 19," *EMBO J*, 10:3941–3950, 1991.

Satake, Furukawa, and Ito, "Biological activities of oligonucleotides spanning the f9 point mutation within the enhancer region of polyoma virus DNA," *J. Virology*, 62:970, 1988.

Sato, Tanigami, Yamakawa, Akiyama, Kasumi, Sakamoto, Nakamura, "Allelotype of breast cancer: cumulative allele losses promote tumor progression in primary breast cancer," *Cancer Res.*, 50:7184–7189, 1990.

Savino, d'Apolito, Centra, van Beerendonk, Cleton-Jansen, Whitmore, Crawford, Callen, Zelante, Savoia, "Characterization of copine VII, a new member of the copine family, and its exclusion as a candidate in sporadic breast cancers with loss of heterozygosity at 16q24.3," *Genomics*, 61:219–226, 1999.

Schaffner, Schirm, Muller-Baden, Wever, and Schaffner, "Redundancy of Information in Enhancers as a Principle of Mammalian Transcription Control," *J. Mol. Biol.*, 201:81, 1988.

Searle, Stuart, and Palmiter, "Building a metal-responsive promoter with synthetic regulatory elements," *Mol. Cell. Biol.*, 5:1480, 1985.

Serrano et al., *Nature*, 366:704–707, 1993.

Serrano et al., *Science*, 267(5195):249–252, 1995.

Sharp and Marciniak, "HIV Tar: an RNA Enhancer?," *Cell*, 59:229, 1989.

Shaul and Ben-Levy, "Multiple Nuclear Proteins in Liver Cells are Bound to Hepatitis B Virus Enhancer Element and its Upstream Sequences," *EMBO J*, 6:1913, 1987.

Shelling and Smith, "Targeted integration of transfected and infected adeno-associated virus vectors containing the neomycin resistance gene," *Gene Therapy*, 1:165–169, 1994.

Sherman, Basta, Moore, Brown, and Ting, "Class II Box Consensus Sequences in the HLA-DR.alpha. Gene: Transcriptional Function and Interaction with Nuclear Proteins," *Mol. Cell. Biol.*, 9:50, 1989.

Sleigh and Lockett, "SV40 Enhancer Activation During Retinoic-Acid-Induced Differentiation of F9 Embryonal Carcinoma Cells," *J EMBO*, 4:3831, 1985.

Smith, Huang, Wang, "Common fragile sites and cancer (Review)," *Int. J. Oncol.*, 12:187–196, 1998.

Solodin et al., "A novel series of amphiphilic imidazolinium compounds for in vitro and in vivo gene delivery," *Biochemistry*, 34(41):13537–13544, 1995.

Spalholz, Yang, and Howley, "Transactivation of a Bovine Papilloma Virus Transcriptional Regulatory Element by the E2 Gene Product," *Cell*, 42:183, 1985.

Spandau and Lee, "Trans-Activation of Viral Enhancers by the Hepatitis B Virus X Protein," *J. Virology*, 62:427, 1988.

Spandidos and Wilkie, "Host-Specificities of Papilloma Virus, Moloney Murine Sarcoma Virus and Simian Virus 40 Enhancer Sequences," *EMBO J*, 2:1193, 1983.

Staub, Dho, Henry, Correa, Ishikawa, McGlade, Rotin, "WW domains of Nedd4 bind to the proline-rich PY motifs in the epithelial Na+ channel deleted in Liddle's syndrome," *Embo. J.*, 15:2371–2380, 1996.

Steinman, Inaba, Turley, Pierre, Mellman, "Antigen capture, processing, and presentation by dendritic cells: recent cell biological studies," *Hum Immunol*, 60(7):562–567, 1999.

Stephens and Hentschel, "The Bovine Papilloma Virus Genome and its Uses as a Eukaryotic Vector," *Biochem. J*, 248:1, 1987.

Stratford-Perricaudet and Perricaudet, In: Human Gene Transfer, Eds, O. Cohen-Haguenauer and M. Boiron, Editions John Libbey Eurotext, France, pp. 51–61, 1991.

Stratford-Perricaudet, Levrero, Chasse, Perricaudet, Briand, "Evaluation of the transfer and expression in mice of an enzyme-encoding gene using a human adenovirus vector," *Hum. Gene. Ther.*, 1:241–256, 1990.

Stuart, Searle, and Palmiter, "Identification of Multiple Metal Regulatory Elements in Mouse Metallothionein-I Promoter by Assaying Synthetic Sequences," *Nature*, 317:828, 1985.

Sudol et al., *J. Biol. Chem.* 270:14733–14741, 1995.

Sudol, *Oncogene*, 9:2145–2152, 1994.

Sullivan and Peterlin, "Transcriptional enhancers in the HLA-DQ subregion," *Mol. Cell. Biol.*, 7:3315, 1987.

Sutherland, Baker, Richards, "Fragile sites still breaking," *Trends Genet.*, 14:501–506, 1998.

Swartzendruber and Lehman, "Neoplastic Differentiation: Interaction of Simian Virus 40 and Polyoma Virus with Murine Teratocarcinoma Cells," *J. Cell. Physiology*, 85:179, 1975.

Tacket, Roy, Widera, Swain, Broome, Edelman, "Phase 1 safety and immune response studies of a DNA vaccine encoding hepatitis B surface antigen delivered by a gene delivery device," *Vaccine*, 17(22):2826–9, 1999.

Takebe, Seiki, Fujisawa, Hoy, Yokota, Arai, Yoshida, and Arai, "SRα promoter: an efficient and versatile mammalian cDNA expression system composed of the simian virus 40 early promoter and the R-U5 segment of human T-cell leukemia virus type 1 long terminal repeat," *Mol. Cell. Biol.*, 8:466, 1988.

Tavernier, Gheysen, Duerinck, Can Der Heyden, and Fiers, "Deletion mapping of the inducible promoter of human IFN-beta gene," *Nature*, 301:634, 1983.

Taylor and Kingston, "E1A Trans-Activation of Human HSP70 Gene Promoter Substitution Mutants is Independent of the Composition of Upstream and TATA Elements," *Mol. Cell. Biol.*, 10:176, 1990b.

Taylor and Kingston, "Factor Substitution in a Human HSP70 Gene Promoter: TATA-Dependent and TATA-Independent Interactions," *Mol. Cell. Biol*, 10: 165, 1990a.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.*, 264:15160, 1989.

Thierry et al., "Systemic gene therapy: biodistribution and long-term expression of a transgene in mice," *Proc Natl Acad Sci USA.* 92(21):9742–9746, 1995.

Thiesen, Bosze, Henry, and Charnay, "A DNA Element Responsible for the Different Tissue Specificities of Friend and Moloney Retroviral Enhancers," *J. Virology,* 62:614, 1988.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Tratschin, Miller, Smith, and Carter, "Adeno-associated virus vector for high-frequency integration, expression and rescue of genes in mammalian cells," *Mol. Cell. Biol.,* 5:3258–3260, 1985.

Tratschin, West, Sandbank, and Carter, "A human parvovirus, adeno-associated virus, as a eucaryotic vector: transient expression and encapsidation of the procaryotic gene for chloramphenicol acetyltransferase," *Mol. Cell. Biol.,* 4:2072–2081, 1984.

Treisman, "Transient Accumulation of c-fos RNA Following Serum Stimulation Requires a Conserved 5' Element and c-fos 3' Sequences," *Cell,* 42:889, 1985.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," *Mol. Cell. Biol.,* 9:4759, 1989.

Tronche, Rollier, Herbomel, Bach, Cereghini, Weiss, and Yaniv, "Anatomy of the Rat Albumin Promoter," *Mol. Biol. Med.,* 7:173, 1990.

Trudel and Constantini, "A 3' Enhancer Contributes to the Stage-Specific Expression of the Human Beta-Globin Gene," *Genes and Dev.,* 6:954, 1987.

Tsuda, Callen, Fukutomi, Nakamura, Hirohashi, "Allele loss on chromosome 16q24.2-qter occurs frequently in breast cancer irrespectively of differences in phenotype and extent of spread," *Cancer Res.,* 54: 513–517, 1994.

Tsujimoto and Croce, "Analysis of the structure, transcripts, and protein products of bcl-2, the gene involved in human follicular lymphoma," *Proc Natl Acad Sci USA.* 83(14): 5214–5218, 1986.

Tsujimoto et al., *Science,* 228(4706):1440–1443, 1985.

Tsukamoto et. "The t(14;18) chromosome translocation involved in B-cell neoplasms result from mistakes in VDJ joining," *Science,* 229:1390, 1985.

Tur-Kaspa, Teicher, Levine, Skoultchi and Shafritz, "Use of electroporation to introduce biologically active foreign genes into primary rat hepatocytes," *Mol. Cell Biol.,* 6:716–718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Vannice and Levinson, "Properties of the Human Hepatitis B Virus Enhancer: Position Effects and Cell-Type Non-specificity," *J. Virology,* 62:1305, 1988.

Vasseur, Kress, Montreau, and Blangy, "Isolation and Characterization of Polyoma Virus Mutants Able to Develop in Multipotential Murine Embryonal Carcinoma Cells," *Proc Natl. Acad. Sci. U.S.A.,* 77:1068, 1980.

Vogelstein and Kinzler, "p53 function and dysfunction," *Cell,* 70(4):523–6, 1992.

Walsh, Nienhuis, Samulski, Brown, Miller, Young, and Liu, "Phenotypic correction of Fanconi anemia in human hematopoietic cells with a recombinant adeno-associated virus vector," *J. Clin. Invest,* 94:1440–1448, 1994.

Walsh, Nienhuis, Samulski, Brown, Miller, Young, and Liu, "Phenotypic correction of Fanconi anemia in human hematopoietic cells with a recombinant adeno-associated virus vector," *J. Clin. Invest,* 94:1440–1448, 1994.

Wang and Calame, "SV40 enhancer-binding factors are required at the establishment but not the maintenance step of enhancer-dependent transcriptional activation," *Cell,* 47:241, 1986.

Watanabe et al., "Gene transfection of mouse primordial germ cells in vitro and analysis of their survival and growth control, *Experimental Cell Research,* 230:76–83, 1997.

Weber, De Villiers, and Schaffner, "An SV40 'Enhancer Trap' Incorporates Exogenous Enhancers or Generates Enhancers From its Own Sequences," *Cell,* 36:983, 1984.

Wei, Wei, Samulski, and Barranger, "Expression of the human glucocerebrosidase and arylsulfatase A genes in murine and patient primary fibroblasts transduced by an adeno-associated virus vector," *Gene Therapy,* 1:261–268, 1994.

Weinberg, "Tumor suppressor genes," *Science,* 254(5035): 1138–1146, 1991.

Weinberger, Jat, and Sharp, "Localization of a Repressive Sequence Contributing to B-cell Specificity in the Immunoglobulin Heavy-Chain Enhancer," *Mol. Cell. Biol.,* 8:988, 1984.

Whitmore, Crawford, Apostolou, Eyre, Baker, Lower, Settasatian, Goldup, Seshadri, Gibson, Mathew, Cleton-Jansen, Savoia, Pronk, Auerbach, Doggett, Sutherland, Callen, "Construction of a high-resolution physical and transcription map of chromosome 16q24.3: a region of frequent loss of heterozygosity in sporadic breast cancer," *Genomics,* 50:1–8, 1998.

Winoto and Baltimore, "αβ-lineage-specific Expression of the α T-Cell Receptor Gene by Nearby Silencers," *Cell,* 59:649, 1989.

Wong, Nicolau, Hofschneider, "Appearance of β-lactamase activity in animal cells upon liposome mediated gene transfer," *Gene,* 10:87–94, 1980.

Xie et al., "Breast cancer. Cyr61 is overexpressed, estrogen-inducible, and associated with more advanced disease," *J Biol. Chem. Apr* 27;276(17):14187–94, 2001.

Yang and Huang, "Overcoming the inhibitory effect of serum on lipofection by increasing the charge ratio of cationic liposome to DNA," *Gene Therapy,* 4 (9):950–960, 1997.

Yang et al., "Cellular immunity to viral antigens limits E1-deleted adenoviruses for gene therapy," *Proc. Nat'l Acad. Sci. U.S.A.* 91:4407–4411, 1994.

Yang, Burkholder, Roberts, Martinell and McCabe, "In vivo and in vitro gene transfer to mammalian somatic cells by particle bombardment," *Proc Nat'l Acad. Sci. USA,* 87:9568–9572, 1990.

Yoder, Kang, Zhou, Luo, and Srivastava, "In vivo gene transfer in murine hematopoietic reconstituting stem cells mediated by the adeno-associated virus 2-based vectors," *Blood,* 82 (Supp.): 1:347A, 1994.

Yutzey, Kline, and Konieczny, "An Internal Regulatory Element Controls Troponin I Gene Expression," *Mol. Cell. Biol.,* 9:1397, 1989.

Zhou et al., *Exp. Hematol,* 21:928–933, 1993.

Zhou, Cooper, Kang, Ruggieri, Heimfeld, Srivastava, and Broxmeyer, "Adeno-associated virus 2-mediated high efficiency gene transfer into immature and mature subsets of hematopoietic progenitor cells in human umbilical cord blood," *J. Exp. Med.*, 179:1867–1875, 1994.

Zhu et al., "Systemic gene expression after intravenous DNA delivery into adult mice," *Science*. 261(5118):209–211, 1993.

What is claimed is:

1. An isolated and purified polynucleotide comprising a nucleic acid sequence encoding SEQ ID NO:2.

2. The polynucleotide of claim 1, comprising SEQ ID NO:1.

3. An expression vector comprising a nucleic acid sequence that encodes SEQ ID NO:2.

4. The expression vector of claim 3, wherein the nucleic acid sequence comprises SEQ ID NO:1.

5. A The recombinant host cell comprising a nucleic acid sequence encoding a polypeptide that comprises SEQ ID NO:2.

6. The recombinant host cell of claim 5, wherein the nucleic acid sequence comprises SEQ ID NO:1.

7. A method of preparing a recombinant polypeptide comprising:
   (a) transfecting a cell with a polynucleotide comprising a nucleic acid sequence that encodes SEQ ID NO:2 to produce a transformed host cell; and
   (b) maintaining the transformed host cell under biological conditions sufficient for expression of the polypeptide in the host cell.

8. The method of claim 7, wherein the nucleic acid sequence comprises SEQ ID NO:1.

* * * * *

UNITED STATES PATENT AND TRADEMARK OFFICE
CERTIFICATE OF CORRECTION

| | | |
|---|---|---|
| PATENT NO. | : 7,060,811 B2 | Page 1 of 1 |
| APPLICATION NO. | : 09/978318 | |
| DATED | : June 13, 2006 | |
| INVENTOR(S) | : Aldaz et al. | |

It is certified that error appears in the above-identified patent and that said Letters Patent is hereby corrected as shown below:

In claim 5, column 135, line 61, delete "A The" and insert --A-- therefor.

Signed and Sealed this

Twelfth Day of September, 2006

JON W. DUDAS
*Director of the United States Patent and Trademark Office*

SEQUENCE LISTING

<160> NUMBER OF SEQ ID NOS: 70

<210> SEQ ID NO 1
<211> LENGTH: 2264
<212> TYPE: DNA
<213> ORGANISM: Human

<400> SEQUENCE: 1

```
gcagtgcgca ggcgtgagcg gtcgggcccc gacgcgcgcg ggtctcgttt ggagcgggag      60
tgagttcctg agcgagtgga cccggcagcg ggcgataggg gggccaggtg cctccacagt     120
cagccatggc agcgctgcgc tacgcgggc tggacgacac ggacagtgag gacgagctgc      180
ctccgggctg ggaggagaga accaccaagg acggctggt ttactacgcc aatcacaccg      240
aggagaagac tcagtgggaa catccaaaaa ctggaaaaag aaaacgagtg gcaggagatt     300
tgccatacgg atgggaacaa gaaactgatg agaacggaca agtgtttttt gttgaccata    360
taaataaaag aaccacctac ttggacccaa gactggcgtt tactgtggat gataatccga     420
ccaagccaac caccgcaa agatacgacg gcagcaccac tgccatggaa attctccagg      480
gccgggattt cactggcaaa gtggttgtgg tcactggagc taattcagga ataggttcg      540 aaaccgccaa gtcttttgcc ctccatggtg cacatgtgat cttggcctgc aggaacatgg     600
caagggcgag tgaagcagtg tcacgcattt tagaagaatg gcataaagcc aagtagaag      660 caatgaccct ggacctcgct ctgctccgta gcgtgcagca ttttgctgaa gcattcaagg    720
ccaagaatgt gcctcttcat gtgcttgtgt gcaacgcagc aactttgct ctaccctgga     780 gtctcaccaa agatggcctg gagaccacct ttcaagtgaa tcatctgggg cacttctacc    840
ttgtccagct cctccaggat gttttgtgcc gctcagctcc tgcccgtgtc attgtggtct    900
cctcagagtc ccatcgattt acagatatta acgactcctt gggaaaactg gacttcagtc    960
gcctctctcc aacaaaaaac gactattggg cgatgctggc ttataacagg tccaagctct   1020
gcaacatcct cttctccaac gagctgcacc gtcgcctctc cccacgcggg gtcacgtcga   1080
acgcagtgca tcctggaaat atgatgtact ccaacattca tcgcagctgg tgggtgtaca   1140
cactgctgtt taccttggcg aggcctttca ccaagtccat gcaacaggga gctgccacca   1200
ccgtgtactg tgctgctgtc ccagaactgg agggtctggg agggatgtac ttcaacaact   1260
gctgccgctg catgcccta ccagaagctc agagcgaaga gacggcccgg accctgtggg   1320
cgctcagcga gaggctgatc caagaacggc ttggcagcca gtccggctaa gtggagctca   1380
gagcggatgg gcacacacac ccgccctgtg tgtgtccct cacgcaagtg ccagggctgg   1440
gccccttcca aatgtccctc caacacagat ccgcaagagt aaaggaaata agagcagtca   1500
caacagagtg aaaaatctta agtaccaatg ggaagcaggg aattcctggg gtaaagtatc   1560
acttttctgg ggctgggcta ggcataggtc tctttgcttt ctggtggtgg cctgtttgaa   1620
agtaaaaacc tgcttggtgt gtaggttccg tatctccctg gagaagcacc agcaattctc   1680
tttcttttac tgttatagaa tagcctgagg tccctcgtc ccatccagct accaccacgg   1740
ccaccactga agccggggc tggccttctc ctacttaggg aagaaaagc aagtgttcac   1800 tgctccttgc tgcattgatc caggagataa ttgtttcatt catcctgacc aagactgagc   1860
```

```
cagcttagca actgctgggg agacaaatct cagaaccttg tcccagccag tgaggatgac      1920
agtgacaccc agagggagta gaatacgcag aactaccagg tggcaaagta cttgtcatag      1980
actcctttgc taatgctatg caaaaaattc tttagagatt ataacaaatt tttcaaatca      2040
ttccttagat accttgaaag gcaggaaggg aagcgtatat acttaagaat acacaggata      2100
ttttgggggg cagagaataa aacgttagtt aatcccttty tctgtcaatc acagtctcag      2160
ttctcttgct ttcacattgt acttaaacct cctgctgtgc ctcgcatcct atgcttaata      2220
aaagaacatg cttgaatatc aaaaaaaaaa aaaaaaaaa aaaa                        2264
```

<210> SEQ ID NO 2
<211> LENGTH: 414
<212> TYPE: PRT
<213> ORGANISM: Human

<400> SEQUENCE: 2

```
Met Ala Ala Leu Arg Tyr Ala Gly Leu Asp Asp Thr Asp Ser Glu Asp
  1               5                  10                  15

Glu Leu Pro Pro Gly Trp Glu Glu Arg Thr Thr Lys Asp Gly Trp Val
                 20                  25                  30

Tyr Tyr Ala Asn His Thr Glu Glu Lys Thr Gln Trp Glu His Pro Lys
             35                  40                  45

Thr Gly Lys Arg Lys Arg Val Ala Gly Asp Leu Pro Tyr Gly Trp Glu
         50                  55                  60

Gln Glu Thr Asp Glu Asn Gly Gln Val Phe Phe Val Asp His Ile Asn
  65                  70                  75                  80

Lys Arg Thr Thr Tyr Leu Asp Pro Arg Leu Ala Phe Thr Val Asp Asp
                 85                  90                  95

Asn Pro Thr Lys Pro Thr Thr Arg Gln Arg Tyr Asp Gly Ser Thr Thr
            100                 105                 110

Ala Met Glu Ile Leu Gln Gly Arg Asp Phe Thr Gly Lys Val Val Val
        115                 120                 125

Val Thr Gly Ala Asn Ser Gly Ile Gly Phe Glu Thr Ala Lys Ser Phe
130                 135                 140

Ala Leu His Gly Ala His Val Ile Leu Ala Cys Arg Asn Met Ala Arg
145                 150                 155                 160

Ala Ser Glu Ala Val Ser Arg Ile Leu Glu Glu Trp His Lys Ala Lys
                165                 170                 175

Val Glu Ala Met Thr Leu Asp Leu Ala Leu Leu Arg Ser Val Gln His
            180                 185                 190

Phe Ala Glu Ala Phe Lys Ala Lys Asn Val Pro Leu His Val Leu Val
        195                 200                 205

Cys Asn Ala Ala Thr Phe Ala Leu Pro Trp Ser Leu Thr Lys Asp Gly
    210                 215                 220

Leu Glu Thr Thr Phe Gln Val Asn His Leu Gly His Phe Tyr Leu Val
225                 230                 235                 240

Gln Leu Leu Gln Asp Val Leu Cys Arg Ser Ala Pro Ala Arg Val Ile
                245                 250                 255

Val Val Ser Ser Glu Ser His Arg Phe Thr Asp Ile Asn Asp Ser Leu
            260                 265                 270

Gly Lys Leu Asp Phe Ser Arg Leu Ser Pro Thr Lys Asn Asp Tyr Trp
        275                 280                 285

Ala Met Leu Ala Tyr Asn Arg Ser Lys Leu Cys Asn Ile Leu Phe Ser
    290                 295                 300
```

-continued

Asn Glu Leu His Arg Arg Leu Ser Pro Arg Gly Val Thr Ser Asn Ala
305                 310                 315                 320

Val His Pro Gly Asn Met Met Tyr Ser Asn Ile His Arg Ser Trp Trp
            325                 330                 335

Val Tyr Thr Leu Leu Phe Thr Leu Ala Arg Pro Phe Thr Lys Ser Met
                340                 345                 350

Gln Gln Gly Ala Ala Thr Thr Val Tyr Cys Ala Ala Val Pro Glu Leu
            355                 360                 365

Glu Gly Leu Gly Gly Met Tyr Phe Asn Asn Cys Cys Arg Cys Met Pro
        370                 375                 380

Ser Pro Glu Ala Gln Ser Glu Glu Thr Ala Arg Thr Leu Trp Ala Leu
385                 390                 395                 400

Ser Glu Arg Leu Ile Gln Glu Arg Leu Gly Ser Gln Ser Gly
                405                 410

<210> SEQ ID NO 3
<211> LENGTH: 26
<212> TYPE: DNA
<213> ORGANISM: Homo sapiens

<400> SEQUENCE: 3
acggtggtgg cagctccctg ttgttg                                  26

<210> SEQ ID NO 4
<211> LENGTH: 29
<212> TYPE: DNA
<213> ORGANISM: Homo sapiens

<400> SEQUENCE: 4
acggtggtgg cagctccctg ttgcgatgg                               29

<210> SEQ ID NO 5
<211> LENGTH: 33
<212> TYPE: DNA
<213> ORGANISM: Homo sapiens

<400> SEQUENCE: 5
acggtggtgg cagctccctg ttgacattct tgg                          33

<210> SEQ ID NO 6
<211> LENGTH: 32
<212> TYPE: DNA
<213> ORGANISM: Homo sapiens

<400> SEQUENCE: 6
acggtggtgg cagctccctg ttgccattct tc                           32

<210> SEQ ID NO 7
<211> LENGTH: 30
<212> TYPE: DNA
<213> ORGANISM: Homo sapiens

<400> SEQUENCE: 7
acggtggtgg cagctccctg ttgctattcc                              30

<210> SEQ ID NO 8
<211> LENGTH: 33
<212> TYPE: DNA
<213> ORGANISM: Homo sapiens

<400> SEQUENCE: 8
tggtggcagc tccctgttgt caacaaaaaa cac                33

<210> SEQ ID NO 9
<211> LENGTH: 27
<212> TYPE: DNA
<213> ORGANISM: Homo sapiens

<400> SEQUENCE: 9
acggtggtgg cagctccctg ttgctcc                       27

<210> SEQ ID NO 10
<211> LENGTH: 19
<212> TYPE: DNA
<213> ORGANISM: Homo sapiens

<400> SEQUENCE: 10
tcgcagctgg tgggtgtac                                19

<210> SEQ ID NO 11
<211> LENGTH: 21
<212> TYPE: DNA
<213> ORGANISM: Homo sapiens

<400> SEQUENCE: 11
agctccctgt tgcatggact t                             21

<210> SEQ ID NO 12
<211> LENGTH: 22
<212> TYPE: DNA
<213> ORGANISM: Homo sapiens

<400> SEQUENCE: 12
tgagtgctgt ctccatgttt ga                            22

<210> SEQ ID NO 13
<211> LENGTH: 22
<212> TYPE: DNA
<213> ORGANISM: Homo sapiens

<400> SEQUENCE: 13
tctgctcccc acctctaagt tg                            22

<210> SEQ ID NO 14
<211> LENGTH: 21
<212> TYPE: DNA
<213> ORGANISM: Homo sapiens

<400> SEQUENCE: 14
aggcagtgcg caggcgtgag c                             21

<210> SEQ ID NO 15
<211> LENGTH: 22
<212> TYPE: DNA
<213> ORGANISM: Homo sapiens

<400> SEQUENCE: 15
cagccctggc acttgcgtga gg                            22

<210> SEQ ID NO 16
<211> LENGTH: 22
<212> TYPE: DNA
<213> ORGANISM: Homo sapiens

<400> SEQUENCE: 16

```
tgcgtgaggg gacacacaca gg                                              22

<210> SEQ ID NO 17
<211> LENGTH: 23
<212> TYPE: DNA
<213> ORGANISM: Homo sapiens

<400> SEQUENCE: 17
gagttcctga gcgagtggac ccg                                             23

<210> SEQ ID NO 18
<211> LENGTH: 30
<212> TYPE: DNA
<213> ORGANISM: Homo sapiens

<400> SEQUENCE: 18
tagtttttat tattattagt ttttattatt                                      30

<210> SEQ ID NO 19
<211> LENGTH: 22
<212> TYPE: DNA
<213> ORGANISM: Homo sapiens

<400> SEQUENCE: 19
aatactacat cctaaacaac aa                                              22

<210> SEQ ID NO 20
<211> LENGTH: 30
<212> TYPE: DNA
<213> ORGANISM: Homo sapiens

<400> SEQUENCE: 20
agtttttatt attatgagtt tttattaaat                                      30

<210> SEQ ID NO 21
<211> LENGTH: 20
<212> TYPE: DNA
<213> ORGANISM: Homo sapiens
<220> FEATURE:
<221> NAME/KEY: modified_base
<222> LOCATION: (3)..(5)
<223> OTHER INFORMATION: R = A OR G

<400> SEQUENCE: 21
ccrcrcaata ctacatccta                                                 20

<210> SEQ ID NO 22
<211> LENGTH: 20
<212> TYPE: DNA
<213> ORGANISM: Homo sapiens
<220> FEATURE:
<221> NAME/KEY: modified_base
<222> LOCATION: (11)
<223> OTHER INFORMATION: Y = C OR T/U

<400> SEQUENCE: 22
gggatgaggt ygttttgttt                                                 20

<210> SEQ ID NO 23
<211> LENGTH: 24
<212> TYPE: DNA
<213> ORGANISM: Homo sapiens

<400> SEQUENCE: 23
```

| tcataaatct ctattaaaca acaa | 24 |

```
<210> SEQ ID NO 24
<211> LENGTH: 21
<212> TYPE: DNA
<213> ORGANISM: Homo sapiens
<220> FEATURE:
<221> NAME/KEY: modified_base
<222> LOCATION: (2)
<223> OTHER INFORMATION: Y = C OR T/U

<400> SEQUENCE: 24
```

| gygtagtgtt gtattttgaa t | 21 |

```
<210> SEQ ID NO 25
<211> LENGTH: 28
<212> TYPE: DNA
<213> ORGANISM: Homo sapiens

<400> SEQUENCE: 25
```

| tcacaatctc tattatatat tttaacta | 28 |

```
<210> SEQ ID NO 26
<211> LENGTH: 19
<212> TYPE: DNA
<213> ORGANISM: Homo sapiens
<220> FEATURE:
<221> NAME/KEY: modified_base
<222> LOCATION: (9)..(11)
<223> OTHER INFORMATION: R = A OR G

<400> SEQUENCE: 26
```

| tcctccccrc rcaaataac | 19 |

```
<210> SEQ ID NO 27
<211> LENGTH: 30
<212> TYPE: DNA
<213> ORGANISM: Homo sapiens

<400> SEQUENCE: 27
```

| ttattattat gagtttttat taaataatag | 30 |

```
<210> SEQ ID NO 28
<211> LENGTH: 1625
<212> TYPE: DNA
<213> ORGANISM: Homo sapiens

<400> SEQUENCE: 28
```

| ggcacgaggc agtgcgcagg cgtgagcggt cgggccccga cgcgcgcggg tctcgtttgg | 60 |
| agcgggagtg agttcctgag cgagtggacc cggcagcggg cgatagggg gccaggtgcc | 120 |
| tccacagtca gccatggcag cgctgcgcta cgcggggctg gacgacacgg acagtgagga | 180 |
| cgagctgcct ccgggctggg aggagagaac caccaaggac ggctgggttt actacgccaa | 240 |
| tcacaccgag gagaagactc agtgggaaca tccaaaaact ggaaaaagaa acgagtggc | 300 |
| aggagatttg ccatacggat gggaacaaga aactgatgag aacggacaag tgttttttgt | 360 |
| tgaccatata aataaagaa ccacctactt ggacccaaga ctggcgttta ctgtggatga | 420 |
| taatccgacc aagccaacca cccggcaaag atacgacggc agcaccactg ccatggaaat | 480 |
| tctccagggc cgggatttca ctggcaaagt ggttgtggtc actggagcta attcaggaat | 540 |
| agcaacaggg agctgccacc accgtgtact gtgctgctgt cccagaactg agggtctgg | 600 |
| gagggatgta cttcaacaac tgctgccgct gcatgccctc accagaagct cagagcgaag | 660 |

-continued

```
agacggcccg gaccctgtgg gcgctcagcg agaggctgat ccaagaacgg cttggcagcc    720
agtccggcta agtggagctc agagcggatg ggcacacaca cccgccctgt gtgtgtcccc    780
tcacgcaagt gccagggctg gccccttcc aaatgtccct ccaacacaga tccgcaagag     840
taaaggaaat aagagcagtc acaacagagt gaaaaatctt aagtaccaat gggaagcagg    900
gaattcctgg ggtaaagtat cacttttctg gggctgggct aggcataggt ctctttgctt    960
tctggtggtg gcctgtttga agtaaaaac ctgcttggtg tgtaggttcc gtatctccct    1020
ggagaagcac cagcaattct ctttcttttta ctgttataga atagcctgag gtcccctcgt   1080
cccatccagc taccaccacg gccaccactg cagccggggg ctggccttct cctacttagg   1140
gaagaaaaag caagtgttca ctgctccttg ctgcattgat ccaggagata attgtttcat   1200
tcatcctgac caagactgag ccagcttagc aactgctggg gagacaaatc tcagaacctt   1260
gtcccagcca gtgaggatga cagtgacacc cagagggagt agaatacgca gaactaccag   1320
gtggcaaagt acttgtcata gactcctttg ctaatgctat gcaaaaaatt ctttagagat   1380
tataacaaat ttttcaaatc attccttaga taccttgaaa ggcaggaagg gaagcgtata   1440
tacttaagaa tacacaggat attttggggg gcagagaata aaacgttagt taatcccttt   1500
gtctgtcaat cacagtctca gttctcttgc tttcacattg tacttaaacc tcctgctgtg   1560
cctcgcatcc tatgcttaat aaagaacat gcttgaatat caaaaaaaaa aaaaaaaaa    1620 aaaaa                                                                 1625
```

<210> SEQ ID NO 29
<211> LENGTH: 23
<212> TYPE: DNA
<213> ORGANISM: Homo sapiens

<400> SEQUENCE: 29

```
tagtgttgta ttttgaatag tag                                              23
```

<210> SEQ ID NO 30
<211> LENGTH: 1625
<212> TYPE: DNA
<213> ORGANISM: Homo sapiens
<220> FEATURE:
<221> NAME/KEY: CDS
<222> LOCATION: (134)..(1069)

<400> SEQUENCE: 30

```
ggcacgaggc agtgcgcagg cgtgagcggt cgggccccga cgcgcgcggg tctcgtttgg     60
agcgggagtg agttcctgag cgagtggacc cggcagcggg cgatagggg gccaggtgcc    120 tccacagtca gcc atg gca gcg ctg cgc tac gcg ggg ctg gac gac acg       169
               Met Ala Ala Leu Arg Tyr Ala Gly Leu Asp Asp Thr
                 1               5                  10 gac agt gag gac gag ctg cct ccg ggc tgg gag gag aga acc acc aag      217
Asp Ser Glu Asp Glu Leu Pro Pro Gly Trp Glu Glu Arg Thr Thr Lys
         15                  20                  25 gac ggc tgg gtt tac tac gcc aat cac acc gag gag aag act cag tgg      265
Asp Gly Trp Val Tyr Tyr Ala Asn His Thr Glu Glu Lys Thr Gln Trp
     30                  35                  40 gaa cat cca aaa act gga aaa aga aaa cga gtg gca gga gat ttg cca      313
Glu His Pro Lys Thr Gly Lys Arg Lys Arg Val Ala Gly Asp Leu Pro
 45                  50                  55                  60 tac gga tgg gaa caa gaa act gat gag aac gga caa gtg ttt ttt gtt      361
Tyr Gly Trp Glu Gln Glu Thr Asp Glu Asn Gly Gln Val Phe Phe Val
                 65                  70                  75
```

-continued

| | |
|---|---|
| gac cat ata aat aaa aga acc acc tac ttg gac cca aga ctg gcg ttt<br>Asp His Ile Asn Lys Arg Thr Thr Tyr Leu Asp Pro Arg Leu Ala Phe<br>80 85 90 | 409 |
| act gtg gat gat aat ccg acc aag cca acc acc cgg caa aga tac gac<br>Thr Val Asp Asp Asn Pro Thr Lys Pro Thr Thr Arg Gln Arg Tyr Asp<br>95 100 105 | 457 |
| ggc agc acc act gcc atg gaa att ctc cag ggc cgg gat ttc act ggc<br>Gly Ser Thr Thr Ala Met Glu Ile Leu Gln Gly Arg Asp Phe Thr Gly<br>110 115 120 | 505 |
| aaa gtg gtt gtg gtc act gga gct aat tca gga ata gca aca ggg agc<br>Lys Val Val Val Val Thr Gly Ala Asn Ser Gly Ile Ala Thr Gly Ser<br>125 130 135 140 | 553 |
| tgc cac cac cgt gta ctg tgc tgc tgt ccc aga act gga ggg tct ggg<br>Cys His His Arg Val Leu Cys Cys Cys Pro Arg Thr Gly Gly Ser Gly<br>145 150 155 | 601 |
| agg gat gta ctt caa caa ctg ctg ccg ctg cat gcc ctc acc aga agc<br>Arg Asp Val Leu Gln Gln Leu Leu Pro Leu His Ala Leu Thr Arg Ser<br>160 165 170 | 649 |
| tca gag cga aga gac ggc ccg gac cct gtg ggc gct cag cga gag gct<br>Ser Glu Arg Arg Asp Gly Pro Asp Pro Val Gly Ala Gln Arg Glu Ala<br>175 180 185 | 697 |
| gat cca aga acg gct tgg cag cca gtc cgg cta agt gga gct cag agc<br>Asp Pro Arg Thr Ala Trp Gln Pro Val Arg Leu Ser Gly Ala Gln Ser<br>190 195 200 | 745 |
| gga tgg gca cac aca ccc gcc ctg tgt gtg tcc cct cac gca agt gcc<br>Gly Trp Ala His Thr Pro Ala Leu Cys Val Ser Pro His Ala Ser Ala<br>205 210 215 220 | 793 |
| agg gct ggg ccc ctt cca aat gtc cct cca aca cag atc cgc aag agt<br>Arg Ala Gly Pro Leu Pro Asn Val Pro Pro Thr Gln Ile Arg Lys Ser<br>225 230 235 | 841 |
| aaa gga aat aag agc agt cac aac aga gtg aaa aat ctt aag tac caa<br>Lys Gly Asn Lys Ser Ser His Asn Arg Val Lys Asn Leu Lys Tyr Gln<br>240 245 250 | 889 |
| tgg gaa gca ggg aat tcc tgg ggt aaa gta tca ctt ttc tgg ggc tgg<br>Trp Glu Ala Gly Asn Ser Trp Gly Lys Val Ser Leu Phe Trp Gly Trp<br>255 260 265 | 937 |
| gct agg cat agg tct ctt tgc ttt ctg gtg gtg gcc tgt ttg aaa gta<br>Ala Arg His Arg Ser Leu Cys Phe Leu Val Val Ala Cys Leu Lys Val<br>270 275 280 | 985 |
| aaa acc tgc ttg gtg tgt agg ttc cgt atc tcc ctg gag aag cac cag<br>Lys Thr Cys Leu Val Cys Arg Phe Arg Ile Ser Leu Glu Lys His Gln<br>285 290 295 300 | 1033 |
| caa ttc tct ttc ttt tac tgt tat aga ata gcc tga ggtcccctcg<br>Gln Phe Ser Phe Phe Tyr Cys Tyr Arg Ile Ala<br>305 310 | 1079 |
| tcccatccag ctaccaccac ggccaccact gcagccgggg gctggccttc tcctacttag | 1139 |
| ggaagaaaaa gcaagtgttc actgctcctt gctgcattga tccaggagat aattgtttca | 1199 |
| ttcatcctga ccaagactga gccagcttag caactgctgg ggagacaaat ctcagaacct | 1259 |
| tgtcccagcc agtgaggatg acagtgacac ccagagggag tagaatacgc agaactacca | 1319 |
| ggtggcaaag tacttgtcat agactccttt gctaatgcta tgcaaaaaat tctttagaga | 1379 |
| ttataacaaa ttttttcaaat cattcctag ataccttgaa aggcaggaag ggaagcgtat | 1439 |
| atacttaaga atacacagga tattttgggg ggcagagaat aaaacgttag ttaatcccctt | 1499 |
| tgtctgtcaa tcacagtctc agttctcttg ctttcacatt gtacttaaac ctcctgctgt | 1559 |
| gcctcgcatc ctatgcttaa taaaagaaca tgcttgaata tcaaaaaaaa aaaaaaaaa | 1619 |

-continued aaaaaa 1625

<210> SEQ ID NO 31
<211> LENGTH: 311
<212> TYPE: PRT
<213> ORGANISM: Homo sapiens

<400> SEQUENCE: 31

```
Met Ala Ala Leu Arg Tyr Ala Gly Leu Asp Asp Thr Asp Ser Glu Asp
1               5                   10                  15

Glu Leu Pro Pro Gly Trp Glu Glu Arg Thr Thr Lys Asp Gly Trp Val
            20                  25                  30

Tyr Tyr Ala Asn His Thr Glu Glu Lys Thr Gln Trp Glu His Pro Lys
        35                  40                  45

Thr Gly Lys Arg Lys Arg Val Ala Gly Asp Leu Pro Tyr Gly Trp Glu
    50                  55                  60

Gln Glu Thr Asp Glu Asn Gly Gln Val Phe Phe Val Asp His Ile Asn
65                  70                  75                  80

Lys Arg Thr Thr Tyr Leu Asp Pro Arg Leu Ala Phe Thr Val Asp Asp
                85                  90                  95

Asn Pro Thr Lys Pro Thr Thr Arg Gln Arg Tyr Asp Gly Ser Thr Thr
            100                 105                 110

Ala Met Glu Ile Leu Gln Gly Arg Asp Phe Thr Gly Lys Val Val Val
        115                 120                 125

Val Thr Gly Ala Asn Ser Gly Ile Ala Thr Gly Ser Cys His His Arg
    130                 135                 140

Val Leu Cys Cys Cys Pro Arg Thr Gly Gly Ser Gly Arg Asp Val Leu
145                 150                 155                 160

Gln Gln Leu Leu Pro Leu His Ala Leu Thr Arg Ser Ser Glu Arg Arg
                165                 170                 175

Asp Gly Pro Asp Pro Val Gly Ala Gln Arg Glu Ala Asp Pro Arg Thr
            180                 185                 190

Ala Trp Gln Pro Val Arg Leu Ser Gly Ala Gln Ser Gly Trp Ala His
        195                 200                 205

Thr Pro Ala Leu Cys Val Ser Pro His Ala Ser Ala Arg Ala Gly Pro
    210                 215                 220

Leu Pro Asn Val Pro Pro Thr Gln Ile Arg Lys Ser Lys Gly Asn Lys
225                 230                 235                 240

Ser Ser His Asn Arg Val Lys Asn Leu Lys Tyr Gln Trp Glu Ala Gly
                245                 250                 255

Asn Ser Trp Gly Lys Val Ser Leu Phe Trp Gly Trp Ala Arg His Arg
            260                 265                 270

Ser Leu Cys Phe Leu Val Val Ala Cys Leu Lys Val Lys Thr Cys Leu
        275                 280                 285

Val Cys Arg Phe Arg Ile Ser Leu Glu Lys His Gln Gln Phe Ser Phe
    290                 295                 300

Phe Tyr Cys Tyr Arg Ile Ala
305                 310
```

<210> SEQ ID NO 32
<211> LENGTH: 1732
<212> TYPE: DNA
<213> ORGANISM: Homo sapiens
<220> FEATURE:
<221> NAME/KEY: CDS
<222> LOCATION: (134)..(838)

<400> SEQUENCE: 32

```
ggcacgaggc agtgcgcagg cgtgagcggt cgggccccga cgcgcgcggg tctcgtttgg      60
agcgggagtg agttcctgag cgagtggacc cggcagcggg cgatagggg gccaggtgcc      120 tccacagtca gcc atg gca gcg ctg cgc tac gcg ggg ctg gac gac acg        169
            Met Ala Ala Leu Arg Tyr Ala Gly Leu Asp Asp Thr
             1               5                  10 gac agt gag gac gag ctg cct ccg ggc tgg gag gag aga acc acc aag        217
Asp Ser Glu Asp Glu Leu Pro Pro Gly Trp Glu Glu Arg Thr Thr Lys
         15                  20                  25 gac ggc tgg gtt tac tac gcc aat cac acc gag gag aag act cag tgg        265
Asp Gly Trp Val Tyr Tyr Ala Asn His Thr Glu Glu Lys Thr Gln Trp
     30                  35                  40 gaa cat cca aaa act gga aaa aga aaa cga gtg gca gga gat ttg cca        313
Glu His Pro Lys Thr Gly Lys Arg Lys Arg Val Ala Gly Asp Leu Pro
 45                  50                  55                  60 tac gga tgg gaa caa gaa act gat gag aac gga caa gtg ttt ttt gtt        361
Tyr Gly Trp Glu Gln Glu Thr Asp Glu Asn Gly Gln Val Phe Phe Val
                 65                  70                  75 gac cat ata aat aaa aga acc acc tac ttg gac cca aga ctg gcg ttt        409
Asp His Ile Asn Lys Arg Thr Thr Tyr Leu Asp Pro Arg Leu Ala Phe
             80                  85                  90 act gtg gat gat aat ccg acc aag cca acc acc cgg caa aga tac gac        457
Thr Val Asp Asp Asn Pro Thr Lys Pro Thr Thr Arg Gln Arg Tyr Asp
         95                 100                 105 ggc agc acc act gcc atg gaa att ctc cag ggc cgg gat ttc act ggc        505
Gly Ser Thr Thr Ala Met Glu Ile Leu Gln Gly Arg Asp Phe Thr Gly
110                 115                 120 aaa gtg gtt gtg gtc act gga gct aat tca gga ata ggg ttc gaa acc        553
Lys Val Val Val Val Thr Gly Ala Asn Ser Gly Ile Gly Phe Glu Thr
125                 130                 135                 140 gcc aag tct ttt gcc ctc cat ggt gca cat gtg atc ttg gcc tgc agg        601
Ala Lys Ser Phe Ala Leu His Gly Ala His Val Ile Leu Ala Cys Arg
                145                 150                 155 aac atg gca agg gcg agt gaa gca gtg tca cgc att tta gaa gaa tgg        649
Asn Met Ala Arg Ala Ser Glu Ala Val Ser Arg Ile Leu Glu Glu Trp
            160                 165                 170 caa cag gga gct gcc acc acc gtg tac tgt gct gct gtc cca gaa ctg        697
Gln Gln Gly Ala Ala Thr Thr Val Tyr Cys Ala Ala Val Pro Glu Leu
        175                 180                 185 gag ggt ctg gga ggg atg tac ttc aac aac tgc tgc cgc tgc atg ccc        745
Glu Gly Leu Gly Gly Met Tyr Phe Asn Asn Cys Cys Arg Cys Met Pro
    190                 195                 200 tca cca gaa gct cag agc gaa gag acg gcc cgg acc ctg tgg gcg ctc        793
Ser Pro Glu Ala Gln Ser Glu Glu Thr Ala Arg Thr Leu Trp Ala Leu
205                 210                 215                 220 agc gag agg ctg atc caa gaa cgg ctt ggc agc cag tcc ggc taa            838
Ser Glu Arg Leu Ile Gln Glu Arg Leu Gly Ser Gln Ser Gly
                225                 230                 235 gtggagctca gagcggatgg gcacacacac ccgccctgtg tgtgtcccct cacgcaagtg      898
ccagggctgg gccccttcca aatgtccctc caacacagat ccgcaagagt aaaggaaata     958
agagcagtca caacagagtg aaaaatctta agtaccaatg ggaagcaggg aattcctggg     1018
gtaaagtatc acttttctgg ggctgggcta ggcataggtc tctttgcttt ctggtggtgg     1078
cctgtttgaa agtaaaaacc tgcttggtgt gtaggttccg tatctccctg gagaagcacc     1138
agcaattctc tttcttttac tgttatagaa tagcctgagg tccctcgtc ccatccagct      1198 accaccacgg ccaccactgc agccggggc tggccttctc ctacttaggg aagaaaaagc      1258
```

```
aagtgttcac tgctccttgc tgcattgatc caggagataa ttgtttcatt catcctgacc    1318
aagactgagc cagcttagca actgctgggg agacaaatct cagaaccttg tcccagccag    1378
tgaggatgac agtgacaccc agagggagta gaatacgcag aactaccagg tggcaaagta    1438
cttgtcatag actcctttgc taatgctatg caaaaaattc tttagagatt ataacaaatt    1498
tttcaaatca ttccttagat accttgaaag gcaggaaggg aagcgtatat acttaagaat    1558
acacaggata ttttgggggg cagagaataa aacgttagtt aatcccttttg tctgtcaatc    1618 acagtctcag ttctcttgct ttcacattgt acttaaacct cctgctgtgc ctcgcatcct    1678
atgcttaata aagaacatg cttgaatatc aaaaaaaaaa aaaaaaaaaa aaaa          1732
```

<210> SEQ ID NO 33
<211> LENGTH: 234
<212> TYPE: PRT
<213> ORGANISM: Homo sapiens

<400> SEQUENCE: 33

```
Met Ala Ala Leu Arg Tyr Ala Gly Leu Asp Asp Thr Asp Ser Glu Asp
 1               5                  10                  15

Glu Leu Pro Pro Gly Trp Glu Glu Arg Thr Thr Lys Asp Gly Trp Val
            20                  25                  30

Tyr Tyr Ala Asn His Thr Glu Glu Lys Thr Gln Trp Glu His Pro Lys
        35                  40                  45

Thr Gly Lys Arg Lys Arg Val Ala Gly Asp Leu Pro Tyr Gly Trp Glu
    50                  55                  60

Gln Glu Thr Asp Glu Asn Gly Gln Val Phe Phe Val Asp His Ile Asn
65                  70                  75                  80

Lys Arg Thr Thr Tyr Leu Asp Pro Arg Leu Ala Phe Thr Val Asp Asp
                85                  90                  95

Asn Pro Thr Lys Pro Thr Thr Arg Gln Arg Tyr Asp Gly Ser Thr Thr
            100                 105                 110

Ala Met Glu Ile Leu Gln Gly Arg Asp Phe Thr Gly Lys Val Val Val
        115                 120                 125

Val Thr Gly Ala Asn Ser Gly Ile Gly Phe Glu Thr Ala Lys Ser Phe
    130                 135                 140

Ala Leu His Gly Ala His Val Ile Leu Ala Cys Arg Asn Met Ala Arg
145                 150                 155                 160

Ala Ser Glu Ala Val Ser Arg Ile Leu Glu Glu Trp Gln Gln Gly Ala
                165                 170                 175

Ala Thr Thr Val Tyr Cys Ala Ala Val Pro Glu Leu Glu Gly Leu Gly
            180                 185                 190

Gly Met Tyr Phe Asn Asn Cys Cys Arg Cys Met Pro Ser Pro Glu Ala
        195                 200                 205

Gln Ser Glu Glu Thr Ala Arg Thr Leu Trp Ala Leu Ser Glu Arg Leu
    210                 215                 220

Ile Gln Glu Arg Leu Gly Ser Gln Ser Gly
225                 230
```

<210> SEQ ID NO 34
<211> LENGTH: 19
<212> TYPE: DNA
<213> ORGANISM: Homo sapiens

<400> SEQUENCE: 34

```
agcaggcgtg agcggtcgg                                                   19
```

<210> SEQ ID NO 35
<211> LENGTH: 23
<212> TYPE: DNA
<213> ORGANISM: Homo sapiens

<400> SEQUENCE: 35
actggatttc agcttcgtgg tcg                                              23

<210> SEQ ID NO 36
<211> LENGTH: 20
<212> TYPE: DNA
<213> ORGANISM: Homo sapiens

<400> SEQUENCE: 36
tccgtgggct gtgcagggtc                                                  20

<210> SEQ ID NO 37
<211> LENGTH: 28
<212> TYPE: DNA
<213> ORGANISM: Homo sapiens

<400> SEQUENCE: 37 ttcccctac ttccttctta tatctggc                                          28

<210> SEQ ID NO 38
<211> LENGTH: 27
<212> TYPE: DNA
<213> ORGANISM: Homo sapiens

<400> SEQUENCE: 38
atcctcactc caccctatga tctcatc                                          27

<210> SEQ ID NO 39
<211> LENGTH: 24
<212> TYPE: DNA
<213> ORGANISM: Homo sapiens

<400> SEQUENCE: 39
atggtcttta cttctccctg gcac                                             24

<210> SEQ ID NO 40
<211> LENGTH: 29
<212> TYPE: DNA
<213> ORGANISM: Homo sapiens

<400> SEQUENCE: 40
acttctgcta agattacaga tacacactg                                        29

<210> SEQ ID NO 41
<211> LENGTH: 26
<212> TYPE: DNA
<213> ORGANISM: Homo sapiens

<400> SEQUENCE: 41
agttctttca ggtttaagga ataagc                                           26

<210> SEQ ID NO 42
<211> LENGTH: 28
<212> TYPE: DNA
<213> ORGANISM: Homo sapiens

<400> SEQUENCE: 42
tagatctaag tggatctcat tatagcag                                           28

<210> SEQ ID NO 43
<211> LENGTH: 25
<212> TYPE: DNA
<213> ORGANISM: Homo sapiens

<400> SEQUENCE: 43
acttggggta atttaagtgg tgctc                                              25

<210> SEQ ID NO 44
<211> LENGTH: 27
<212> TYPE: DNA
<213> ORGANISM: Homo sapiens

<400> SEQUENCE: 44
aactttacac actccactga aatctcc                                            27

<210> SEQ ID NO 45
<211> LENGTH: 21
<212> TYPE: DNA
<213> ORGANISM: Homo sapiens

<400> SEQUENCE: 45
attaaacagg ggaattccga c                                                  21

<210> SEQ ID NO 46
<211> LENGTH: 21
<212> TYPE: DNA
<213> ORGANISM: Homo sapiens

<400> SEQUENCE: 46
tctcccaatt gtgttcatct g                                                  21

<210> SEQ ID NO 47
<211> LENGTH: 19
<212> TYPE: DNA
<213> ORGANISM: Homo sapiens

<400> SEQUENCE: 47
acatccatgg atcccgaag                                                     19

<210> SEQ ID NO 48
<211> LENGTH: 23
<212> TYPE: DNA
<213> ORGANISM: Homo sapiens

<400> SEQUENCE: 48
tggtatgaga aagggataa gtg                                                 23

<210> SEQ ID NO 49
<211> LENGTH: 25
<212> TYPE: DNA
<213> ORGANISM: Homo sapiens

<400> SEQUENCE: 49
tgcacccagc attccttaga tttcc                                              25

<210> SEQ ID NO 50
<211> LENGTH: 20
<212> TYPE: DNA
<213> ORGANISM: Homo sapiens

<400> SEQUENCE: 50

```
accagactca tgcccgcaag                                           20

<210> SEQ ID NO 51
<211> LENGTH: 23
<212> TYPE: DNA
<213> ORGANISM: Homo sapiens

<400> SEQUENCE: 51
aaatgacgcc atctcatcac tcc                                       23

<210> SEQ ID NO 52
<211> LENGTH: 24
<212> TYPE: DNA
<213> ORGANISM: Homo sapiens

<400> SEQUENCE: 52
tgttttcctg gcatctacga gaag                                      24

<210> SEQ ID NO 53
<211> LENGTH: 17
<212> TYPE: DNA
<213> ORGANISM: Homo sapiens

<400> SEQUENCE: 53
tttttaacag tcacacc                                              17

<210> SEQ ID NO 54
<211> LENGTH: 17
<212> TYPE: DNA
<213> ORGANISM: Homo sapiens

<400> SEQUENCE: 54
tgtgtttcag atttgcc                                              17

<210> SEQ ID NO 55
<211> LENGTH: 17
<212> TYPE: DNA
<213> ORGANISM: Homo sapiens

<400> SEQUENCE: 55
ttttgggcag ccatata                                              17

<210> SEQ ID NO 56
<211> LENGTH: 17
<212> TYPE: DNA
<213> ORGANISM: Homo sapiens

<400> SEQUENCE: 56
taaaccatag ggttcga                                              17

<210> SEQ ID NO 57
<211> LENGTH: 17
<212> TYPE: DNA
<213> ORGANISM: Homo sapiens

<400> SEQUENCE: 57
ctcattgcag cataaag                                              17

<210> SEQ ID NO 58
<211> LENGTH: 17
<212> TYPE: DNA
<213> ORGANISM: Homo sapiens
```

```
<400> SEQUENCE: 58 tttttttcagg cctcttc                                              17

<210> SEQ ID NO 59
<211> LENGTH: 17
<212> TYPE: DNA
<213> ORGANISM: Homo sapiens

<400> SEQUENCE: 59
tatttttaag atttaca                                               17

<210> SEQ ID NO 60
<211> LENGTH: 17
<212> TYPE: DNA
<213> ORGANISM: Homo sapiens

<400> SEQUENCE: 60
ggatttccag caacagg                                               17

<210> SEQ ID NO 61
<211> LENGTH: 17
<212> TYPE: DNA
<213> ORGANISM: Homo sapiens

<400> SEQUENCE: 61
acgccaagta aggggggc                                              17

<210> SEQ ID NO 62
<211> LENGTH: 17
<212> TYPE: DNA
<213> ORGANISM: Homo sapiens

<400> SEQUENCE: 62
gcaggaggtt tgtatgt                                               17

<210> SEQ ID NO 63
<211> LENGTH: 17
<212> TYPE: DNA
<213> ORGANISM: Homo sapiens

<400> SEQUENCE: 63
ttgttgagta agtgtct                                               17

<210> SEQ ID NO 64
<211> LENGTH: 17
<212> TYPE: DNA
<213> ORGANISM: Homo sapiens

<400> SEQUENCE: 64
ggaataggta ggctctt                                               17

<210> SEQ ID NO 65
<211> LENGTH: 17
<212> TYPE: DNA
<213> ORGANISM: Homo sapiens

<400> SEQUENCE: 65
agaatgggta agcgctt                                               17

<210> SEQ ID NO 66
<211> LENGTH: 17
<212> TYPE: DNA
<213> ORGANISM: Homo sapiens
```

```
<400> SEQUENCE: 66
gaatgtgtga gtgttcc                                                      17

<210> SEQ ID NO 67
<211> LENGTH: 17
<212> TYPE: DNA
<213> ORGANISM: Homo sapiens

<400> SEQUENCE: 67
cccatcggtg ggtttga                                                      17

<210> SEQ ID NO 68
<211> LENGTH: 17
<212> TYPE: DNA
<213> ORGANISM: Homo sapiens

<400> SEQUENCE: 68
gtccatggta agagaac                                                      17

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 69

Leu Pro Pro Gly Trp Glu Glu Arg Thr Thr Lys Asp Gly Trp Val Tyr
  1               5                  10                  15

Tyr Ala Asn His Thr Glu Glu Lys Thr Gln Trp Glu His Pro
             20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 70

Leu Pro Tyr Gly Trp Glu Gln Glu Thr Asp Glu Asn Gly Gln Val Phe
  1               5                  10                  15

Phe Val Asp His Ile Asn Lys Arg Thr Thr Tyr Leu Asp Pro
             20                  25                  30
```